(12) United States Patent
Nomura et al.

(10) Patent No.: US 8,258,310 B2
(45) Date of Patent: Sep. 4, 2012

(54) OXADIAZOLE DERIVATIVE, LIGHT-EMITTING ELEMENT MATERIAL, LIGHT-EMITTING ELEMENT, LIGHT-EMITTING DEVICE, AND ELECTRONIC DEVICE

(75) Inventors: Hiroko Nomura, Fukuoka (JP); Sachiko Kawakami, Kanagawa (JP); Nobuharu Ohsawa, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 149 days.

(21) Appl. No.: 12/725,728

(22) Filed: Mar. 17, 2010

(65) Prior Publication Data

US 2010/0240902 A1 Sep. 23, 2010

(30) Foreign Application Priority Data

Mar. 20, 2009 (JP) .................. 2009-069176

(51) Int. Cl.
*C07D 271/06* (2006.01)
*B32B 9/00* (2006.01)
*H01J 1/62* (2006.01)

(52) U.S. Cl. ........ 548/131; 313/504; 313/506; 428/690; 428/917; 548/125

(58) Field of Classification Search ............... 548/125, 548/131; 428/690, 917; 313/504, 506; 315/169.3
See application file for complete search history.

(56) References Cited

U.S. PATENT DOCUMENTS

| 6,406,804 | B1 | 6/2002 | Higashi et al. | |
| 7,705,157 | B2 * | 4/2010 | Leclerc et al. | 548/101 |
| 7,927,720 | B2 * | 4/2011 | Nomura et al. | 428/690 |

FOREIGN PATENT DOCUMENTS

CN 1854136 A * 11/2006

OTHER PUBLICATIONS

Tang, C.W. et al, "Organic Electroluminescent Diodes," Applied Physics Letters, vol. 51, No. 12, Sep. 21, 1987, pp. 913-915.
Adachi, C. et al, "Electroluminescence in Organic Films with Three-Layer Structure," Japanese Journal of Applied Physics, vol. 27, No. 2, Feb. 20, 1988, pp. L269-L271.

* cited by examiner

*Primary Examiner* — Golam M M Shameem
(74) *Attorney, Agent, or Firm* — Husch Blackwell LLP

(57) ABSTRACT

An object is to provide a novel material having a bipolar property. Another object is to provide an oxadiazole derivative having a wide band gap. Another object is to reduce power consumption of a light-emitting element, a light-emitting device, and an electronic device. The present invention provides an oxadiazole derivative represented by General Formula (1). In the formula, $Ar^1$ represents a substituted or unsubstituted aryl group having 6 to 10 carbon atoms in a ring, A represents a substituted or unsubstituted phenylene group, $R^{11}$ to $R^{15}$ and $R^{21}$ to $R^{25}$ are independently any of hydrogen, an alkyl group having 1 to 4 carbon atoms, an aryl group having 6 to 10 carbon atoms in a ring, and a substituted or unsubstituted 9H-carbazol-9-yl group.

20 Claims, 33 Drawing Sheets

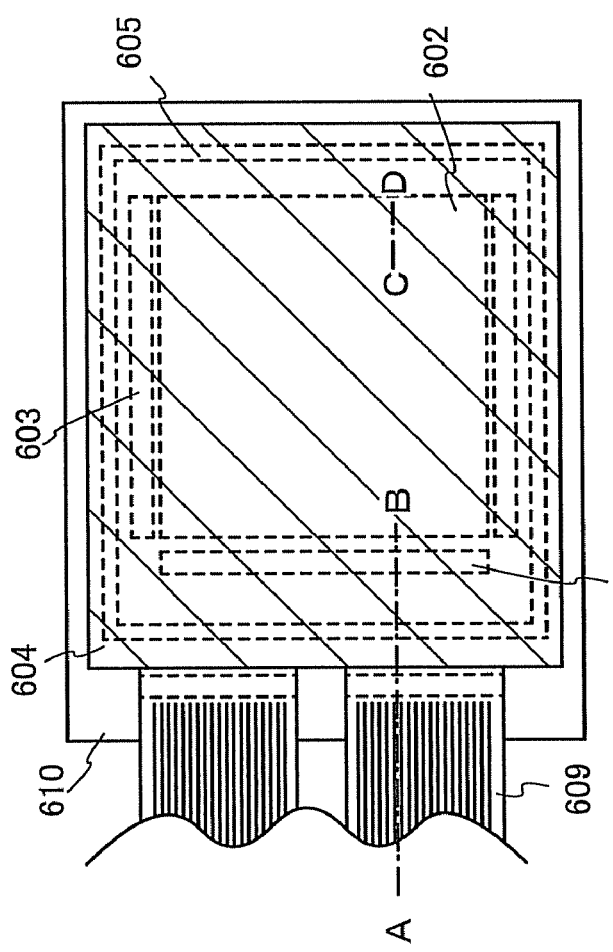
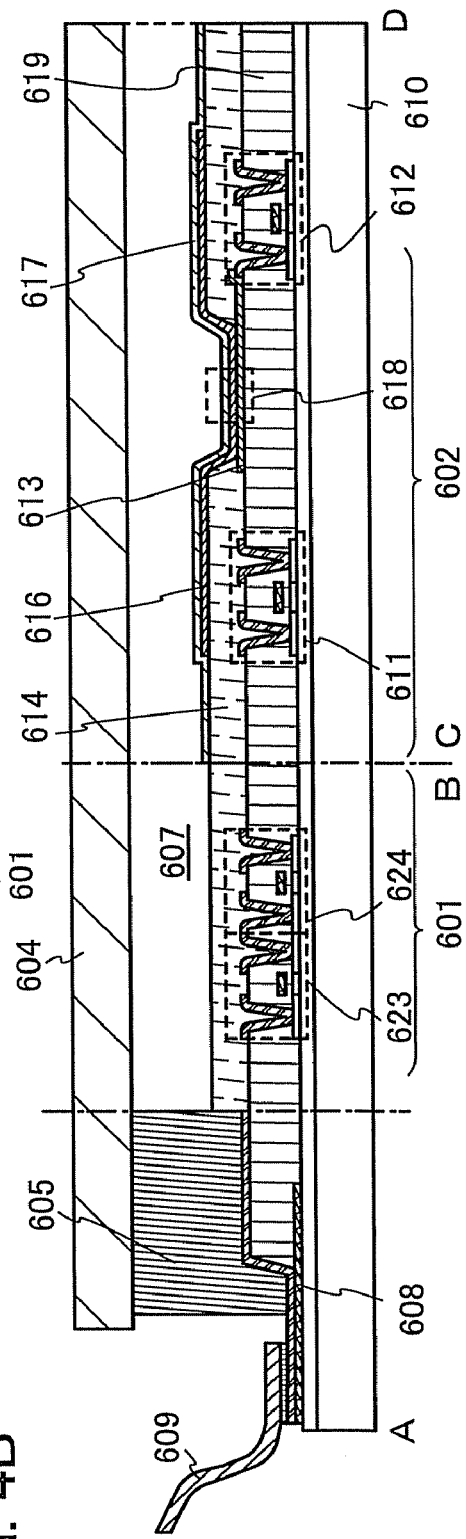
FIG. 4A
FIG. 4B

OXADIAZOLE DERIVATIVE, LIGHT-EMITTING ELEMENT MATERIAL, LIGHT-EMITTING ELEMENT, LIGHT-EMITTING DEVICE, AND ELECTRONIC DEVICE

BACKGROUND OF THE INVENTION

1. Field of the Invention

The present invention relates to oxadiazole derivatives. In addition, the present invention relates to light-emitting element materials, light-emitting elements, and electronic devices each using the oxadiazole derivative.

2. Description of the Related Art

An organic compound can take a wider variety of structures compared with an inorganic compound, and it is possible to synthesize a material having various functions by appropriate molecular design of an organic compound. Owing to those advantages, electronics utilizing a functional organic material has been attracting attention in recent years.

For example, a solar cell, a light-emitting element, an organic transistor, and the like are exemplified as electronic devices utilizing an organic compound as a functional material. These are devices taking advantage of electric properties and optical properties of the organic compound. Among them, in particular, a light-emitting element has been making remarkable development.

It is considered that light emission mechanism of a light-emitting element is as follows: when a voltage is applied between a pair of electrodes between which a light-emitting layer is interposed, electrons injected from a cathode and holes injected from an anode are recombined in the light-emission center of the light-emitting layer to form a molecular exciton, and energy is released to emit light when the molecular exciton relaxes to a ground state. Singlet excitation and triplet excitation are known as excited states, and light emission can probably be achieved through either of the excited states.

Such a light-emitting element has a lot of problems which depend on the organic materials. In order to solve these problems, improvement of an element structure, development of a material, and the like have been carried out.

As the most basic structure of a light-emitting element, the following structure is known: a hole-transporting layer including an organic compound having a hole-transporting property and an electron-transporting light-emitting layer including an organic compound having an electron-transporting property are stacked to form a thin film of approximately 100 nm thickness in total, and this thin film is interposed between electrodes (see Non-Patent Document 1, for example).

When a voltage is applied to the light-emitting element described in Non-Patent Document 1, light emission can be obtained from the organic compound having a light-emitting property and an electron-transporting property.

Further, in the light-emitting element described in Non-Patent Document 1, functions are separated as appropriate so that the hole-transporting layer transports holes whereas the electron-transporting layer transports electrons and emits light. However, various interactions (e.g., exciplex formation) frequently occur at an interface of the stacked layers. As a result, changes in the emission spectrum or reduction in emission efficiency may occur.

In order to suppress the changes in the emission spectrum or the reduction in emission efficiency, which are caused by the interactions at the interface, a light-emitting element having further functional separation has been developed. For example, a light-emitting element has been proposed, in which a light-emitting layer is interposed between a hole-transporting layer and an electron-transporting layer (see Non-Patent Document 2, for example).

In such a light-emitting element described in Non-Patent Document 2, in order to more effectively suppress the interaction occurring at the interface, it is preferable that the light-emitting layer be formed to include a bipolar organic compound having both an electron-transporting property and a hole-transporting property.

However, most organic compounds are monopolar materials having either a hole-transporting property or an electron-transporting property.

Therefore, bipolar organic compounds having both an electron-transporting property and a hole-transporting property should be developed.

REFERENCE

Non-Patent Document

[Non-Patent Document 1] C. W. Tang et al., Applied Physics Letters, vol. 51, No. 12, 913-915 (1987)

[Non-Patent Document 2] Chihaya Adachi et al., Japanese Journal of Applied Physics, vol. 27, No. 2, L269-L271 (1988)

SUMMARY OF THE INVENTION

In view of the above-described situation, it is an object of an embodiment of the present invention to provide a novel material having a bipolar property.

Further, an object of an embodiment of the present invention is to provide an oxadiazole derivative having a wide band gap.

Furthermore, an object of an embodiment of the present invention is to reduce power consumption of a light-emitting element, a light-emitting device, and an electronic device.

An embodiment of the present invention is an oxadiazole derivative represented by General Formula (1).

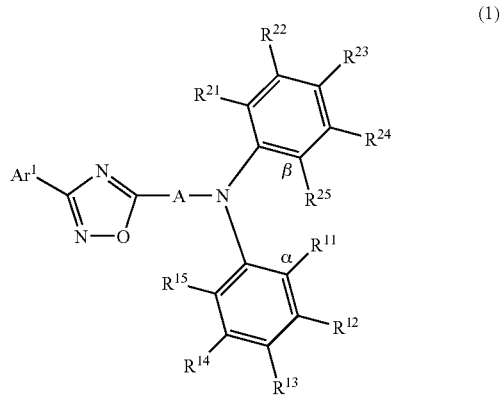

In the formula, $Ar^1$ represents a substituted or unsubstituted aryl group having 6 to 10 carbon atoms in a ring. A represents a substituted or unsubstituted phenylene group. $R^{11}$ to $R^{15}$ and $R^{21}$ to $R^{25}$ are independently any of hydrogen, an alkyl group having 1 to 4 carbon atoms, an aryl group having 6 to 10 carbon atoms in a ring, or a substituted or unsubstituted 9H-carbazol-9-yl group. A substituent of $Ar^1$ may be an alkyl group having 1 to 4 carbon atoms or an aryl group having 6 to 10 carbon atoms in a ring, and a substituent of A may be an alkyl group having 1 to 4 carbon atoms. A substituent of the 9H-carbazol-9-yl group may be an alkyl group having 1 to 4 carbon atoms or an aryl group having 6 to 10 carbon atoms in a ring. Further, carbon at α position and carbon at β position may be bonded to each other to form a carbazole ring.

Another embodiment of the present invention is an oxadiazole derivative represented by General Formula (2).

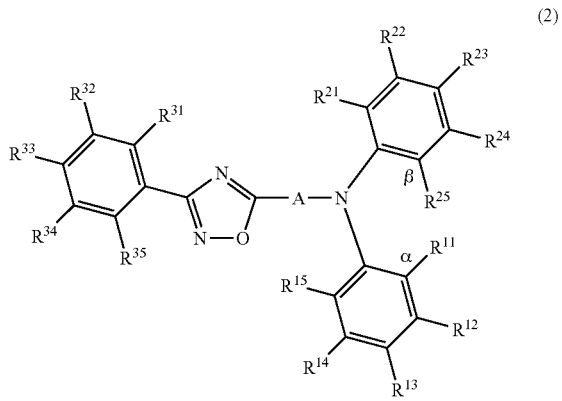

(2)

In the formula, A represents a substituted or unsubstituted phenylene group. $R^{11}$ to $R^{15}$ and $R^{21}$ to $R^{25}$ are independently any of hydrogen, an alkyl group having 1 to 4 carbon atoms, an aryl group having 6 to 10 carbon atoms in a ring, or a substituted or unsubstituted 9H-carbazol-9-yl group. $R^{31}$ to $R^{35}$ are independently any of hydrogen, an alkyl group having 1 to 4 carbon atoms, or an aryl group having 6 to 10 carbon atoms in a ring. Further, a substituent of A may be an alkyl group having 1 to 4 carbon atoms. A substituent of the 9H-carbazol-9-yl group may be an alkyl group having 1 to 4 carbon atoms or an aryl group having 6 to 10 carbon atoms in a ring. Further, carbon at α position and carbon at β position may be bonded to each other to form a carbazole ring.

Another embodiment of the present invention is an oxadiazole derivative represented by General Formula (3).

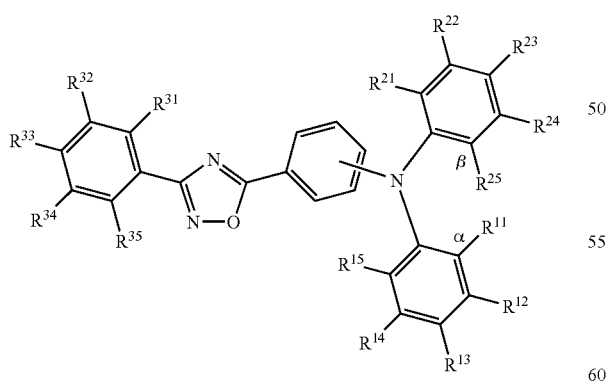

(3)

In the formula, $R^{11}$ to $R^{15}$ and $R^{21}$ to $R^{25}$ are independently any of hydrogen, an alkyl group having 1 to 4 carbon atoms, an aryl group having 6 to 10 carbon atoms in a ring, or a substituted or unsubstituted 9H-carbazol-9-yl group. $R^{31}$ to $R^{35}$ are independently any of hydrogen, an alkyl group having 1 to 4 carbon atoms, or an aryl group having 6 to 10 carbon atoms in a ring. A substituent of the 9H-carbazol-9-yl group may be an alkyl group having 1 to 4 carbon atoms or an aryl group having 6 to 10 carbon atoms in a ring. Further, carbon at α position and carbon at β position may be bonded to each other to form a carbazole ring.

Another embodiment of the present invention is an oxadiazole derivative represented by General Formula (4).

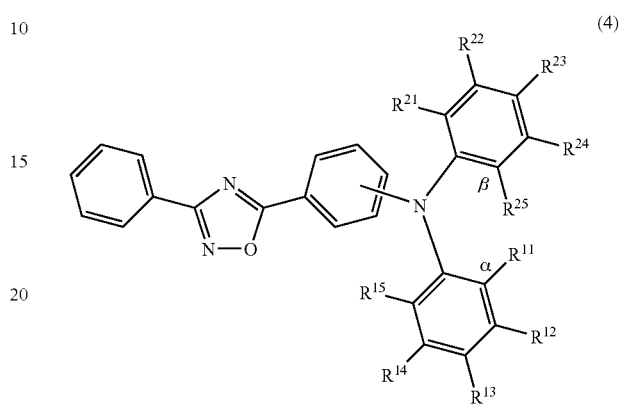

(4)

In the formula, $R^{11}$ to $R^{15}$ and $R^{21}$ to $R^{25}$ are independently any of hydrogen, an alkyl group having 1 to 4 carbon atoms, an aryl group having 6 to 10 carbon atoms in a ring, or a substituted or unsubstituted 9H-carbazol-9-yl group. A substituent of the 9H-carbazol-9-yl group may be an alkyl group having 1 to 4 carbon atoms or an aryl group having 6 to 10 carbon atoms in a ring. Further, carbon at α position and carbon at β position may be bonded to each other to form a carbazole ring.

Another embodiment of the present invention is an oxadiazole derivative represented by General Formula (5).

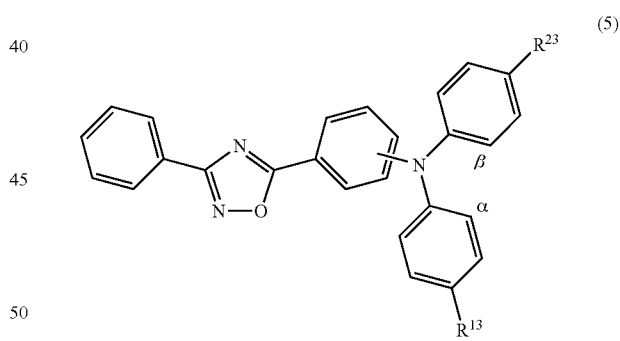

(5)

In the formula, $R^{13}$ and $R^{23}$ are independently hydrogen or an unsubstituted 9H-carbazol-9-yl group. Further, carbon at α position and carbon at β, position may be bonded to each other to form a carbazole ring.

Still another embodiment of the present invention is a light-emitting element which includes any of the above-described oxadiazole derivatives, and specifically a light-emitting element which includes any of the above-described oxadiazole derivatives between a pair of electrodes.

Another embodiment of the present invention is a light-emitting element including a light-emitting layer between a pair of electrodes, and the light-emitting layer includes any of the above-described oxadiazole derivatives.

Yet another embodiment of the present invention is a light-emitting device which includes a light-emitting element including a layer containing a light-emitting substance between a pair of electrodes and a control unit for controlling light emission of the light-emitting element. The layer containing a light-emitting substance includes any of the above-described oxadiazole derivatives. Note that the term "light-emitting device" in this specification includes image display devices, light-emitting devices, and light sources (including lighting device). Further, the term "light-emitting device" also includes any of the following modules in its category: a module including a panel provided with a connector such as a flexible printed circuit (FPC), tape automated bonding (TAB) tape, or a tape carrier package (TCP); a module having TAB tape or a TCP which is provided with a printed wiring board at the end thereof; and a module having an integrated circuit (IC) which is directly mounted on a light-emitting element by a chip on glass (COG) method.

Further, the present invention also includes, in its category, an electronic device which includes an embodiment of the light-emitting element of the present invention in a display portion. Accordingly, an embodiment of an electronic device of the present invention includes a display portion including any of the above-described light-emitting element and a control unit for controlling light emission of the light-emitting element.

An embodiment of the present invention is an oxadiazole derivative which is a bipolar material which allows both a hole and an electron to flow.

Furthermore, an oxadiazole derivative according to an embodiment of the present invention can be used as either a light-emitting material (including a dopant) or a host material in a light-emitting layer of a light-emitting element.

Since an embodiment of the oxadiazole derivative of the present invention has a large band gap, in the case of a light-emitting element including a light-emitting layer in which the oxadiazole derivative is used as a host material, light emission not from the oxadiazole derivative but from a dopant can be obtained efficiently.

With the use of an embodiment of the oxadiazole derivative of the present invention, a light-emitting element, a light-emitting device, and an electronic device with lower power consumption can be provided.

BRIEF DESCRIPTION OF THE DRAWINGS

In the accompanying drawings:

FIGS. 4A and 4B are views illustrating a light-emitting device;

DETAILED DESCRIPTION OF THE INVENTION

Figure 1A:
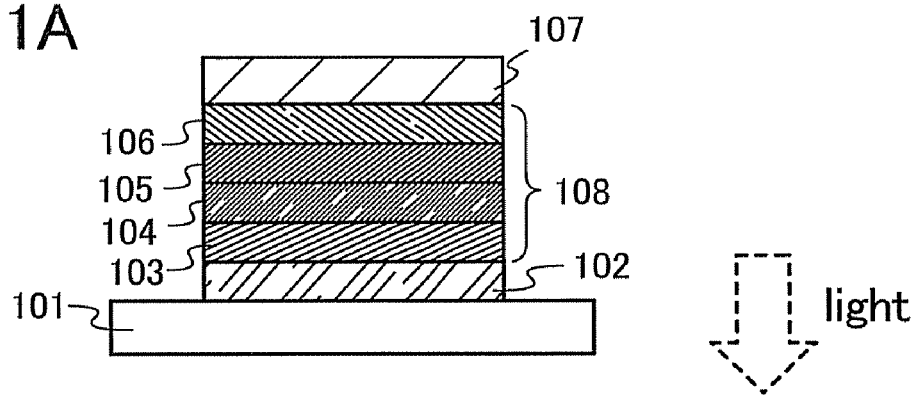
FIGS. 1A to 1C are views each illustrating a light-emitting element.

Hereinafter, embodiments of the present invention will be described in detail with reference to the accompanying drawings. The present invention is not limited to the following description of the embodiments. It is easily understood by those skilled in the art that modes and details of the present invention can be changed in various ways without departing from the spirit and scope of the present invention. Therefore, the present invention is not construed as being limited to description of the embodiments below.

Embodiment 1

In this embodiment, embodiments of an oxadiazole derivative of the present invention will be described.

An oxadiazole derivative according to this embodiment is an oxadiazole derivative represented by General Formula (1).

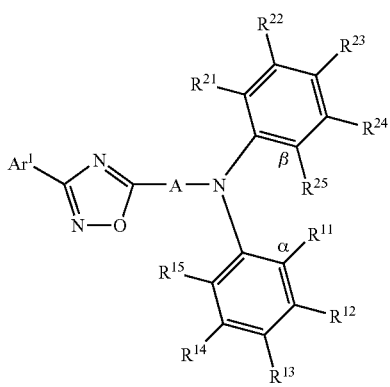

(1)

In the formula, $Ar^1$ represents a substituted or unsubstituted aryl group having 6 to 10 carbon atoms in a ring. A represents a substituted or unsubstituted phenylene group. $R^{11}$ to $R^{15}$ and $R^{21}$ to $R^{25}$ are independently any of hydrogen, an alkyl group having 1 to 4 carbon atoms, an aryl group having 6 to 10 carbon atoms in a ring, or a substituted or unsubstituted 9H-carbazol-9-yl group. A substituent of $Ar^1$ may be an alkyl group having 1 to 4 carbon atoms or an aryl group having 6 to 10 carbon atoms in a ring, and a substituent of A may be an alkyl group having 1 to 4 carbon atoms. A substituent of the 9H-carbazol-9-yl group may be an alkyl group having 1 to 4 carbon atoms or an aryl group having 6 to 10 carbon atoms in a ring. Further, carbon at α position and carbon at β position may be bonded to each other to form a carbazole ring.

An oxadiazole derivative according to this embodiment is an oxadiazole derivative represented by General Formula (2).

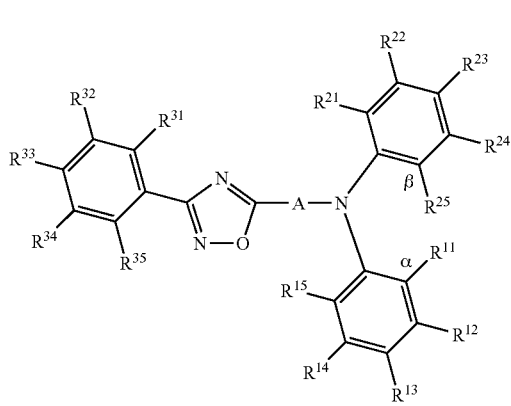

(2)

In the formula, A represents a substituted or unsubstituted phenylene group. $R^{11}$ to $R^{15}$ and $R^{21}$ to $R^{25}$ are independently any of hydrogen, an alkyl group having 1 to 4 carbon atoms, an aryl group having 6 to 10 carbon atoms in a ring, or a substituted or unsubstituted 9H-carbazol-9-yl group. $R^{31}$ to $R^{35}$ are independently any of hydrogen, an alkyl group having 1 to 4 carbon atoms, or an aryl group having 6 to 10 carbon atoms in a ring. Further, a substituent of A may be an alkyl group having 1 to 4 carbon atoms, and a substituent of the 9H-carbazol-9-yl group may be an alkyl group having 1 to 4 carbon atoms or an aryl group having 6 to 10 carbon atoms in a ring. Further, carbon at α position and carbon at β position may be bonded to each other to form a carbazole ring.

An oxadiazole derivative according to this embodiment is an oxadiazole derivative represented by General Formula (3).

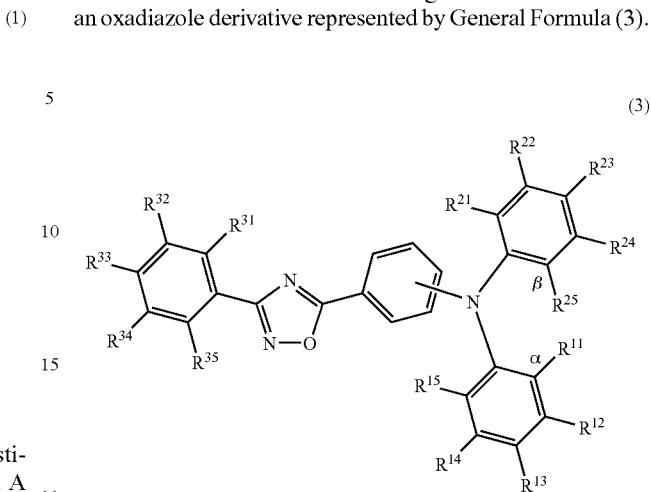

(3)

In the formula, $R^{11}$ to $R^{15}$ and $R^{21}$ to $R^{25}$ are independently any of hydrogen, an alkyl group having 1 to 4 carbon atoms, an aryl group having 6 to 10 carbon atoms in a ring, or a substituted or unsubstituted 9H-carbazol-9-yl group. $R^{31}$ to $R^{35}$ are independently any of hydrogen, an alkyl group having 1 to 4 carbon atoms, or an aryl group having 6 to 10 carbon atoms in a ring. A substituent of the 9H-carbazol-9-yl group may be an alkyl group having 1 to 4 carbon atoms or an aryl group having 6 to 10 carbon atoms in a ring. Further, carbon at α position and carbon at β position may be bonded to each other to form a carbazole ring.

An oxadiazole derivative according to this embodiment is an oxadiazole derivative represented by General Formula (4).

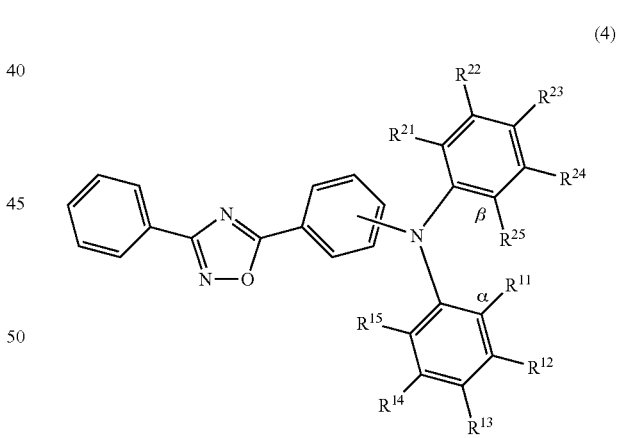

(4)

In the formula, $R^{11}$ to $R^{15}$ and $R^{21}$ to $R^{25}$ are independently any of hydrogen, an alkyl group having 1 to 4 carbon atoms, an aryl group having 6 to 10 carbon atoms in a ring, or a substituted or unsubstituted 9H-carbazol-9-yl group. A substituent of the 9H-carbazol-9-yl group may be an alkyl group having 1 to 4 carbon atoms or an aryl group having 6 to 10 carbon atoms in a ring. Further, carbon at α position and carbon at β position may be bonded to each other to form a carbazole ring.

An oxadiazole derivative according to this embodiment is an oxadiazole derivative represented by General Formula (5).

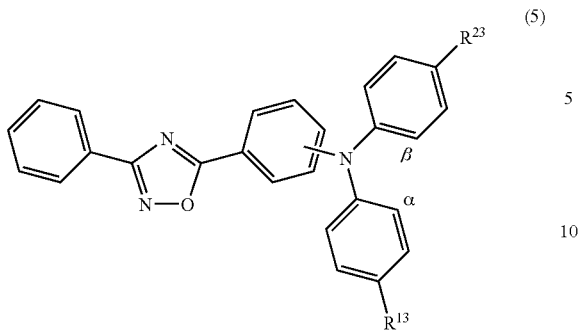
(5)

In the formula, $R^{13}$ and $R^{23}$ are independently hydrogen or an unsubstituted 9H-carbazol-9-yl group. Further, carbon at α position and carbon at β position may be bonded to each other to form a carbazole ring.

Note that the number of carbon atoms of the aryl group or an arylene group in this specification represents the number of carbon atoms which form a ring of the main skeleton, and the number of carbon atoms of a substituent bonded to the main skeleton is not included. A substituent bonded to the aryl group may be an alkyl group having 1 to 4 carbon atoms or an aryl group having 6 to 10 carbon atoms. Specifically, a methyl group, an ethyl group, a propyl group, a butyl group, a phenyl group, a naphthyl group, and the like can be given. As a substituent bonded to the arylene group, an alkyl group having 1 to 4 carbon atoms can be given. Specifically, a methyl group, an ethyl group, a propyl group, a butyl group, and the like can be given. The number of substituents bonded to the aryl group or the arylene group may be either one or plural.

For example, in General Formulae (1) to (5), substituents represented by Structural Formulae (11-1) to (11-21) can be given as specific examples of the group represented by $Ar^1$.

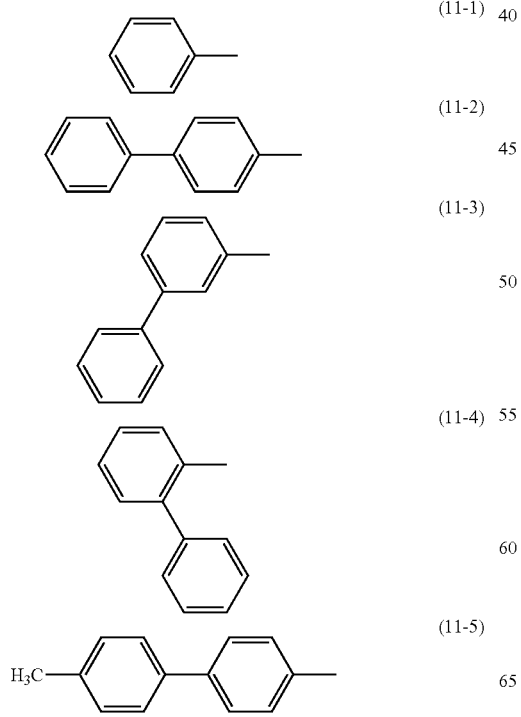

(11-1)
(11-2)
(11-3)
(11-4)
(11-5)

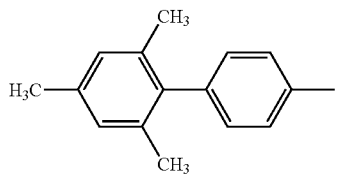
(11-6)

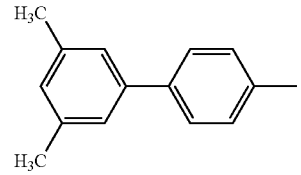
(11-7)

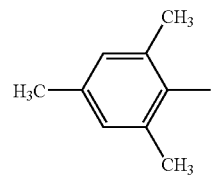
(11-8)

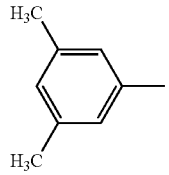
(11-9)

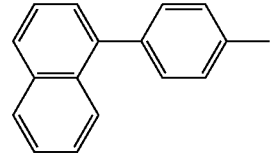
(11-10)

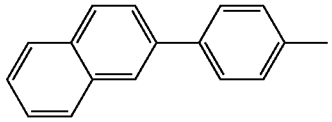
(11-11)

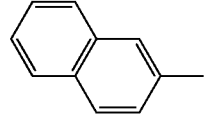
(11-12)

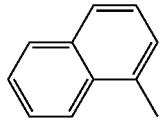
(11-13)

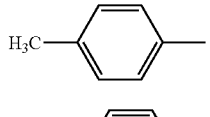
(11-14)

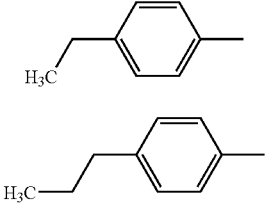
(11-15)

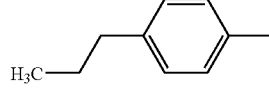
(11-16)

-continued
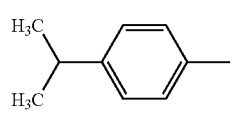 (11-17)
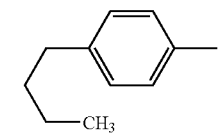 (11-18)
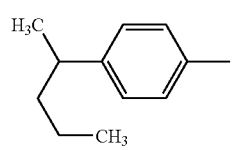 (11-19)
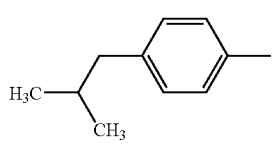 (11-20)
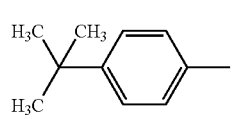 (11-21)
For example, substituents represented by Structural Formulae (12-1) to (12-21) can be given as specific examples of the group represented by A.
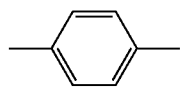 (12-1)
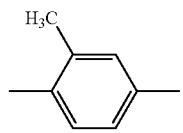 (12-2)
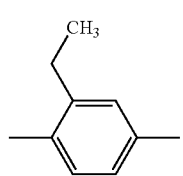 (12-3)
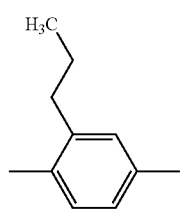 (12-4)
-continued
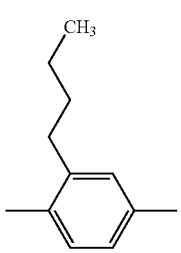 (12-5)
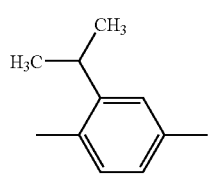 (12-6)
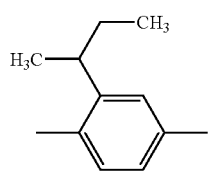 (12-7)
(12-8)
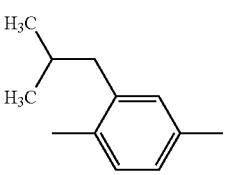 (12-9)
(12-10)
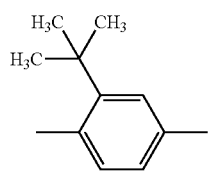 (12-11)
(12-12)
(12-13)

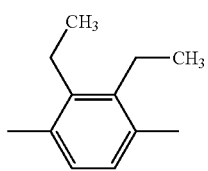 (12-14)
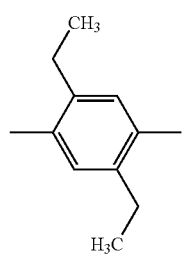 (12-15)
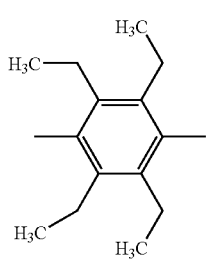 (12-16)
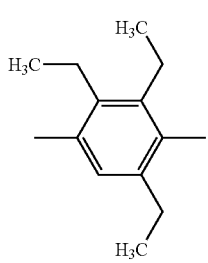 (12-17)
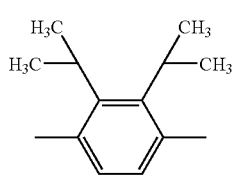 (12-18)
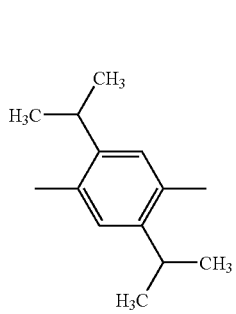 (12-19)
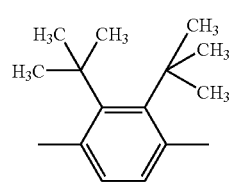 (12-20)
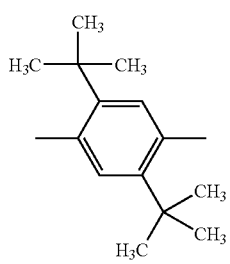 (12-21)
For example, substituents represented by Structural Formulae (13-1) to (13-48) can be given as specific examples of the groups represented by $R^{11}$ to $R^{15}$ and $R^{21}$ to $R^{25}$.
H— (13-1)
H$_3$C— (13-2)
H$_2$C—
H$_3$C (13-3)
H$_2$C—
H$_3$C—CH$_2$ (13-4)
H$_3$C
CH—
H$_3$C (13-5)
H$_2$C
H$_2$C
H$_2$C—CH$_3$ (13-6)
H$_3$C
CH
H$_2$C
CH$_3$ (13-7)
H$_2$C
H$_3$C—CH
CH$_3$ (13-8)
H$_3$C    CH$_3$
C
H$_3$C (13-9)
<image of phenyl group> (13-10)
H$_3$C—<image of p-tolyl group>— (13-11)
H$_3$C—<image of p-ethylphenyl group>— (13-12)

-continued (13-13)
(13-14)
(13-15)
(13-16)
(13-17)
(13-18)
(13-19)
(13-20)
(13-21)
(13-22)
(13-23)

(13-24)
(13-25)
(13-26)
(13-27)
(13-28)
(13-29)

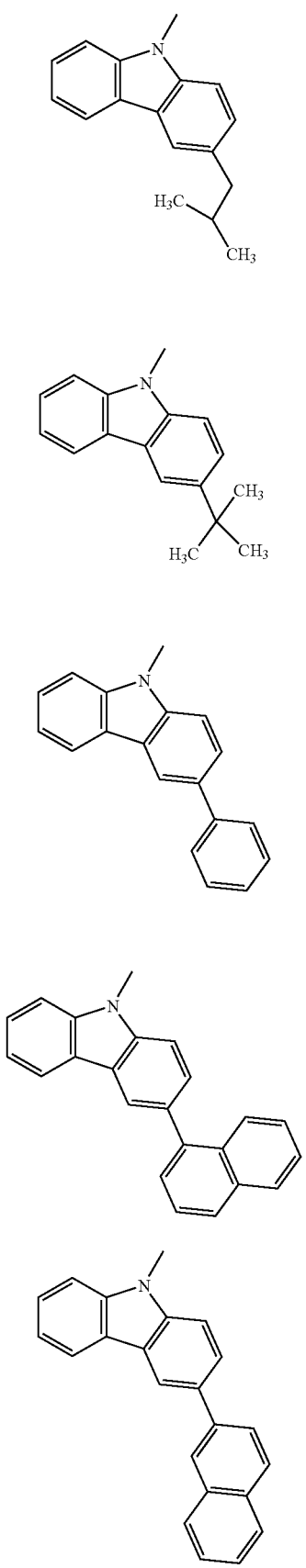
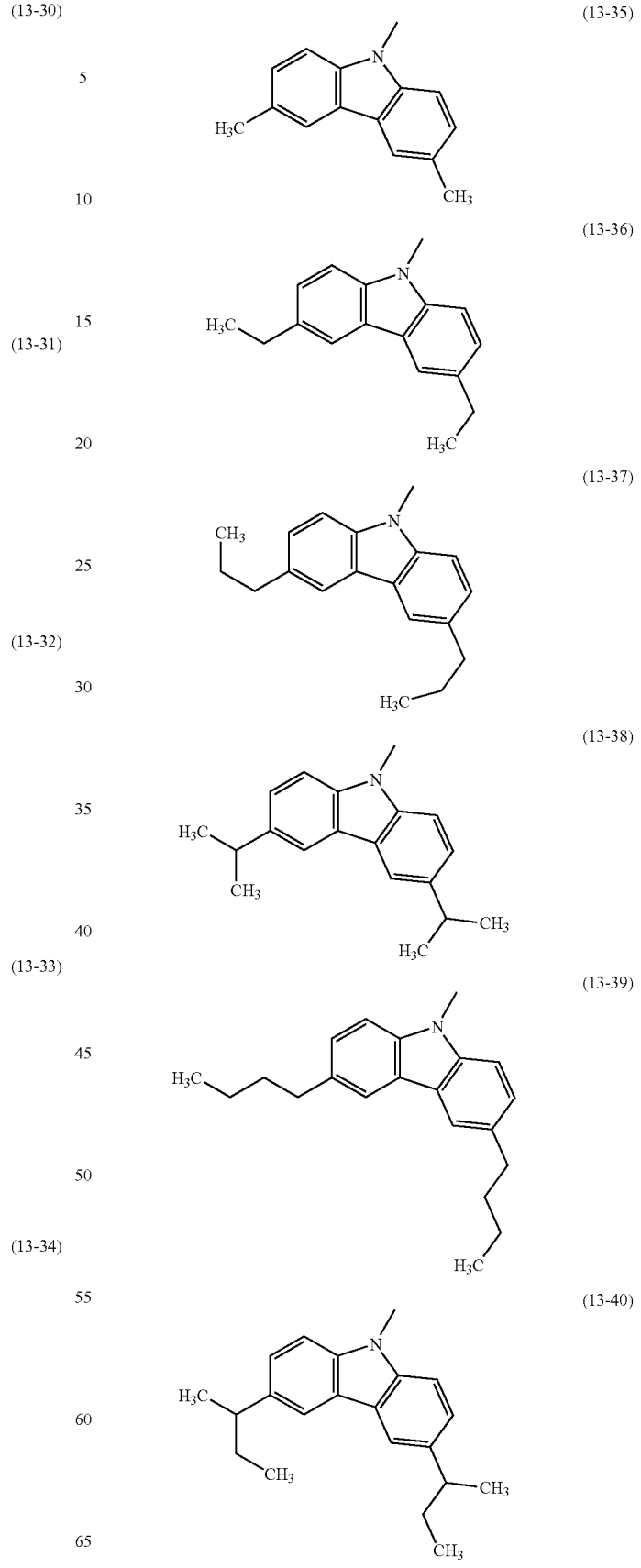

(13-41)
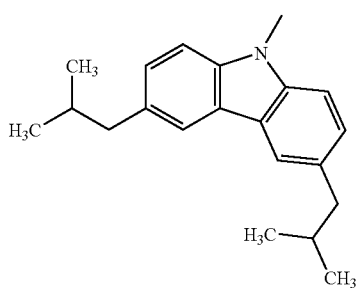
(13-42)
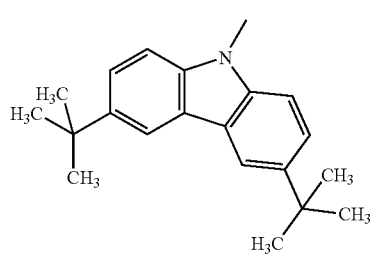
(13-43)
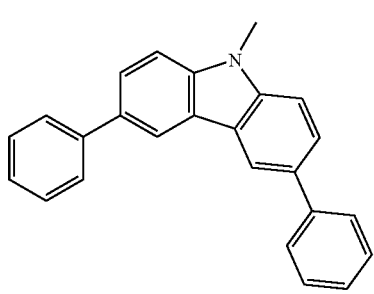
(13-44)
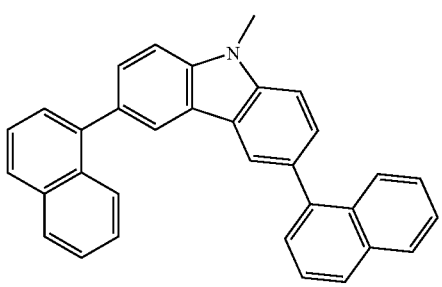
(13-45)
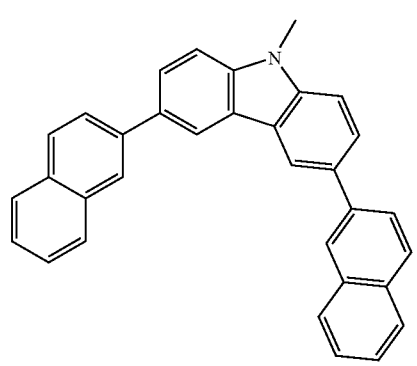
(13-46)
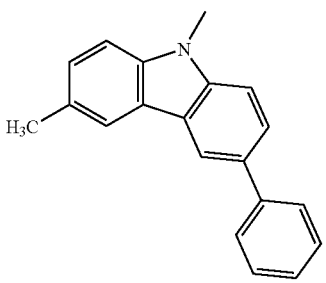
(13-47)
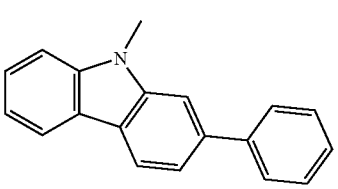
(13-48)
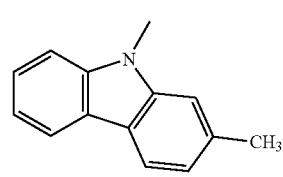
For example, substituents represented by Structural Formulae (14-1) to (14-22) can be given as specific examples of the groups represented by $R^{31}$ to $R^{35}$.
(14-1)
(14-2)
(14-3)
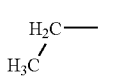
(14-4)
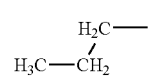
(14-5)
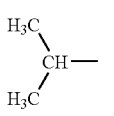
(14-6)
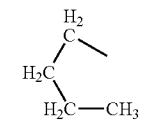
(14-7)
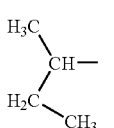
(14-8)
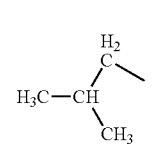

(14-9) 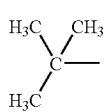
(14-10) 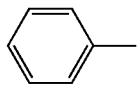
(14-11) 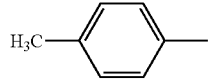
(14-12) 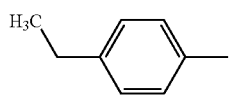
(14-13) 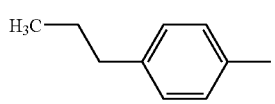
(14-14) 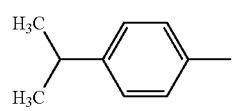
(14-15) 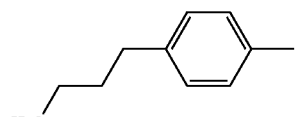
(14-16) 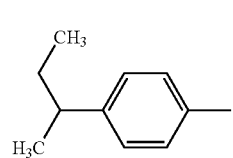
(14-17) 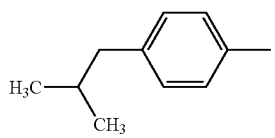
(14-18) 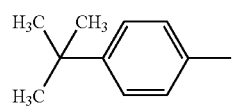
(14-19) 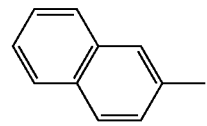
(14-20) 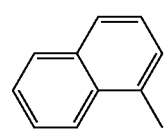
(14-21) 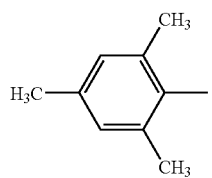
(14-22) 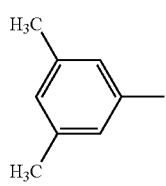
As specific examples of the oxadiazole derivatives represented by General Formulae (1) to (5), oxadiazole derivatives represented by Structural Formulae (100) to (181) can be given. However, the present invention is not limited to these oxadiazole derivatives.
(100) 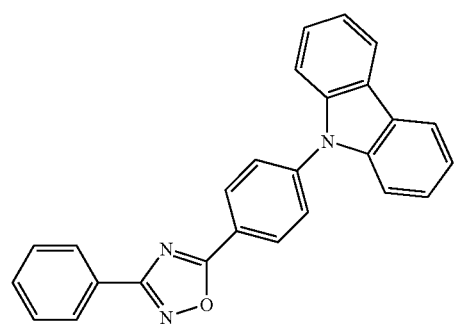
(101) 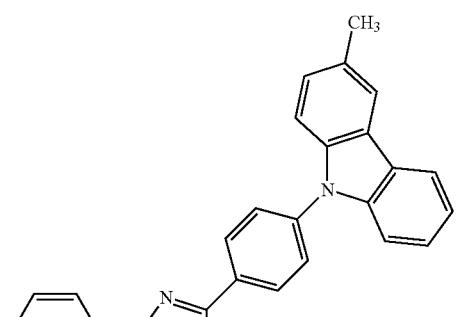
(102) 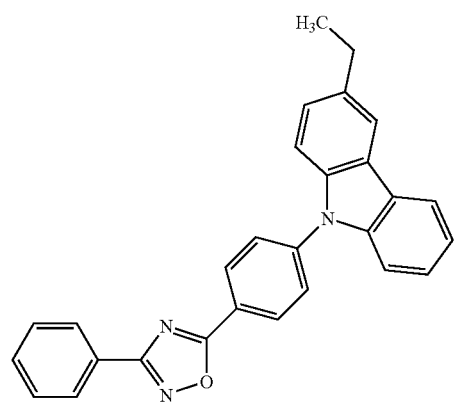

(103)
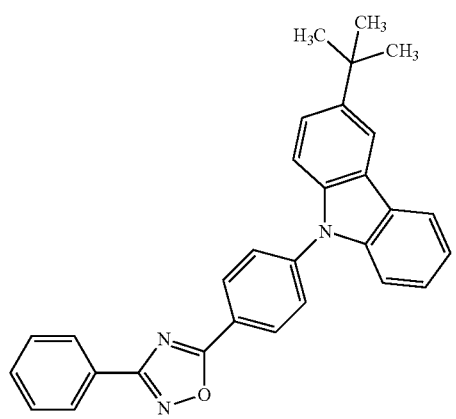
(104)
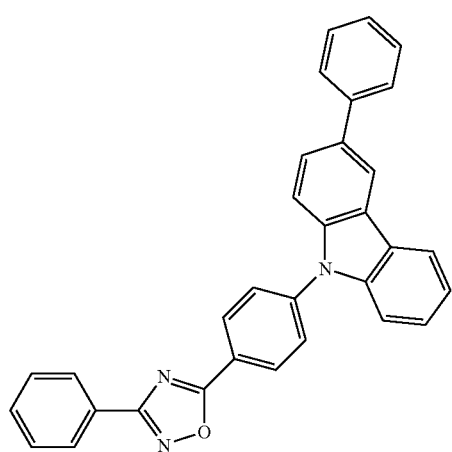
(105)
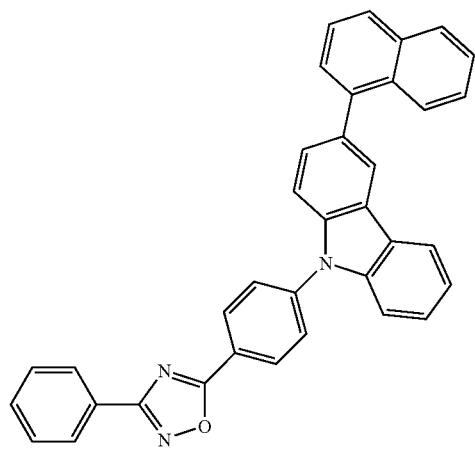
(106)
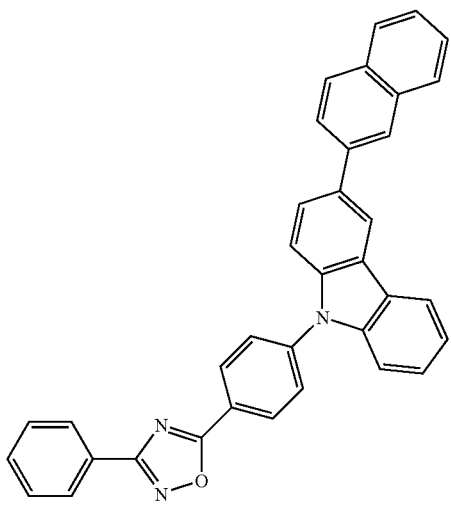
(107)
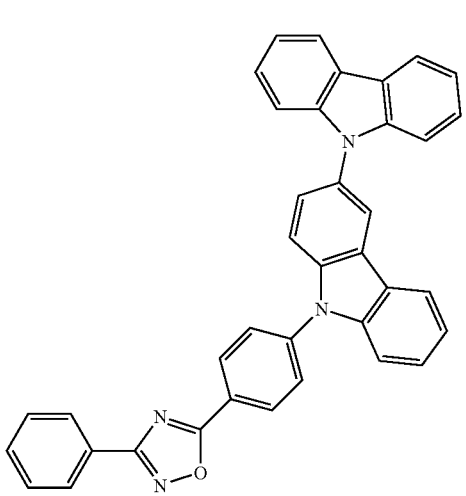
(108)

(109)
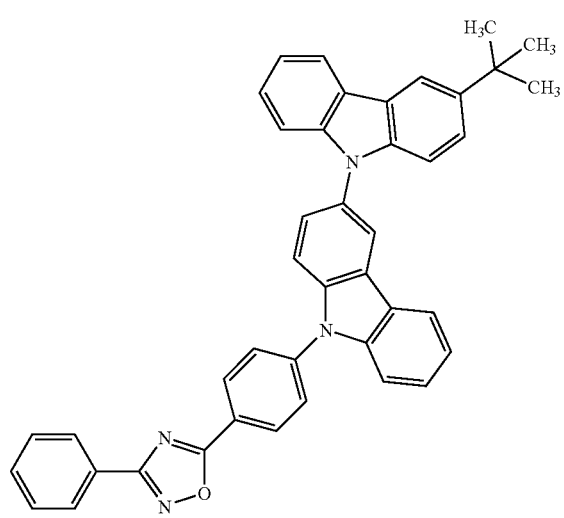
(112)
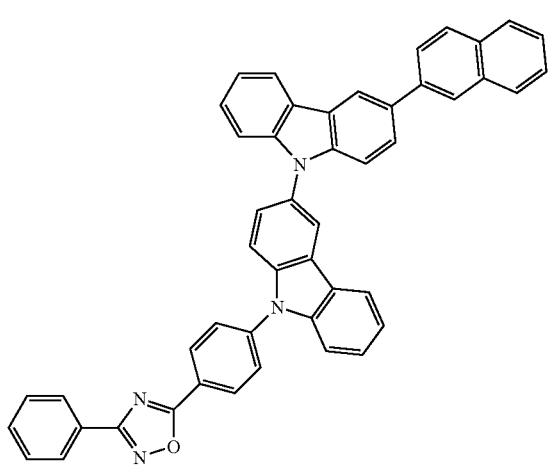
(110)
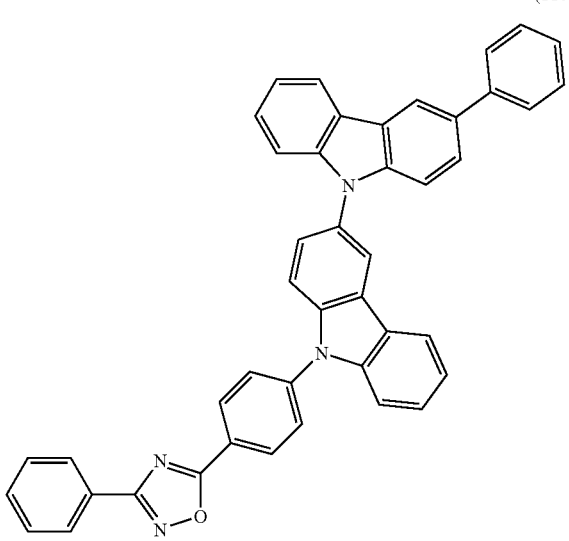
(113)
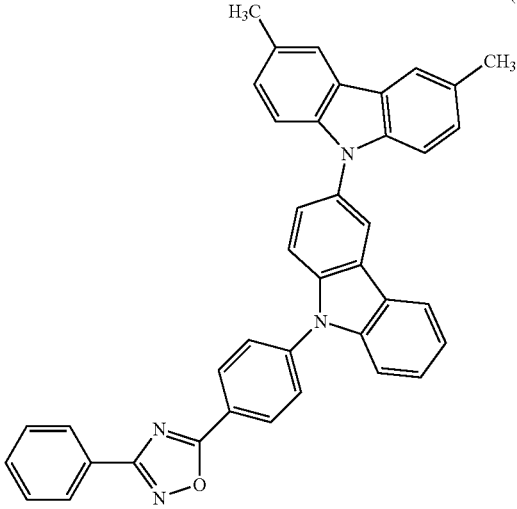
(111)
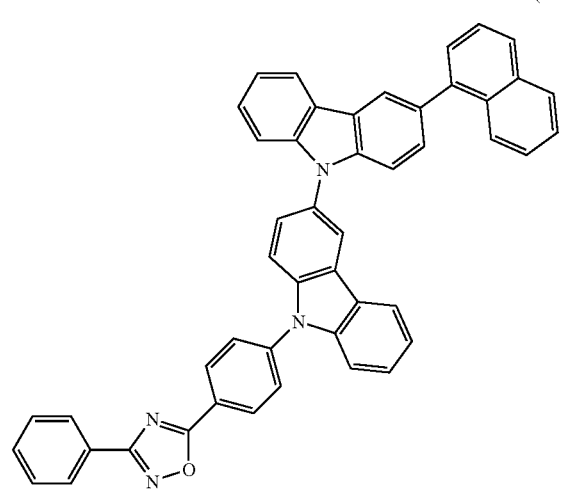
(114)
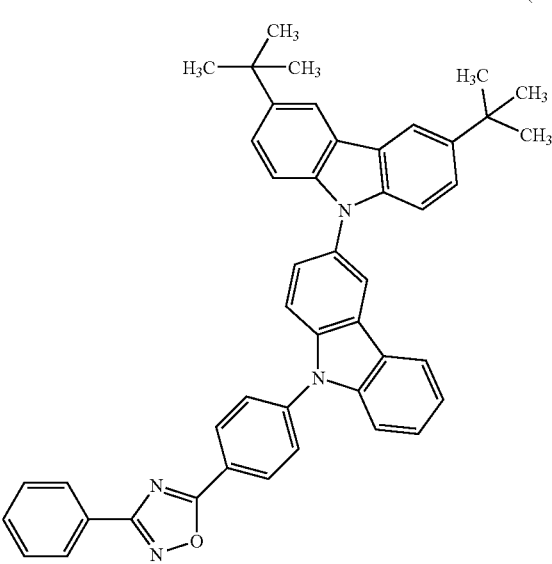

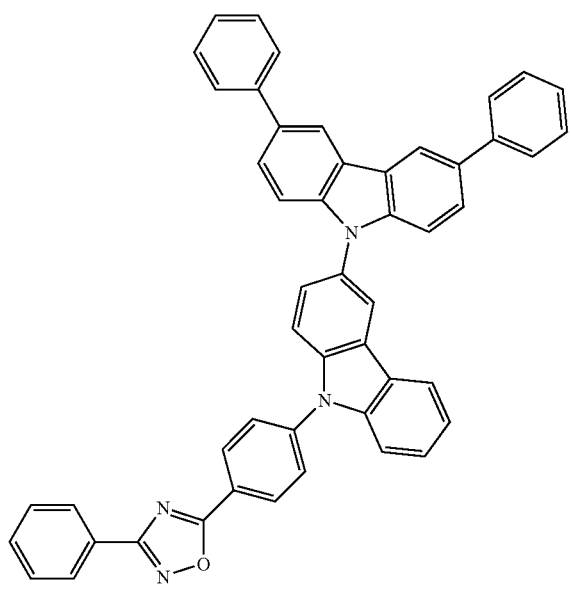
(115)
(116)
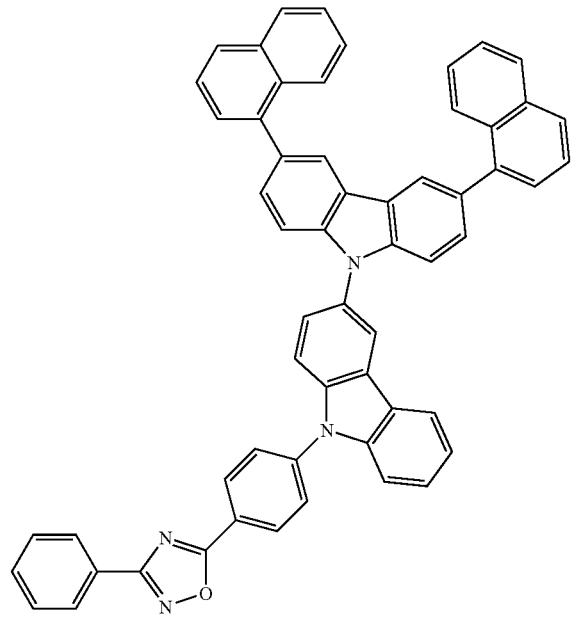
(117)
(118)
(119)

(120)
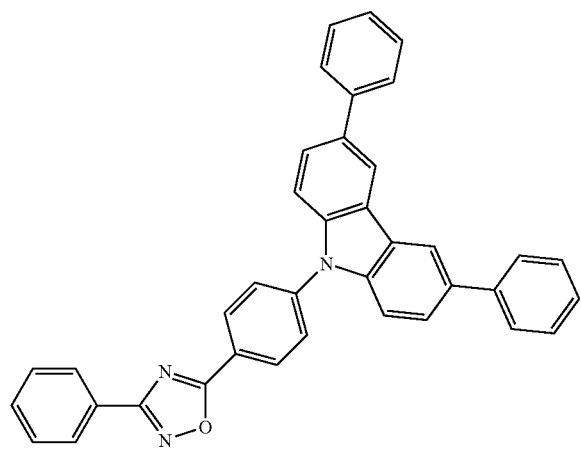
(121)
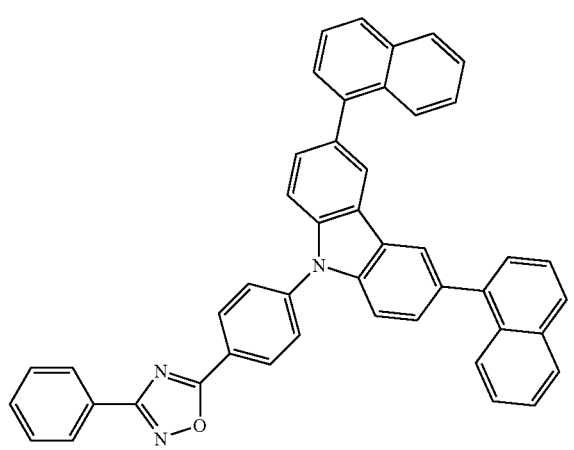
(122)
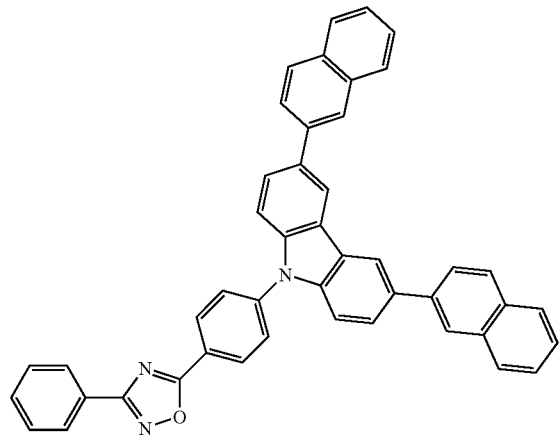
(123)
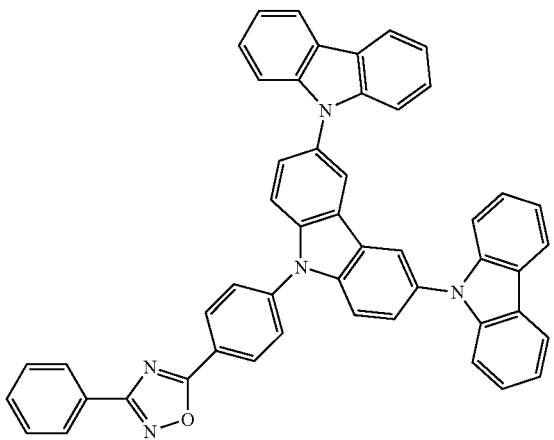
(124)
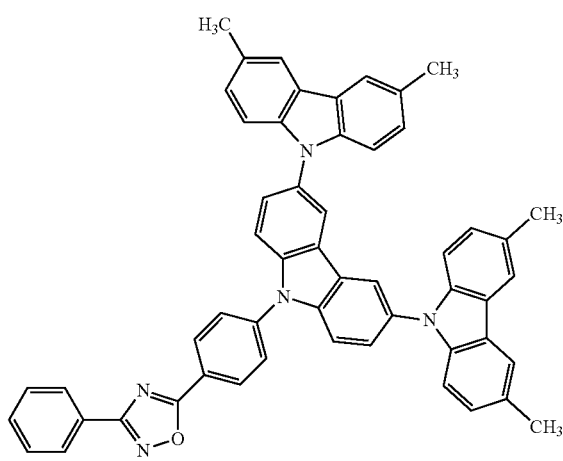
(125)
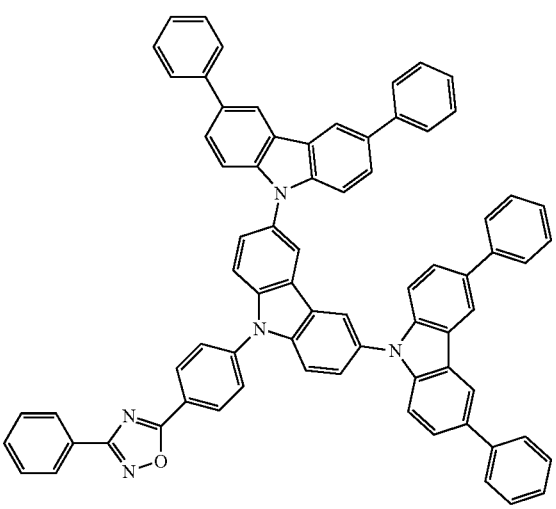

-continued
(126)
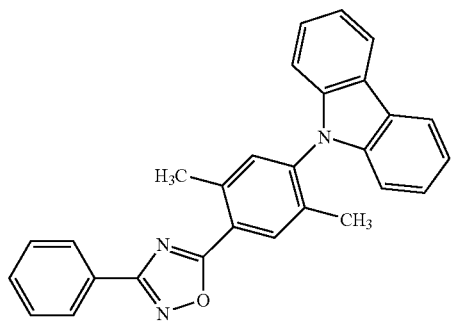
(127)
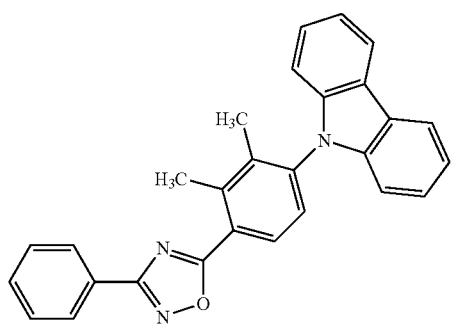
(128)
(129)
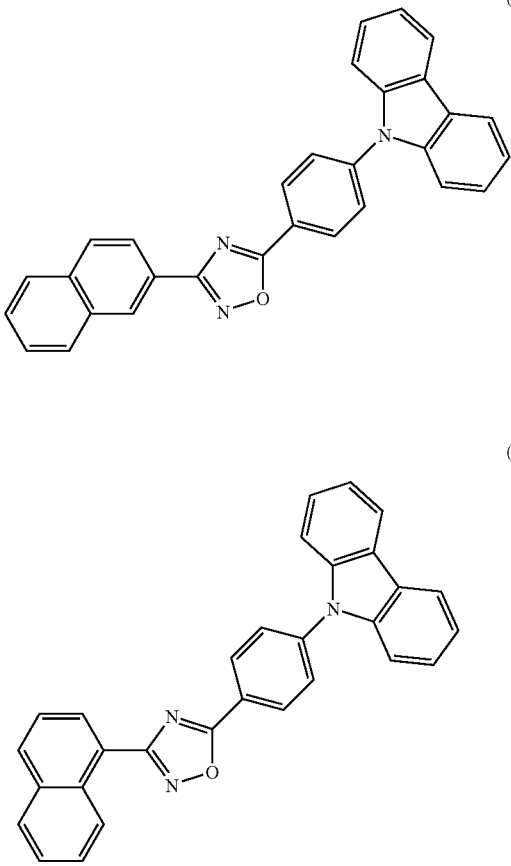
-continued
(130)
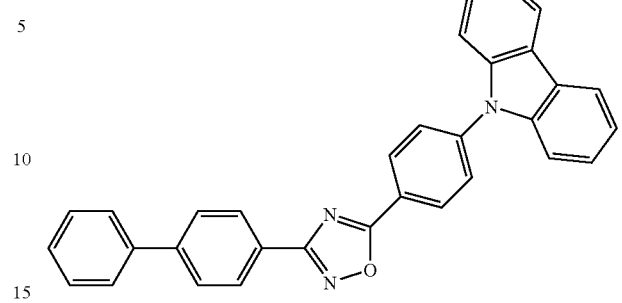
(131)
(132)
(133)
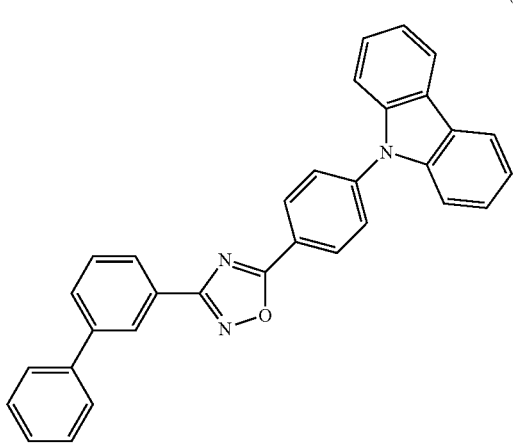

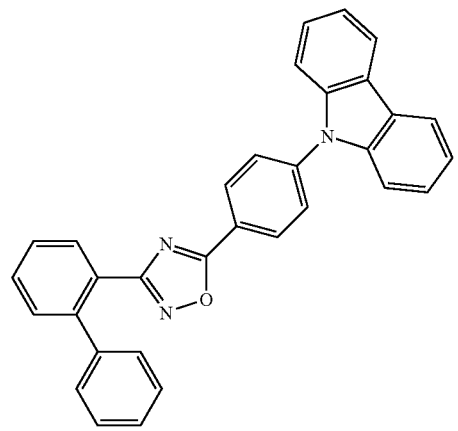
(134)
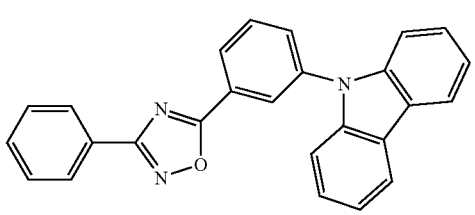
(135)
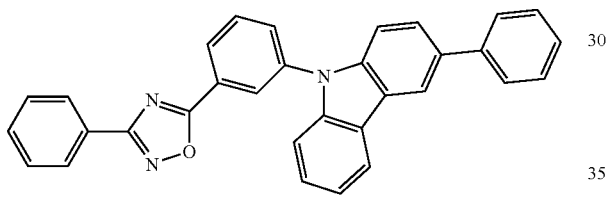
(136)
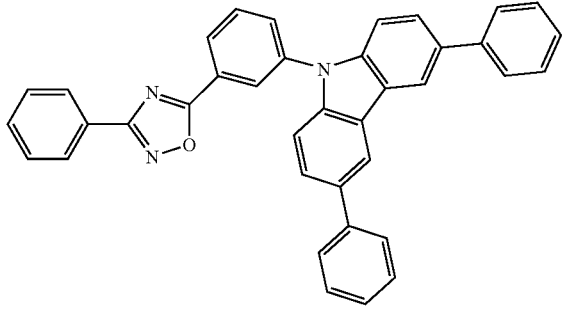
(137)
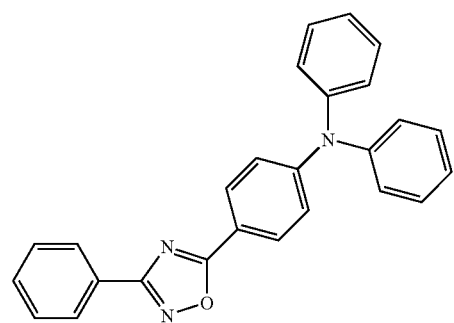
(138)
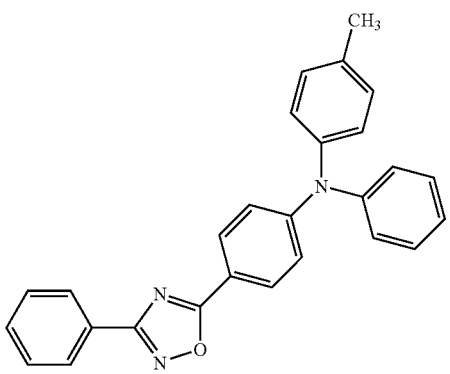
(139)
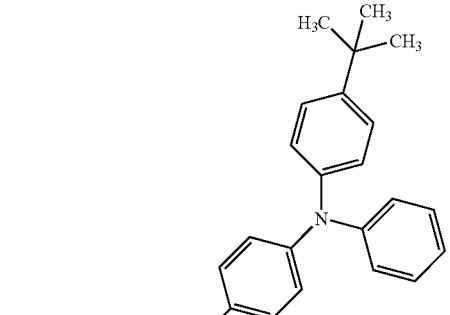
(140)
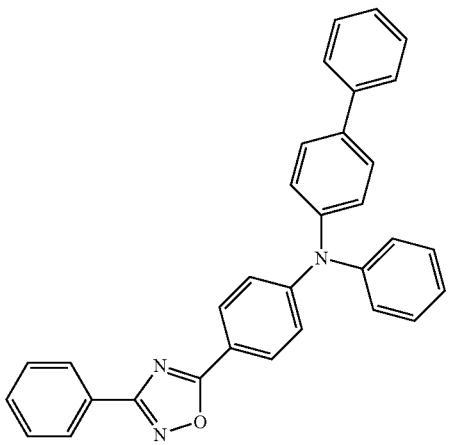
(141)
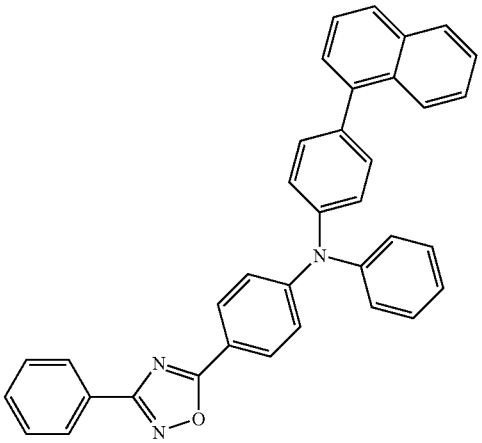
(142)

(143)
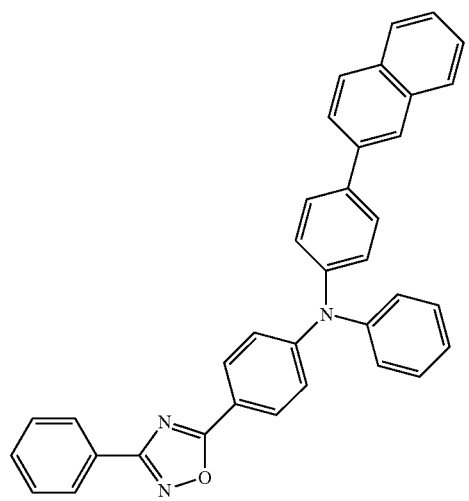
(144)
(145)
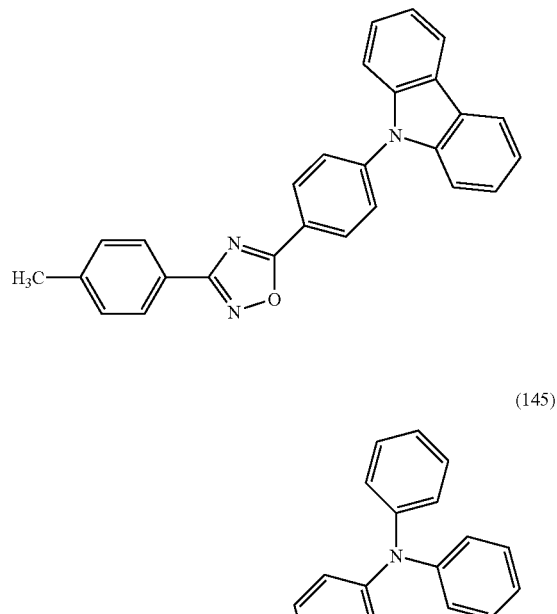
(147)
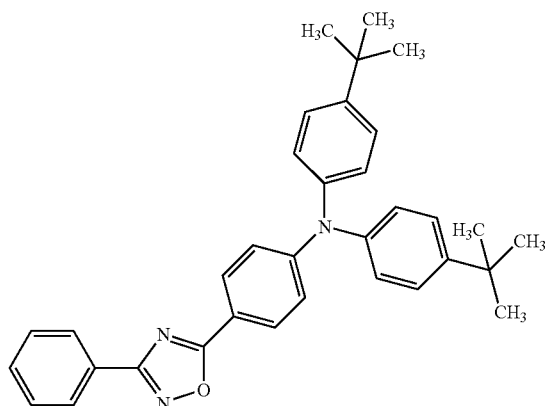
(148)
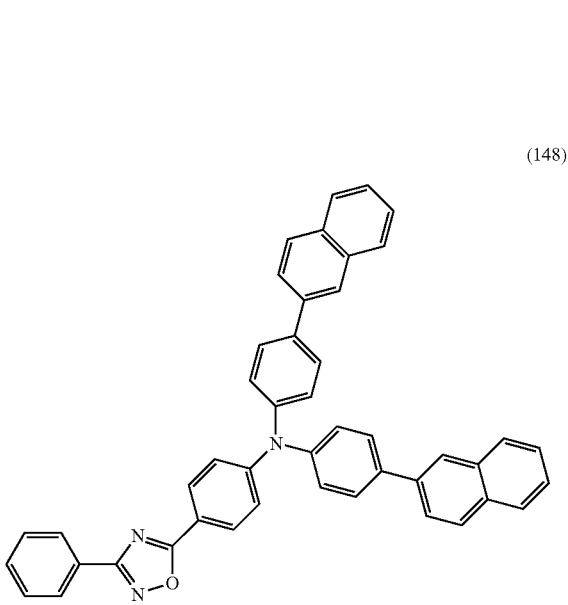
(149)
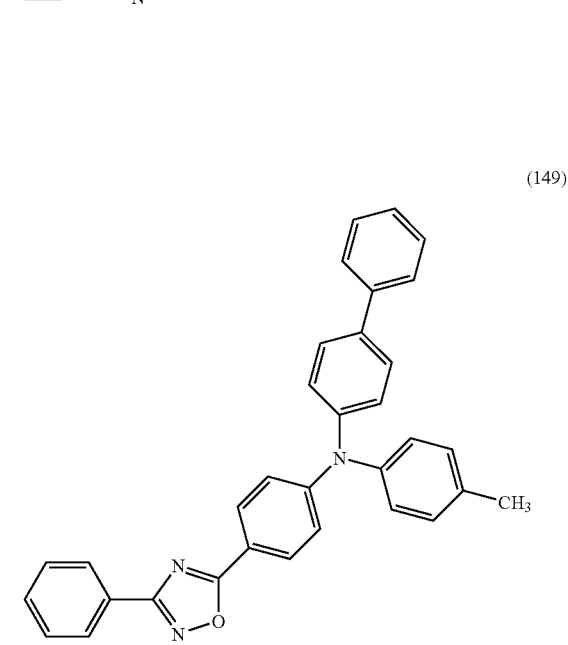

-continued
(150)
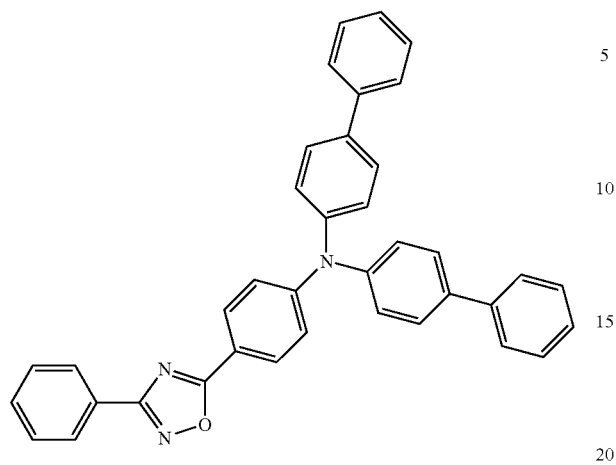
(151)
(152)
-continued
(153)
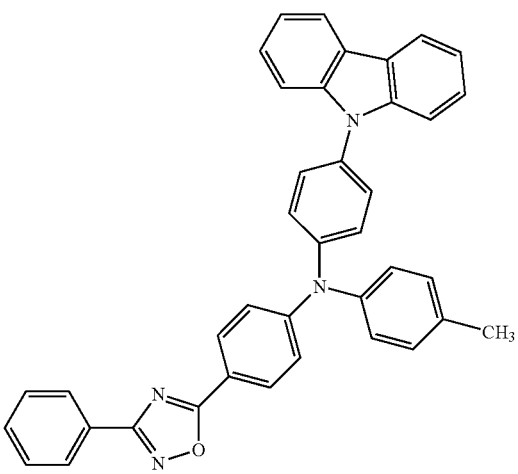
(154)
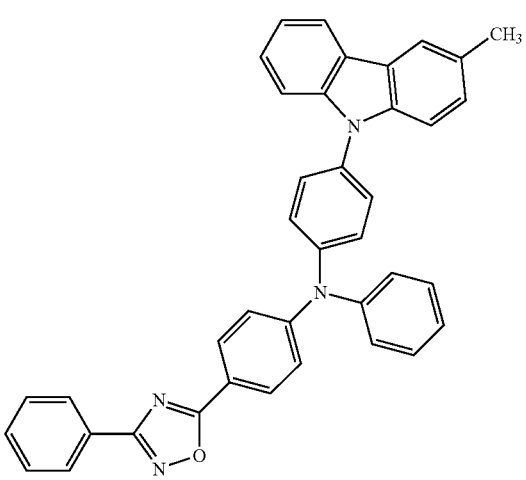
(155)
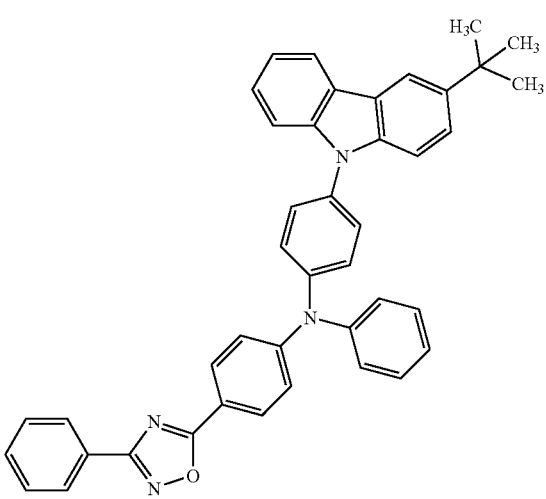

(156)
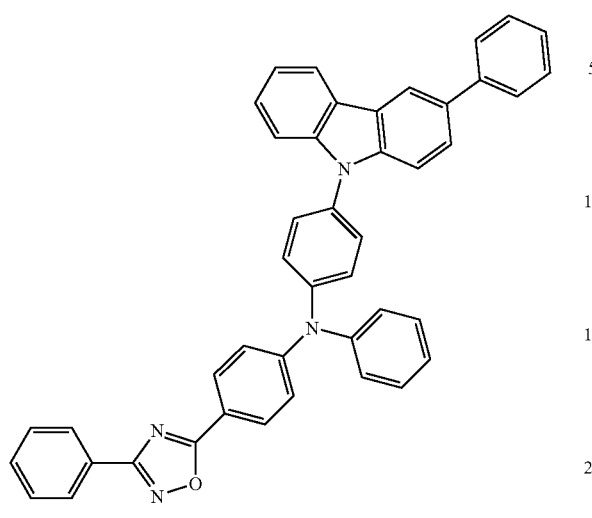
(157)
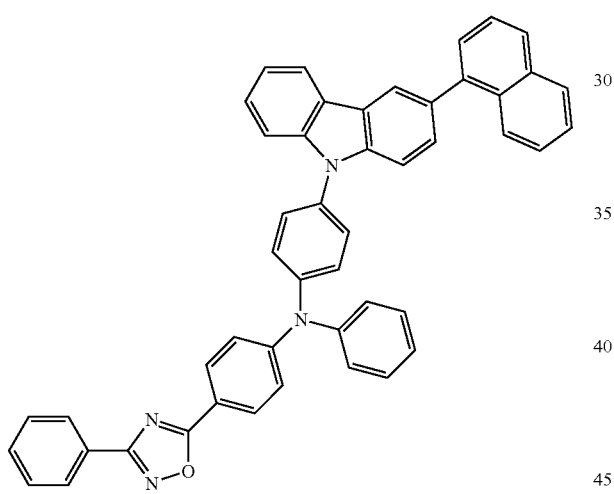
(158)
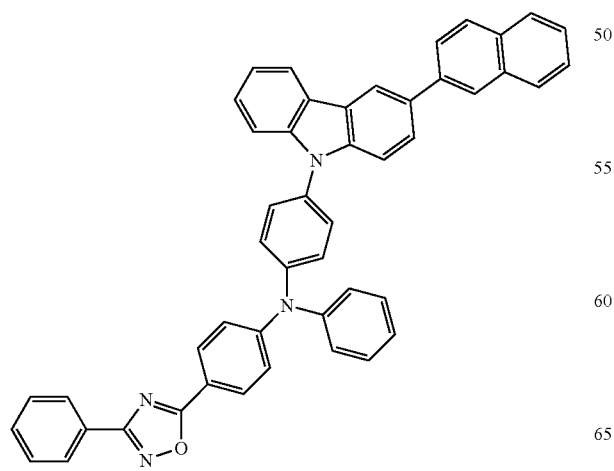
(159)
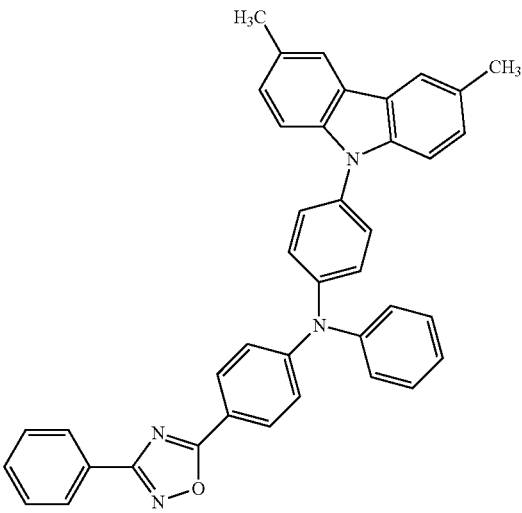
(160)
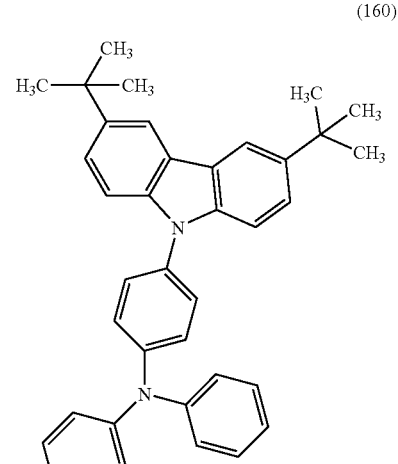

(161)
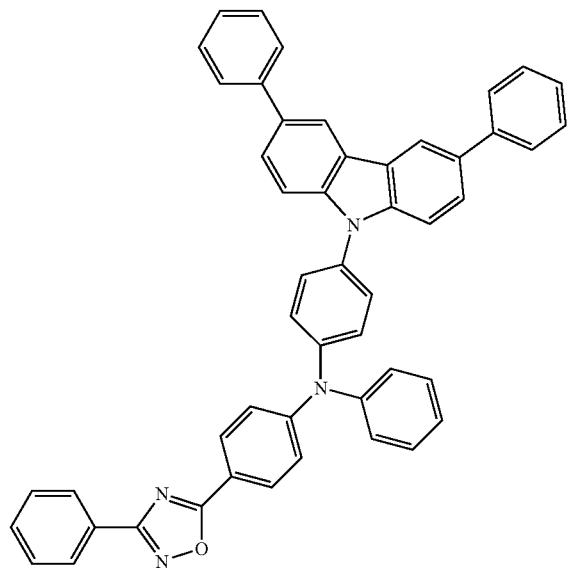
(162)
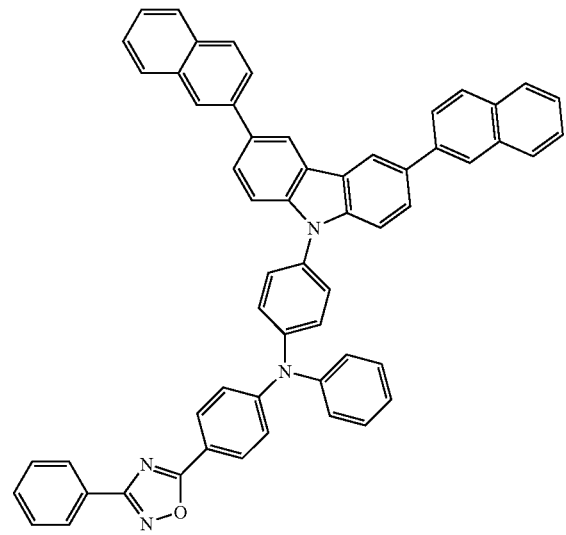
(163)
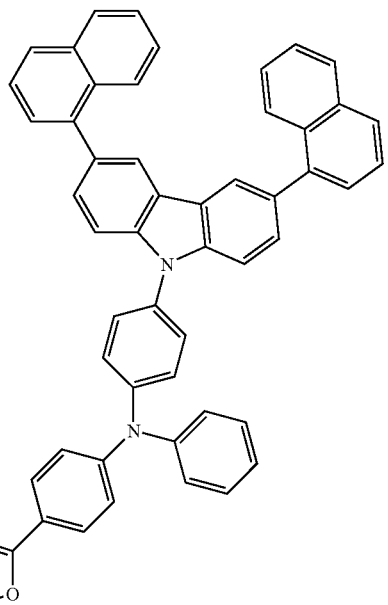
(164)
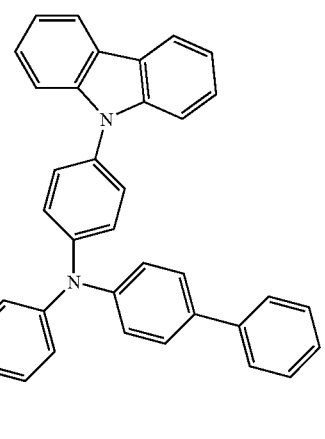
(165)
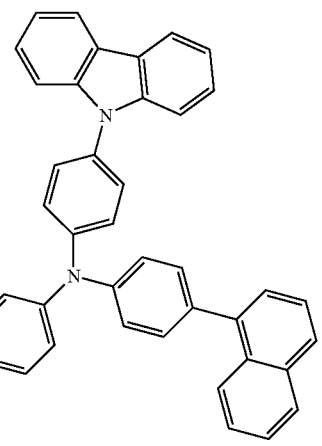

(166)
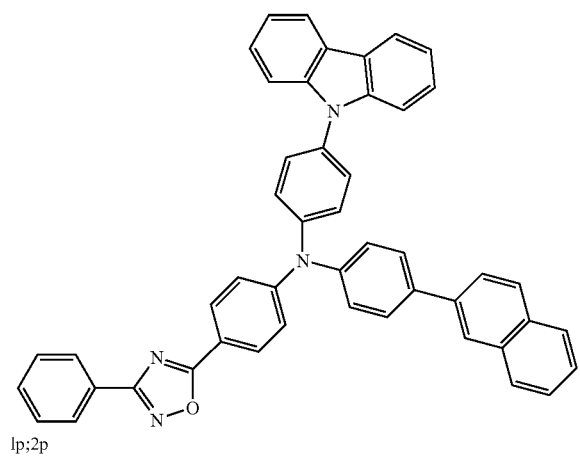
1p;2p
(167)
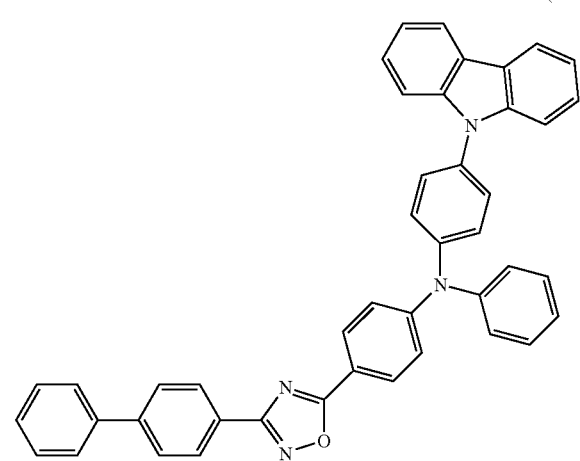
(168)
(169)
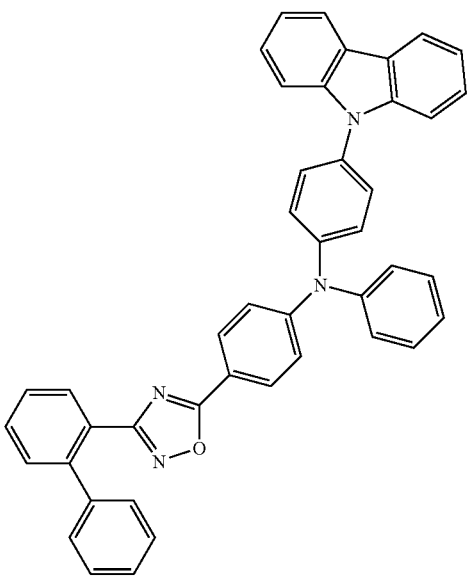
(170)
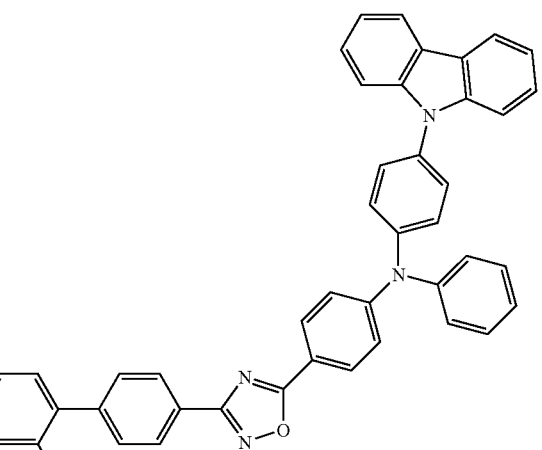
(171)
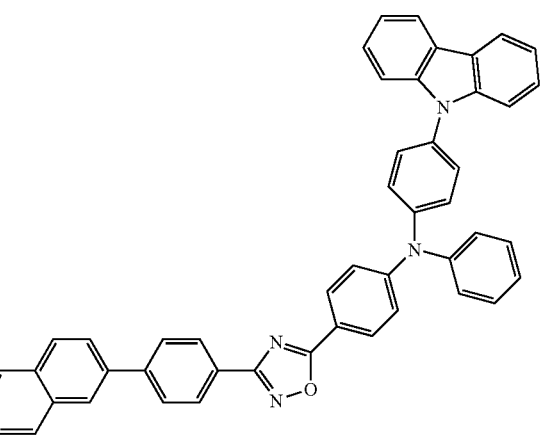

-continued
(172)
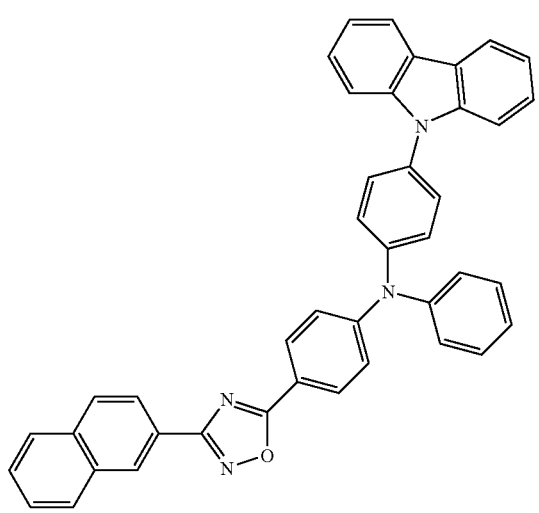
(173)
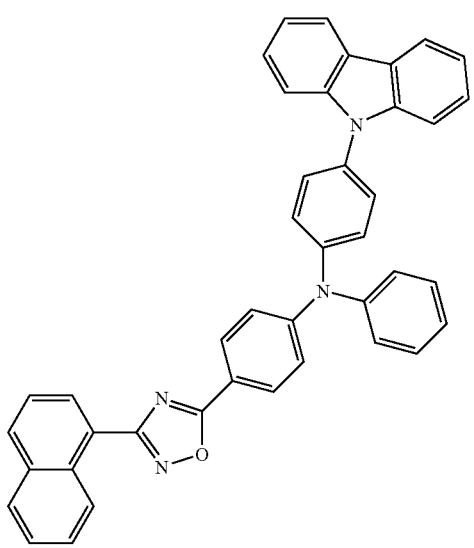
(174)
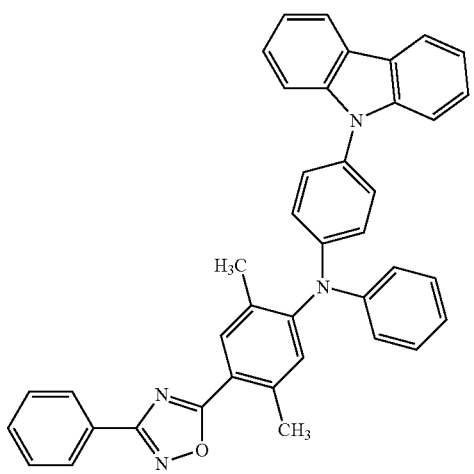
-continued
(175)
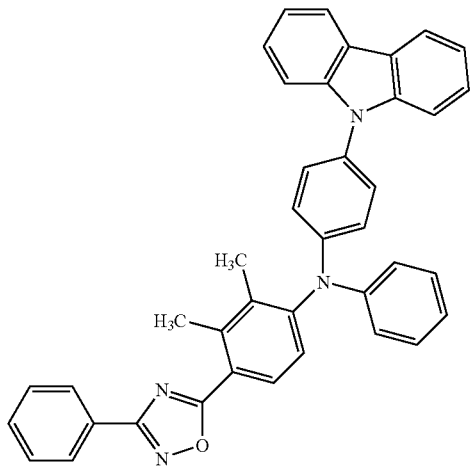
(176)
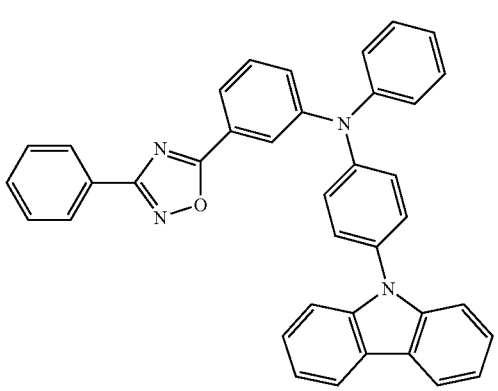
(177)
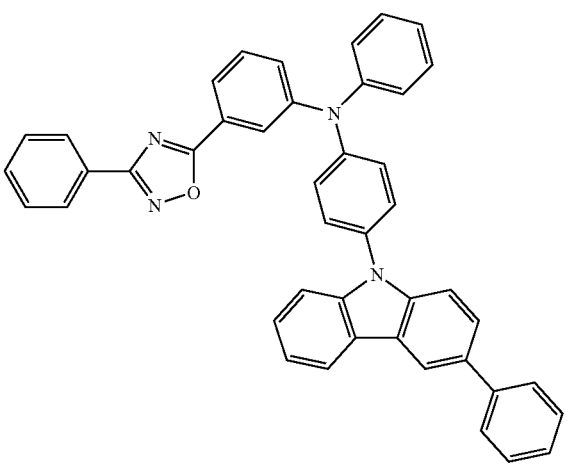

(178), (179), (180), (181)

(Z-1)

(Compound A)

(Compound B)

Coupling reaction using a metal catalyst (Compound C)
(1)

As a synthesis method of an oxadiazole derivative of the present invention, various reactions can be applied. For example, an oxadiazole derivative of the present invention can be synthesized by synthetic reactions shown in the following Reaction Formula (Z-1).

In the formula, $Ar^1$ represents a substituted or unsubstituted aryl group having 6 to 10 carbon atoms in a ring. A represents a substituted or unsubstituted phenylene group. $R^{11}$ to $R^{15}$ and $R^{21}$ to $R^{25}$ are independently any of hydrogen, an alkyl group having 1 to 4 carbon atoms, an aryl group having 6 to 10 carbon atoms in a ring, or a substituted or unsubstituted 9H-carbazol-9-yl group. A substituent of $Ar^1$ may be an alkyl group having 1 to 4 carbon atoms or an aryl group having 6 to 10 carbon atoms in a ring, and a substituent of A may be an alkyl group having 1 to 4 carbon atoms. A substituent of the 9H-carbazol-9-yl group may be an alkyl group having 1 to 4 carbon atoms or an aryl group having 6 to 10 carbon atoms in a ring. Further, carbon at α position and carbon at β position may be bonded to each other to form a carbazole ring.

An oxadiazole derivative (Compound A) and an arylamine derivative (Compound B) are coupled by a Hartwig-Buchwald reaction using a palladium catalyst or an Ullmann reaction using copper or a copper compound, whereby an objective compound (Compound C) represented by General Formula (1) can be obtained (Reaction Formula Z-1).

In Reaction Formula (Z-1), $X^1$ represents a halogen, preferably iodine or bromine. $Ar^1$ represents a substituted or unsubstituted aryl group having 6 to 10 carbon atoms in a ring. A represents a substituted or unsubstituted phenylene group. $R^{11}$ to $R^{15}$ and $R^{21}$ to $R^{25}$ are independently any of hydrogen, an alkyl group having 1 to 4 carbon atoms, an aryl group having 6 to 10 carbon atoms in a ring, or a substituted or unsubstituted 9H-carbazol-9-yl group. A substituent of $Ar^1$ may be an alkyl group having 1 to 4 carbon atoms or an aryl group having 6 to 10 carbon atoms in a ring, and a substituent of A may be an alkyl group having 1 to 4 carbon atoms. A substituent of the 9H-carbazol-9-yl group may be an alkyl group having 1 to 4 carbon atoms or an aryl group having 6 to 10 carbon atoms in a ring. Further, carbon at $\alpha$ position and carbon at $\beta$ position may be bonded to each other to form a carbazole ring.

In the case where the Hartwig-Buchwald reaction is carried out in Reaction Formula (Z-1), bis(dibenzylideneacetone) palladium(0), palladium(II) acetate, or the like can be used as the palladium catalyst. Examples of ligands of the palladium catalysts which can be used in Reaction Formula (Z-1) are tri(tert-butyl)phosphine, tri(n-hexyl)phosphine, tricyclohexylphosphine, and the like. Examples of bases which can be used in Reaction Formula (Z-1) are organic bases such as sodium tert-butoxide, inorganic bases such as potassium carbonate, and the like. Examples of solvents which can be used in Reaction Formula (Z-1) are toluene, xylene, benzene, tetrahydrofuran, and the like.

The case of performing the Ullmann reaction in Reaction Formula (Z-1) will be described. In Reaction Formula (Z-1), copper(I) iodide, copper(II) acetate, or the like can be used as the copper compound. As an alternative to the copper compound, copper can be used. Examples of bases which can be used in Reaction Formula (Z-1) are inorganic bases such as potassium carbonate, and the like. Examples of solvents which can be used in Reaction Formula (Z-1) are 1,3-dimethyl-3,4,5,6-tetrahydro-2(1H)pyrimidinone (abbreviated to DMPU), toluene, xylene, benzene, and the like. In the Ullmann reaction, since the objective compound can be obtained in a shorter time and in a higher yield when the reaction temperature is 100° C. or higher, it is preferable to use DMPU or xylene which has a high boiling temperature. Because the reaction temperature of 150° C. or higher is further preferable, DMPU is more preferably used.

In the above-described manner, oxadiazole derivatives of this embodiment can be synthesized.

The oxadiazole derivatives of this embodiment each have an extremely large band gap and are bipolar materials having a hole-transporting property and an electron-transporting property.

The oxadiazole derivatives of this embodiment can be used alone as a light-emission center material in a layer containing a light-emitting substance (a light-emitting layer). Further, the oxadiazole derivatives of this embodiment can also be used as a host material. Light emission from a dopant that functions as a light-emitting substance can be obtained with a structure in which the dopant is dispersed in an oxadiazole derivative of this embodiment. When the oxadiazole derivative is used as a host material, light emission from the dopant can be obtained efficiently.

Further, any of the oxadiazole derivatives of this embodiment can be used for a layer containing a light-emitting substance by being dispersed in a material (a host material) having a larger band gap than the oxadiazole derivative of this embodiment, whereby light emission from the oxadiazole derivative of this embodiment can be obtained. That is, the oxadiazole derivative of this embodiment can also function as a dopant. Here, since the oxadiazole derivative of this embodiment has an extremely large band gap and light with a short wavelength is exhibited, a light-emitting element that can exhibit bluish-violet to blue light emission can be manufactured.

An embodiment of the oxadiazole derivative of the present invention can be used as a carrier-transporting material for a functional layer of a light-emitting element. For example, the oxadiazole derivative can be used in a carrier-transporting layer such as a hole-transporting layer or an electron-transporting layer, or a carrier-injecting layer such as a hole-injecting layer or an electron-injecting layer.

Embodiment 2

An embodiment of a light-emitting element including the oxadiazole derivative of the present invention will be described below with reference to FIGS. 1A to 1C.

In an embodiment of the light-emitting element of the present invention, an EL layer which includes a layer containing a light-emitting substance (the layer is also referred to as a light-emitting layer) is interposed between a pair of electrodes. The EL layer may also include a plurality of layers in addition to the layer containing a light-emitting substance. The plurality of layers is a combination of layers formed using a material having a high carrier-injecting property and a material having a high carrier-transporting property. Those layers are stacked so that a light-emitting region is formed in a region away from the electrodes, that is, carriers are recombined in a region away from the electrodes. In this specification, the layer formed using a substance having a high carrier-injecting property or a substance having a high carrier-transporting property is also referred to as a functional layer which functions, for example, to inject or transport carriers. For the functional layer, it is possible to use any of a layer containing a substance having a high hole-injecting property (also referred to as a hole-injecting layer), a layer containing a substance having a high hole-transporting property (also referred to as a hole-transporting layer), a layer containing a substance having a high electron-injecting property (also referred to as an electron-injecting layer), a layer containing a substance having a high electron-transporting property (also referred to as an electron-transporting layer), and the like.

Figure 1B:
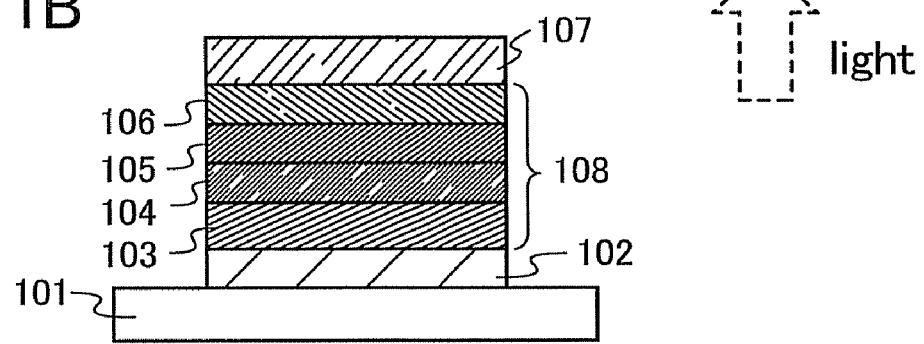
Figure 1C:
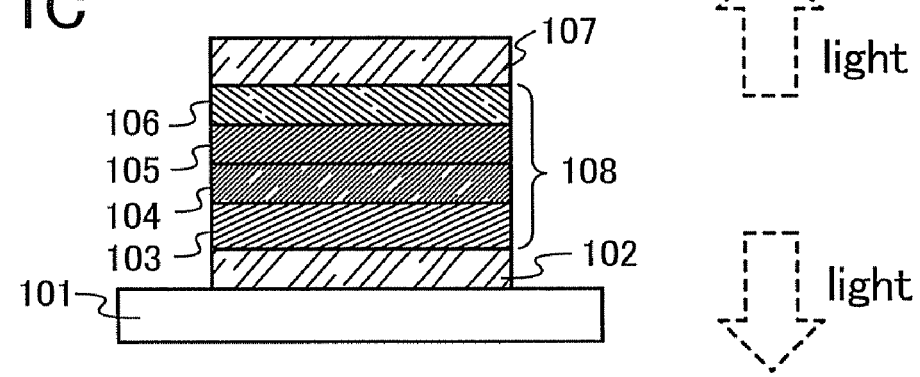

In each of the light-emitting elements of this embodiment illustrated in FIGS. 1A to 1C, an EL layer 108 is provided between a pair of electrodes: a first electrode 102 and a second electrode 107. The EL layer 108 includes a first layer 103, a second layer 104, a third layer 105, and a fourth layer 106. The light-emitting elements in FIGS. 1A to 1C include a first electrode 102 over a substrate 101; the first layer 103, the second layer 104, the third layer 105, and the fourth layer 106 stacked in that order over the first electrode 102; and a second electrode 107 provided thereover. Note that in this embodiment, the following description will be made on the assumption that the first electrode 102 functions as an anode and that the second electrode 107 functions as a cathode.

The substrate 101 is used as a support of the light-emitting element. For example, glass, quartz, plastic, or the like can be used for the substrate 101. Alternatively, a flexible substrate may be used. A flexible substrate is a substrate that can be bent and, for example, a plastic substrate made of polycarbonate, polyarylate, or polyether sulfone can be given. Alternatively, a film (made of polypropylene, polyester, vinyl, polyvinyl fluoride, vinyl chloride, or the like), an inorganic evaporated film, or the like can be used. Note that other substrates may also be used as long as they function as a support in a manufacturing process of the light-emitting element.

It is preferable that the first electrode 102 be formed using a metal, an alloy, or a conductive compound with a high work function (specifically, 4.0 eV or higher), a mixture thereof, or the like. Specifically, for example, indium tin oxide (ITO), indium tin oxide containing silicon or silicon oxide, indium zinc oxide (IZO), indium oxide containing tungsten oxide and zinc oxide (IWZO), and the like are given. Films of those conductive metal oxides are generally formed by sputtering, but they may be formed by a sol-gel method or the like. For example, a film of indium zinc oxide (IZO) can be formed by a sputtering method using a target in which zinc oxide is added to indium oxide at 1 wt % to 20 wt %. A film of indium oxide containing tungsten oxide and zinc oxide (IWZO) can be formed by a sputtering method using a target in which tungsten oxide and zinc oxide are added to indium oxide at 0.5 wt % to 5 wt % and 0.1 wt % to 1 wt %, respectively. In addition, gold (Au), platinum (Pt), nickel (Ni), tungsten (W), chromium (Cr), molybdenum (Mo), iron (Fe), cobalt (Co), copper (Cu), palladium (Pd), nitride of a metal material (such as titanium nitride), and the like can be given.

The first layer 103 contains a substance having a high hole-injecting property. Molybdenum oxide, vanadium oxide, ruthenium oxide, tungsten oxide, manganese oxide, or the like can be used. Alternatively, the first layer 103 can be formed using any of the following materials: phthalocyanine-based compounds such as phthalocyanine ($H_2Pc$) and copper phthalocyanine (CuPc), aromatic amine compounds such as 4,4'-bis[N-(4-diphenylaminophenyl)-N-phenylamino]biphenyl (DPAB) and N,N'-bis[4-[bis(3-methylphenyl)amino]phenyl]-N,N'-diphenyl-[1,1'-Biphenyl]-4,4'-diamine (DNTPD), high molecular compounds such as poly(3,4-ethylenedioxythiophene)/poly(styrenesulfonic acid) (PEDOT/PSS), and the like.

Further, the first layer 103 can be formed using a composite material formed by composition of an organic compound and an inorganic compound. In particular, a composite material which contains an organic compound and an inorganic compound showing an electron-accepting property to the organic compound is excellent in a hole-injecting property and a hole-transporting property since electrons are transferred between the organic compound and the inorganic compound and carrier density is increased.

In the case of using the composite material containing an organic compound and an inorganic compound for the first layer 103, the first layer 103 can achieve an ohmic contact with the first electrode 102; therefore, a material of the first electrode can be selected regardless of the work function.

As the inorganic compound used for the composite material, an oxide of a transition metal is preferable. In addition, an oxide of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable because of their high electron-accepting properties. Among them, molybdenum oxide is preferable because it can be easily handled due to its stableness in air and low hygroscopic property.

As the organic compound which is used for the composite material, any of various compounds such as an aromatic amine compound, a carbazole derivative, aromatic hydrocarbon, or a high molecular compound (an oligomer, a dendrimer, a polymer, or the like) can be used. Note that the organic compound used for the composite material is preferably an organic compound having a high hole-transporting property. Specifically, a substance having a hole mobility of $10^{-6}$ $cm^2/Vs$ or higher is preferable. However, any other substance whose hole-transporting property is higher than the electron-transporting property may be used. The organic compounds that can be used for the composite material are specifically given below.

Examples of an aromatic amine compound specifically include N,N'-di(p-tolyl)-N,N'-diphenyl-p-phenylenediamine (DTDPPA), 4,4'-bis[N-(4-diphenylaminophenyl)-N-phenylamino]biphenyl (DPAB), N,N'-bis[4-[bis(3-methylphenyl)amino]phenyl]-N,N'-diphenyl-[1,1'-biphenyl]-4,4'-diamine (DNTPD), and 1,3,5-tris[N-(4-diphenylaminophenyl)-N-phenylamino]benzene (DPA3B).

Examples of a carbazole derivative which can be used for the composite material specifically include 3-[N-(9-phenylcarbazol-3-yl)-N-phenylamino]-9-phenylcarbazole (PCzPCA1), 3,6-bis[N-(9-phenylcarbazol-3-yl)-N-phenylamino]-9-phenylcarbazole (PCzPCA2), and 3-[N-(1-naphthyl)-N-(9-phenylcarbazol-3-yl)amino]-9-phenylcarbazole (PCzPCN1).

In addition, the following can also be used: 4,4'-di(N-carbazolyl)biphenyl (CBP), 1,3,5-tris[4-(N-carbazolyl)phenyl]benzene (TCPB), 9-[4-(N-carbazolyl)]phenyl-10-phenylanthracene (CzPA), 1,4-bis[4-(N-carbazolyl)phenyl]-2,3,5,6-tetraphenylbenzene, and the like.

Further, examples of an aromatic hydrocarbon which can be used for the composite material include 2-tert-butyl-9,10-di(2-naphthyl)anthracene (t-BuDNA), 2-tert-butyl-9,10-di(1-naphthyl)anthracene, 9,10-bis(3,5-diphenylphenyl)anthracene (DPPA), 2-tert-butyl-9,10-bis(4-phenylphenyl)anthracene (t-BuDBA), 9,10-di(2-naphthyl)anthracene (DNA), 9,10-diphenylanthracene (DPAnth), 2-tert-butylanthracene (t-BuAnth), 9,10-bis(4-methyl-1-naphthyl)anthracene (DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra(tert-butyl)perylene. Besides, pentacene, coronene, or the like can be used. Thus, an aromatic hydrocarbon having a hole mobility of $1\times10^{-6}$ $cm^2/Vs$ or higher and having 14 to 42 carbon atoms is preferable.

Note that an aromatic hydrocarbon which can be used for the composite material may have a vinyl skeleton. Examples of an aromatic hydrocarbon having a vinyl group include 4,4'-bis(2,2-diphenylvinyl)biphenyl (DPVBi) and 9,10-bis[4-(2,2-diphenylvinyl)phenyl]anthracene (DPVPA).

Further, a high molecular compound such as poly(N-vinylcarbazole) (PVK) or poly(4-vinyltriphenylamine) (PVTPA) can also be used.

As a substance for forming the second layer 104, a substance having a high hole-transporting property, specifically, an aromatic amine compound (that is, a compound having a benzene ring-nitrogen bond) is preferable. Examples of materials which are widely used include 4,4'-bis[N-(3-methylphenyl)-N-phenylamino]biphenyl; a derivative thereof such as 4,4'-bis[N-(1-napthyl)-N-phenylamino]biphenyl (hereinafter referred to as NPB); and a starburst aromatic amine compound such as 4,4',4''-tris(N,N-diphenyl-amino)triphenylamine or 4,4',4''-tris[N-(3-methylphenyl)-N-phenylamino]triphenylamine. Most of the substances mentioned here have a hole mobility of $10^{-6}$ $cm^2/Vs$ or higher. However, any other material whose hole-transporting property is higher than the electron-transporting property may be used. Note that the second layer 104 is not limited to a single layer, and may be a mixed layer of any of the above substances, or a stacked layer having two or more layers each formed using any of the above substances.

Alternatively, a hole-transporting material may be added to a high molecular compound that is electrically inactive, such as PMMA.

Further, a high molecular compound such as poly(N-vinylcarbazole) (PVK), poly(4-vinyltriphenylamine) (PVTPA), poly[N-(4-{N'-[4-(4-diphenylamino)phenyl]phenyl-N'-phenylamino}phenyl)methacrylamide] (PTPDMA), or poly[N,N'-bis(4-butylphenyl)-N,N'-bis(phenyl)benzidine (poly-TPD) may be used, and further, any of the above-described hole-transporting materials may be added to the high molecular compounds as appropriate.

The third layer 105 is a layer containing a light-emitting substance (the layer is also referred to as a light-emitting layer). In this embodiment, the third layer 105 is formed using any of the oxadiazole derivatives described in Embodiment 1 of the present invention. The oxadiazole derivative of the present invention exhibits bluish-violet to blue light emission, and thus can be preferably used as a light-emitting substance for a light-emitting element.

Further, in the third layer 105, the oxadiazole derivative of the present invention can also be used as a host material. Light emission from a dopant that functions as a light-emitting substance can be obtained with a structure in which the dopant is dispersed in the oxadiazole derivative of the present invention.

The oxadiazole derivative of the present invention has a large band gap and is a bipolar material which allows a hole and an electron to flow.

When the oxadiazole derivative of the present invention is used as a material in which another light-emitting substance is dispersed, emission color originating from the light-emitting substance can be obtained. Further, it is also possible to obtain a mixed color of an emission color originating from the oxadiazole derivative of the present invention and an emission color originating from the light-emitting substance dispersed in the oxadiazole derivative.

Further, the oxadiazole derivative of the present invention can be used for a layer containing a light-emitting substance by being dispersed in a material (a host material) having a larger band gap than the oxadiazole derivative, whereby light emission from the oxadiazole derivative can be obtained. That is, the oxadiazole derivative of the present invention can also function as a dopant. Here, since the oxadiazole derivative of the present invention has an extremely large band gap and light with a short wavelength is exhibited, a light-emitting element that can exhibit bluish-violet to blue light emission can be manufactured.

Here, any of a variety of materials can be used as the light-emitting substance which is dispersed in the oxadiazole derivative of the present invention. Specifically, fluorescent substances that emit fluorescence can be given: 2-(2-{2-[4-(dimethylamino)phenyl]ethenyl}-6-methyl-4H-pyran-4-ylidene)propanedinitrile (DCM1), 2-{2-methyl-6-[2-(2,3,6,7-tetrahydro-1H,5H-benzo[ij]quinolizin-9-yl)ethenyl]-4H-pyran-4-ylidene}propanedinitrile (DCM2), N,N,N',N'-tetrakis(4-methylphenyl)tetracene-5,11-diamine (p-mPhTD); 7,14-diphenyl-N,N,N',N'-tetrakis(4-methylphenyl)acenaphtho[1,2-a]fluoranthene-3,10-diamine (p-mPhAFD); 2-{isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (DCJTI); 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (DCJTB); 2-(2,6-bis{2-[4-(dimethylamino)phenyl]ethenyl}-4H-pyran-4-ylidene)propanedinitrile (BisDCM); 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (BisDCJTM); and the like. Further, phosphorescent substances that emit phosphorescence can be given: bis[2-(2'-benzo[4,5-α]thienyl)pyridinato-N,$C^3$]iridium(III)acetylacetonate ($Ir(btp)_2(acac)$); bis(1-phenylisoquinolinato-N,$C^{2'}$)iridium(III) acetylacetonate ($Ir(btp)_2(acac)$); (acetylacetonato)bis[2,3-bis(4-fluorophenyl)quinoxalinato]iridium(III) ($Ir(Fdpq)_2(acac)$); (acetylacetonato)bis(2,3,5-triphenylpyrazinato)iridium(III) ($Ir(tppr)_2(acac)$); 2,3,7,8,12,13,17,18-octaethyl-21H,23H-porphyrinplatinum(II) (PtOEP); tris(1,3-diphenyl-1,3-propanedionato)(monophenanthroline)europium(III) ($Eu(DBM)_3(Phen)$); tris[1-(2-thenoyl)-3,3,3-trifluoroacetonato](monophenanthroline)europium(III) ($Eu(TTA)_3(Phen)$); and the like.

The fourth layer 106 can be formed using a substance having a high electron-transporting property. For example, the fourth layer 106 is formed using a metal complex having a quinoline skeleton or a benzoquinoline skeleton, such as tris(8-quinolinolato)aluminum (Alq), tris(4-methyl-8-quinolinolato)aluminum ($Almq_3$), bis(10-hydroxybenzo[h]quinolinato)beryllium ($BeBq_2$); or bis(2-methyl-8-quinolinolato)(4-phenylphenolato)aluminum (BAlq). Other examples which can be used are metal complexes having an oxazole-based ligand or a thiazole-based ligand, such as bis[2-(2-hydroxyphenyl)benzoxazolato]zinc ($Zn(BOX)_2$) and bis[2-(2-hydroxyphenyl)benzothiazolato]zinc ($Zn(BTZ)_2$). Furthermore, other than metal complexes, the following can also be used: 2-(4-biphenylyl)-5-(4-tert-butylphenyl)-1,3,4-oxadiazole (PBD), 1,3-bis[5-(p-tert-butylphenyl)-1,3,4-oxadiazol-2-yl]benzene (OXD-7), 3-(4-biphenylyl)-4-phenyl-5-(4-tert-butylphenyl)-1,2,4-triazole (TAZ), bathophenanthroline (BPhen), bathocuproine (BCP), and the like. Most of the substances mentioned here have an electron mobility of $10^{-6}$ $cm^2/Vs$ or higher. Note that any other material whose electron-transporting property is higher than the hole-transporting property may be used for an electron-transporting layer. Further the electron-transporting layer is not limited to a single layer, and may be a stacked layer having two or more layers each formed using any of the above substances.

Further, a layer having a function of promoting electron injection (an electron-injecting layer) may be provided between the fourth layer 106 and the second electrode 107. For a layer having a function of promoting electron injection, an alkali metal, an alkaline earth metal, or a compound thereof, such as lithium fluoride (LiF), cesium fluoride (CsF), or calcium fluoride ($CaF_2$), can be used. For example, a layer of a substance having an electron-transporting property containing an alkali metal, an alkaline earth metal, or a compound thereof, such as a layer of Alq which contains magnesium (Mg), may be used. Note that by using a layer of a substance having an electron-transporting property containing an alkali metal, an alkaline earth metal, or a compound thereof as an electron-injecting layer, electrons can be injected efficiently from the second electrode 107, which is preferable.

As a substance for forming the second electrode 107, a metal, an alloy, an electroconductive compound, a mixture thereof, or the like having a low work function (specifically, 3.8 eV or lower) can be used. Specific examples of such a cathode material are given below: elements belonging to Group 1 and Group 2 of the periodic table, that is, alkali metals such as lithium (Li) and cesium (Cs) and alkaline earth metals such as magnesium (Mg), calcium (Ca), and strontium (Sr); alloys thereof (e.g., MgAg and AlLi); rare earth metals such as europium (Eu) and ytterbium (Yb); and alloys thereof. However, by providing a layer having a function of promoting electron injection between the second electrode 107 and the fourth layer 106 so that it is stacked with the second electrode, any of a variety of conductive materials such as Al, Ag, ITO, and ITO containing silicon or silicon oxide can be used for the second electrode 107, regardless of the work function.

Further, the oxadiazole derivative of the present invention can also be used for a functional layer of the light-emitting element.

For the formation of the first layer 103, the second layer 104, the third layer 105, and the fourth layer 106, any of a variety of methods such as an evaporation method, a sputtering method, a droplet discharge method (an inkjet method), a spin coating method, or a printing method can be employed. Further, a different film formation method may be used to form each electrode or each layer.

In the case where a thin film is formed by a wet process using a composition in a solution form in which the oxadiazole derivative of the present invention is dissolved in a solvent, the thin film is formed in such a manner that a material for forming the thin film which includes the oxadiazole derivative of the present invention is dissolved in the solvent, the composition in a solution form is attached to a region where the thin film is to be formed, the solvent is removed, and the resulting material is solidified.

For a wet process, any of the following methods can be employed: a spin coating method, a roll coating method, a spray method, a casting method, a dipping method, a droplet discharge (ejection) method (an inkjet method), a dispenser method, any of a variety of printing methods (a method by which a film having a desired pattern can be formed, such as screen (stencil) printing, offset (planographic) printing, letterpress printing, or gravure (intaglio) printing). Note that without limitation to the above methods, the thin film of the composition of the present invention can be formed by any of the other methods in which a liquid composition can be used.

Further, any of a variety of solvents can be used in the above composition. For example, the above oxadiazole derivative can be dissolved in a solvent that has an aromatic ring (e.g., a benzene ring), such as toluene, xylene, methoxybenzene (anisole), dodecylbenzene, or a mixed solvent of dodecylbenzene and tetralin. Further, the above oxadiazole derivative can also be dissolved in an organic solvent which does not include an aromatic ring, such as dimethylsulfoxide (DMSO), dimethylformamide (DMF), or chloroform.

Further, there are other solvents such as ketone-based solvents such as acetone, methyl ethyl ketone, diethyl ketone, n-propyl methyl ketone, and cyclohexanone; ester-based solvents such as ethyl acetate, n-propyl acetate, n-butyl acetate, ethyl propionate, γ-butyrolactone, and diethyl carbonate; ether solvents such as diethylether, tetrahydrofuran and dioxane; and alcohol solvents such as ethanol, isopropanol, 2-methoxyethanol, and 2-ethoxyethanol.

Further, a composition which is described in this embodiment may also contain another organic material. As the organic material, an aromatic compound or a heteroaromatic compound which is solid at room temperature can be given. For the organic material, a low molecular compound or a high molecular compound can be used. When a low molecular compound is used, a low molecular compound (which may be referred to as a medium molecular compound) including a substituent which can increase the solubility in a solvent is preferably used.

The composition may further include a binder in order to improve the quality of a film that is to be formed. A high molecular compound that is electrically inactive is preferably used as the binder. Specifically, polymethylmethacrylate (PMMA), polyimide, or the like can be used.

In the light-emitting element of the present invention which has the structure as described above, the potential difference between the first electrode 102 and the second electrode 107 makes current flow, whereby holes and electrons recombine in the third layer 105 containing a substance having a high light-emitting property and thus light is emitted. That is, a light-emitting region is formed in the third layer 105.

Emitted light is extracted out through one or both of the first electrode 102 and the second electrode 107. Accordingly, either or both the first electrode 102 and the second electrode 107 are formed using a light-transmitting substance. When only the first electrode 102 is formed using a light-transmitting substance, emitted light is extracted from the substrate side through the first electrode 102 as illustrated in FIG. 1A. When only the second electrode 107 is formed using a light-transmitting substance, emitted light is extracted from the side opposite to the substrate, through the second electrode 107 as illustrated in FIG. 1B. When both the first electrode 102 and the second electrode 107 are formed using a light-transmitting substance, emitted light is extracted from both the substrate side and the side opposite to the substrate, through the first electrode 102 and the second electrode 107, respectively, as illustrated in FIG. 1C.

Note that the structure of the layers provided between the first electrode 102 and the second electrode 107 is not limited to the above example. A structure other than the above may alternatively be employed as long as a light-emitting region in which holes and electrons are recombined is provided in a portion away from the first electrode 102 and the second electrode 107 in order to prevent quenching due to proximity of the light-emitting region to a metal.

In other words, there is no particular limitation on the stacked structure of the layers. The light-emitting layer containing the oxadiazole derivative of the present invention may be freely combined with layers containing a substance having a high electron-transporting property, a substance having a high hole-transporting property, a substance having a high electron-injecting property, a substance having a high hole-injecting property, a bipolar substance (a substance with a high electron-transporting and hole-transporting property), a hole-blocking material, and the like.

Figure 2:
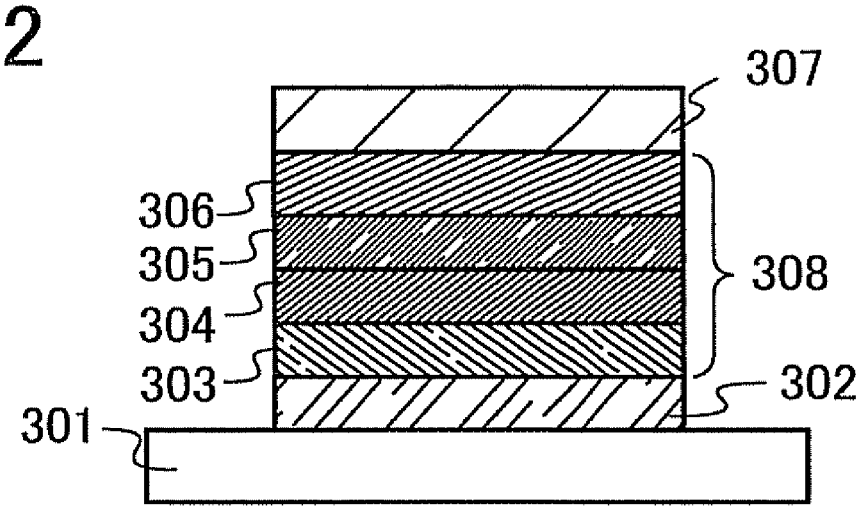
FIG. 2 is a view illustrating a light-emitting element.

In a light-emitting element illustrated in FIG. 2, over a substrate 301, an EL layer 308 is provided between a pair of electrodes: a first electrode 302 and a second electrode 307. The EL layer 308 includes a first layer 303 formed using a substance having a high electron-transporting property, a second layer 304 containing a light-emitting substance, a third layer 305 formed using a substance having a high hole-transporting property, and a fourth layer 306 formed using a substance having a high hole-injecting property. The first electrode 302 which functions as a cathode, the first layer 303 formed using a substance having a high electron-transporting property, the second layer 304 containing a light-emitting substance, the third layer 305 formed using a substance having a high hole-transporting property, the fourth layer 306 fowled using a substance having a high hole-injecting property, and the second electrode 307 which functions as an anode are stacked in this order.

A specific formation method of a light-emitting element will be described below.

In the light-emitting element of the present invention, an EL layer is interposed between a pair of electrodes. The EL layer includes at least a layer containing a light-emitting substance formed using the oxadiazole derivative of the present invention (the layer is also referred to as a light-emitting layer). In addition to the layer containing a light-emitting substance, the EL layer may include a functional layer (e.g., a hole-injecting layer, a hole-transporting layer, an electron-transporting layer, or an electron-injecting layer). The electrodes (the first electrode and the second electrode), the layer containing a light-emitting substance, and the functional layers may be formed by a wet processes such as a droplet discharge method (an inkjet method), a spin coating method, or a printing method, or by a dry process such as a vacuum evaporation method, a CVD method, or a sputtering method. The use of a wet process enables the formation under atmospheric pressure using a simple apparatus and process, and thus effects of simplifying the process and improving the productivity can be obtained. In contrast, in a dry process, dissolution of a material is not needed, and thus, a material that has low solubility in a solution can be used, which leads to expansion of material choices.

All the thin films included in the light-emitting element may be formed by a wet process. In this case, the light-emitting element can be manufactured with only facilities needed for a wet process. Alternatively, formation of the stacked layers up to formation of the layer containing a light-emitting substance may be performed by a wet process whereas the functional layer, the second electrode, and the like which are stacked over the layer containing a light-emitting substance may be formed by a dry process. Further alternatively, the first electrode and the functional layers may be formed by a dry process before the formation of the layer containing a light-emitting substance whereas the layer containing a light-emitting substance, the functional layer stacked thereover, and the second electrode may be formed by a wet process. It is needless to say that the present invention is not limited thereto. The light-emitting element can be formed by appropriate selection from a wet process and a dry process depending on a material that is to be used, a required film thickness, and an interface state.

In this embodiment, the light-emitting element is manufactured over a substrate made of glass, plastic, or the like. When a plurality of such light-emitting elements are manufactured over one substrate, a passive matrix light-emitting device can be manufactured. Alternatively, for example, thin film transistors (TFTs) may be formed over a substrate formed using glass, plastic, or the like, and then, light-emitting elements may be manufactured over an electrode that is electrically connected to the TFTs. Thus, an active matrix light-emitting device in which drive of the light-emitting elements is controlled by the TFTs can be manufactured. Note that there is no particular limitation on the structure of the TFT. Either a staggered TFT or an inverted staggered TFT may be employed. Further, there is no particular limitation on the crystallinity of a semiconductor used for forming the TFTs, and an amorphous semiconductor or a crystalline semiconductor may be used. In addition, a driver circuit formed over a TFT substrate may be formed using n-channel and p-channel TFTs, or using either n-channel or p-channel TFTs.

An embodiment of the oxadiazole derivative of the present invention is a bipolar material which allows both a hole and an electron to flow.

An embodiment of the oxadiazole derivative of the present invention can also be used as either a light-emitting material (including a dopant as well) or a host material in a light-emitting layer of a light-emitting element.

Since an embodiment of the oxadiazole derivative of the present invention has a large band gap, in the case of a light-emitting element including a light-emitting layer in which the oxadiazole derivative is used as a host material, light emission not from the oxadiazole derivative but from a dopant can be obtained efficiently.

Further, with the use of an embodiment of the oxadiazole derivative of the present invention, a light-emitting element, a light-emitting device, and an electronic device with lower power consumption can be provided.

Embodiment 3

Figure 11A:
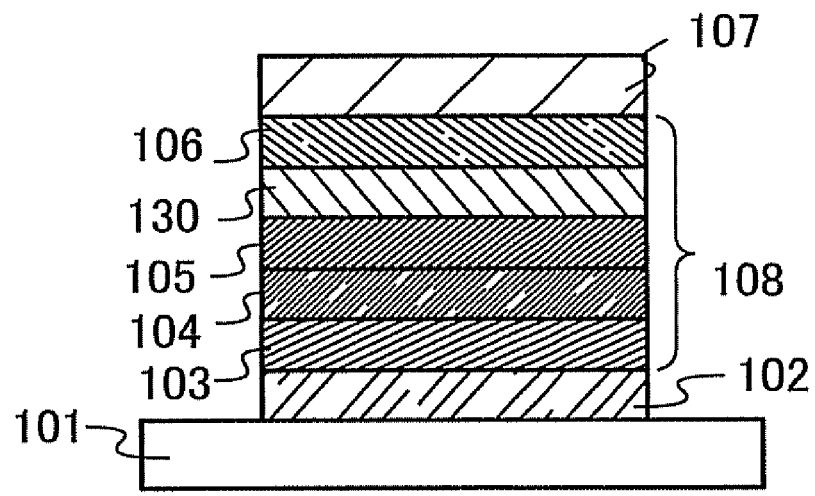
FIGS. 11A and 11B are views each illustrating a light-emitting element.
Figure 11B:
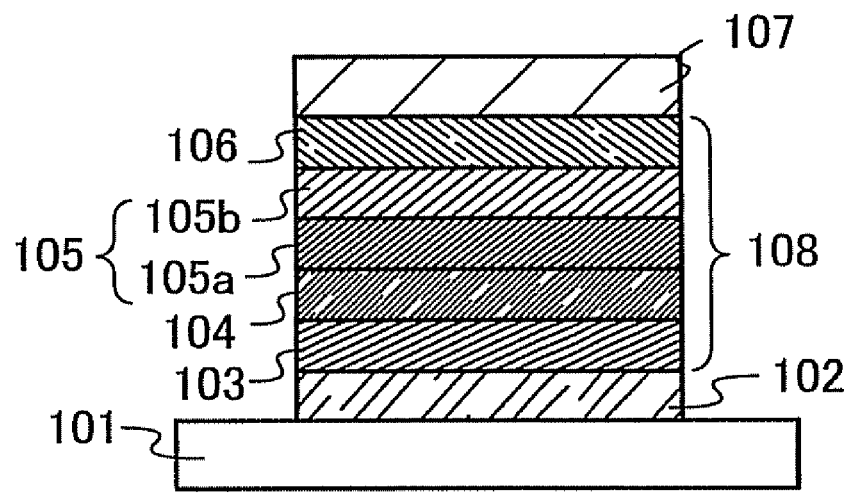

In this embodiment, a light-emitting element having a different structure from the structure described in Embodiment 2 will be described with reference to FIGS. 11A and 11B.

A layer which controls movement of electron carriers may be provided between an electron-transporting layer and a light-emitting layer. FIG. 11A illustrates a structure in which a layer 130 which controls movement of electron carriers is provided between a fourth layer 106 which functions as an electron-transporting layer and a third layer 105 which functions as an light-emitting layer (the third layer 105 is also referred to as a light-emitting layer 105). The layer 130 which controls movement of electron carriers is a layer which is formed by adding a small amount of substance having a high electron-trapping property to the above material having a high electron-transporting property, or a layer formed by adding a material having a hole-transporting property with a low lowest unoccupied molecular orbital (LUMO) energy level to a material having a high electron-transporting property. With such a layer, movement of electron carriers is controlled, whereby carrier balance can be adjusted. Such a structure is very effective in suppressing a problem (such as shortening of element lifetime) caused by electrons passing through the third layer 105.

Further, another structure may be employed in which the light-emitting layer 105 includes two or more layers. FIG. 11B illustrates an example in which the light-emitting layer 105 includes two layers: a first light-emitting layer 105a and a second light-emitting layer 105b.

For example, if the first light-emitting layer 105a and the second light-emitting layer 105b are stacked in this order over the second layer 104 which functions as a hole-transporting layer to form the light-emitting layer 105, a substance having a hole-transporting property can be used as a host material of the first light-emitting layer 105a and a substance having an electron-transporting property can be used for the second light-emitting layer 105b.

The oxadiazole derivative of the present invention can be used alone for a light-emitting layer. Further, the oxadiazole derivative of the present invention can also be used as a host material or even as a dopant.

If the oxadiazole derivative of the present invention is used as a host material, light emission from a dopant that functions as a light-emitting substance can be obtained with a structure in which the dopant is dispersed in the oxadiazole derivative.

On the other hand, when the oxadiazole derivative of the present invention is used as a dopant, light emission from the oxadiazole derivative can be obtained with a structure in which the oxadiazole derivative is added to a layer formed using a material (a host) which has a larger band gap than the oxadiazole derivative.

Further, the oxadiazole derivative of the present invention has both a hole-transporting property and an electron-transporting property, that is, a bipolar property. When the oxadiazole derivative has a hole-transporting property, it can be used for the first light-emitting layer 105a. When the oxadiazole derivative has an electron-transporting property, it can be used for the second light-emitting layer 105b. The oxadiazole derivative of the present invention can be used alone for the first light-emitting layer 105a or the second light-emitting layer 105b or can be used as a host material or a dopant. When the oxadiazole derivative is used alone for a light-emitting layer or is used as a host material, whether the oxadiazole derivative is used for the first light-emitting layer 105a having a hole-transporting property or the second light-emitting layer 105b having an electron-transporting property may be determined depending on the carrier-transporting property.

Note that this embodiment can be implemented in combination with any of the other embodiments as appropriate.

Embodiment 4

In this embodiment, one mode of a light-emitting element having a structure in which a plurality of light-emitting units according to the present invention are stacked (hereinafter this type of light-emitting element is referred to as a stacked type element) will be described with reference to FIG. 3. This light-emitting element has a plurality of light-emitting units between a first electrode and a second electrode.

Figure 3:
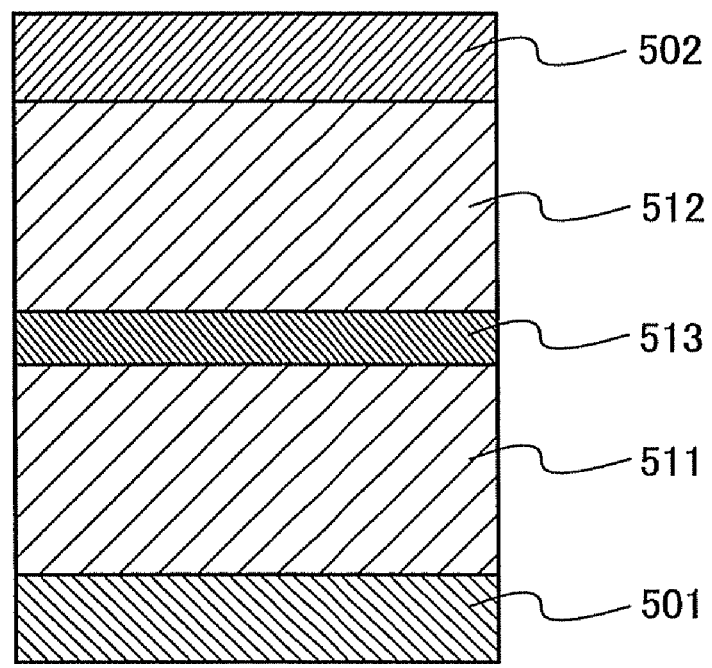
FIG. 3 is a view illustrating a light-emitting element.

In FIG. 3, a first light-emitting unit 511 and a second light-emitting unit 512 are stacked between a first electrode 501 and a second electrode 502. As for the first electrode 501 and the second electrode 502, electrodes similar to those described in Embodiment 2 can be used. The structures of the first light-emitting unit 511 and the second light-emitting unit 512 may be the same or different. Their structures can be similar to that described in Embodiment 2.

A charge generation layer 513 contains a composite material of an organic compound and a metal oxide. This composite material of an organic compound and a metal oxide is a composite material described in Embodiment 2 and includes an organic compound and a metal oxide such as $V_2O_5$, $MoO_3$ or $WO_3$. As the organic compound, any of a variety of compounds such as an aromatic amine compound, a carbazole derivative, aromatic hydrocarbon, and a high molecular compound (an oligomer, a dendrimer, a polymer, or the like) can be given. An organic compound having a hole mobility of $10^{-6}$ cm$^2$/Vs or higher is preferably used as a hole-transporting organic compound. Note that any organic compound other than the above substances may also be used as long as its hole-transporting property is higher than its electron-transporting property. The composite material of an organic compound and a metal oxide is excellent in a carrier-injecting property and a carrier-transporting property; therefore, low-voltage driving and low-current driving can be achieved.

Note that the charge generation layer 513 may be formed by a combination of a composite material of an organic compound and a metal oxide and another material. For example, a layer containing the composite material of an organic compound and a metal oxide may be used in combination with a layer containing a compound selected from electron-donating substances and a compound having a high electron-transporting property. Further, a layer containing the composite material of an organic compound and a metal oxide may be used in combination with a transparent conductive film.

In any case, any layer can be employed as the charge generation layer 513 interposed between the first light-emitting unit 511 and the second light-emitting unit 512 as long as the layer injects electrons into one of these light-emitting units and holes into the other when voltage is applied to the first electrode 501 and the second electrode 502.

Although the light-emitting element having two light-emitting units is described in this embodiment, a light-emitting element in which three or more light-emitting units are stacked can be employed in a similar way. When a charge generation layer is provided between a pair of electrodes so as to partition plural light-emitting units as in the light-emitting element of this embodiment, the element can have a long lifetime in a high luminance region while the current density is kept low. Further, in the case where the light-emitting element is applied to lighting, voltage drop due to resistance of an electrode material can be reduced. Accordingly, light can be uniformly emitted from a large area. Moreover, a light-emitting device of low power consumption which can be driven at low voltage can be achieved.

Note that this embodiment can be implemented in combination with any of the other embodiments as appropriate.

Embodiment 5

In this embodiment, one mode of a light-emitting device manufactured using the oxadiazole derivative of the present invention will be described.

In this embodiment, a light-emitting device manufactured using the oxadiazole derivative of the present invention will be described with reference to FIGS. 4A and 4B. Note that FIG. 4A is a top view of the light-emitting device, and FIG. 4B is a cross-sectional view taken along lines A-B and C-D of FIG. 4A. Reference numerals 601, 602, and 603 denote a driver circuit portion (a source side driver circuit), a pixel portion, and a driver circuit portion (a gate side driver circuit), respectively, which are indicated by dotted lines. Further, reference numeral 604 denotes a sealing substrate and reference numeral 605 denotes a sealant. A portion surrounded by the sealant 605 is a space 607.

Note that a lead wiring 608 is a wiring for transmitting signals to be input into the source side driver circuit 601 and the gate side driver circuit 603 and for receiving signals such as a video signal, a clock signal, a start signal, and a reset signal from an FPC (flexible printed circuit) 609 serving as an external input terminal. Although only the FPC is illustrated here, this FPC may be provided with a printed wiring board (PWB). The light-emitting device in this specification refers to not only a light-emitting device itself but also a light-emitting device provided with an FPC or a PWB.

Next, a cross-sectional structure is described with reference to FIG. 4B. Of the driver circuit portions and the pixel portion over an element substrate 610, the source side driver circuit 601, which is a driver circuit portion, and one pixel in the pixel portion 602 are illustrated here.

Note that a CMOS circuit in which an n-channel TFT 623 and a p-channel TFT 624 are formed in combination is formed in the source side driver circuit 601. The driver circuit may be formed using a variety of circuits including a TFT, such as a CMOS circuit, a PMOS circuit, or a NMOS circuit. Although the driver integrated device which has the driver circuit formed over the substrate is described in this embodiment, the driver circuit does not always have to be formed over the substrate. It is also possible to form the driver circuit not over the substrate but outside the substrate.

Moreover, the pixel portion 602 includes a plurality of pixels including a switching TFT 611, a current control TFT 612, and a first electrode 613 electrically connected to a drain of the current control TFT 612. Note that an insulator 614 is formed covering an end portion of the first electrode 613. Here, a positive photosensitive acrylic resin film is used for the insulator 614.

In order to improve the coverage, the insulator 614 is formed to have a curved surface with a curvature at its upper or lower end portion. For example, in the case of using positive photosensitive acrylic as a material for the insulator 614, only the upper end portion of the insulator 614 preferably has a curved surface with a radius of curvature (0.2 μm to 3 μm). Further, the insulator 614 can be formed using either a negative type that becomes insoluble in an etchant by light irradiation or a positive type that becomes soluble in an etchant by light irradiation.

A layer 616 containing a light-emitting substance and a second electrode 617 are formed over the first electrode 613. Here, the first electrode 613 serving as an anode is preferably formed using a material with a high work function. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like can be used. Alternatively, a stack of a titanium nitride film and a film containing aluminum as its main component, a stack of three layers of a titanium nitride film, a film containing aluminum as its main component, and a titanium nitride film, or the like can be used. Note that when the first electrode 613 has a stacked structure, low resistance as a wiring, a good ohmic contact, and a function as an anode can be achieved.

The layer 616 containing a light-emitting substance is formed by any of a variety of methods such as an evaporation method using an evaporation mask, a droplet discharge method such as an inkjet method, a printing method, and a spin coating method. The layer 616 containing a light-emitting substance contains any of the oxadiazole derivatives described in Embodiment 1 of the present invention. As another material contained in the layer 616 containing a light-emitting substance, a low molecular material, a medium molecular material (including an oligomer and a dendrimer), or a high molecular material may be used.

Further, as a material used for the second electrode 617, which is formed over the layer 616 containing a light-emitting substance and functions as a cathode, a material having a low work function (Al, Mg, Li, Ca, or an alloy or a compound thereof such as MgAg, MgIn, AlLi, LiF, or $CaF_2$) is preferably used. In the case where light generated in the layer 616 containing a light-emitting substance passes through the second electrode 617, the second electrode 617 is preferably formed using a stack of a thin metal film having a reduced thickness and a transparent conductive film (such as ITO, indium oxide containing zinc oxide at 2 wt % to 20 wt %, indium tin oxide containing silicon or silicon oxide, or zinc oxide (ZnO)).

By attaching the sealing substrate 604 to the element substrate 610 using the sealant 605, the light-emitting element 618 is provided in the space 607 which is surrounded by the element substrate 610, the sealing substrate 604, and the sealant 605. Note that the space 607 is filled with filler. The space may be filled with an inert gas (such as nitrogen or argon) or the sealant 605.

Note that an epoxy-based resin is preferably used for the sealant 605. In addition, it is desirable to use a material that allows permeation of moisture or oxygen as little as possible. As the sealing substrate 604, a plastic substrate formed from fiberglass-reinforced plastics (FRP), polyvinyl fluoride (PVF), polyester, acrylic, or the like can be used besides a glass substrate or a quartz substrate.

In this manner, the light-emitting device manufactured using the oxadiazole derivative of the present invention can be obtained.

The oxadiazole derivative of the present invention has a large band gap and is a bipolar material which allows both a hole and an electron to flow.

Further, by using the oxadiazole derivative of the present invention, a light-emitting element, a light-emitting device, and an electronic device with lower power consumption can be obtained.

Figure 5A:
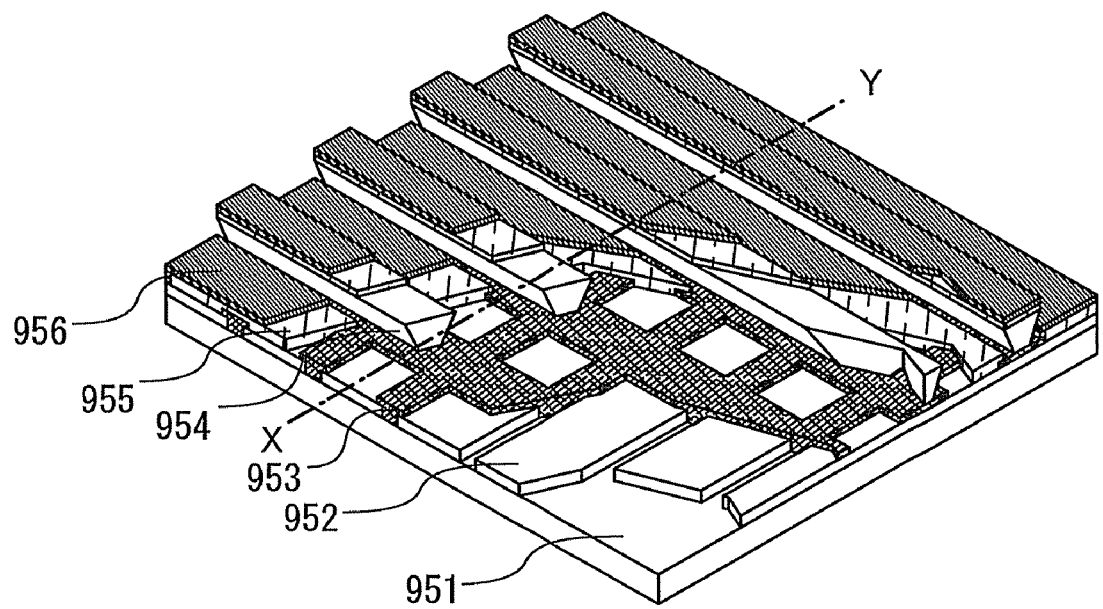
FIGS. 5A and 5B are views illustrating a light-emitting device.
Figure 5B:
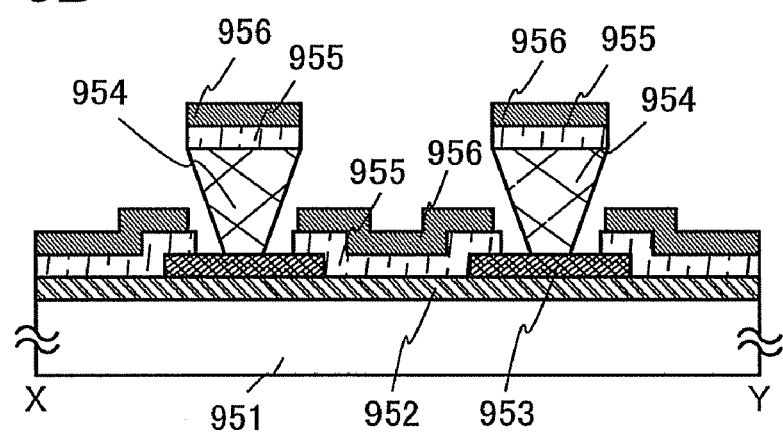

Although an active matrix light-emitting device in which operation of a light-emitting element is controlled with a transistor is described in this embodiment, a passive matrix light-emitting device may alternatively be used. FIG. 5A is a perspective view of a passive matrix light-emitting device manufactured by applying the present invention, and FIG. 5B is a cross-sectional view taken along line X-Y in FIG. 5A. In FIGS. 5A and 5B, a layer 955 containing a light-emitting substance is provided over a substrate 951 and between an electrode 952 and an electrode 956. An edge portion of the electrode 952 is covered with an insulating layer 953. A partition layer 954 is provided over the insulating layer 953. The sidewalls of the partition layer 954 are aslope so that the distance between the sidewalls is gradually reduced toward the surface of the substrate. That is, a cross section in a short-side direction of the partition layer 954 is a trapezoidal shape, and the bottom side (the side which faces a direction similar to a plane direction of the insulating layer 953 and is in contact with the insulating layer 953) of the trapezoid is shorter than the top side (the side which faces a direction similar to the plane direction of the insulating layer 953 and is not in contact with the insulating layer 953). By the provision of the partition layer 954 in this manner, defects of the light-emitting element due to static charge or the like can be prevented. A passive matrix light-emitting device can also have high reliability when including the light-emitting element disclosed by one mode of the present invention.

Embodiment 6

In this embodiment, examples of an electronic device of the present invention which includes a light-emitting device described in Embodiment 4 will be described. Electronic devices according to the present invention include any of the oxadiazole derivatives which are described in Embodiment 1 and have a display portion having low power consumption.

Examples of electronic devices which include a light-emitting element manufactured using the oxadiazole derivative of the present invention include cameras such as video cameras or digital cameras, goggle type displays, navigation systems, audio playback devices (e.g., car audio systems, audio component, and the like), computers, game machines, portable information terminals (e.g., mobile computers, cellular phones, portable game machines, and electronic books), image playback devices provided with recording media (devices that are capable of playing back recording media such as digital versatile discs (DVDs) and equipped with display devices that can display the image), and the like. Some specific examples thereof are illustrated in FIGS. 6A to 6E.

Figure 6A:
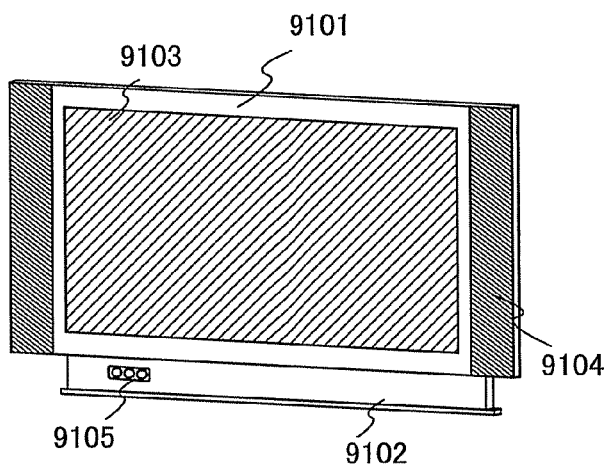
FIGS. 6A to 6E are views each illustrating an electronic device.

FIG. 6A illustrates a television device according to the present invention. The television device includes a housing 9101, a supporting base 9102, a display portion 9103, a speaker portion 9104, a video input terminal 9105, and the like. In the display portion 9103 of this television device, light-emitting elements similar to those described in Embodiment 2 or 3 are arranged in a matrix. The light-emitting elements have a feature of low power consumption. Accordingly, the display portion 9103 which includes the light-emitting elements has similar features. Therefore, this television device can achieve low power consumption. Thus, a product which is suitable for living environment can be provided.

Figure 6B:
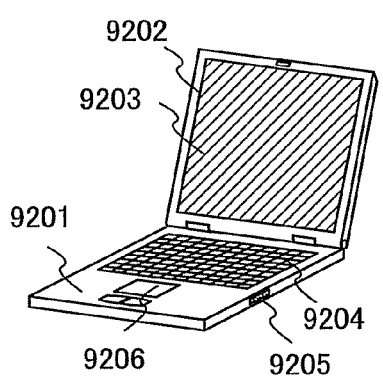

FIG. 6B illustrates a computer according to the present invention. The computer includes a main body 9201, a housing 9202, a display portion 9203, a keyboard 9204, an external connection port 9205, a pointing device 9206, and the like. In the display portion 9203 of this computer, light-emitting elements similar to those described in Embodiment 2 or 3 are arranged in a matrix. The light-emitting elements have a feature of low power consumption. Accordingly, the display portion 9203 which includes the light-emitting elements has similar features. Therefore, this computer can achieve low power consumption. Thus, a product which is suitable for environment can be provided.

Figure 6C:
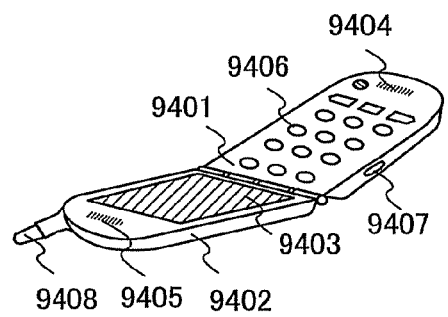

FIG. 6C illustrates a cellular phone according to the present invention. The cellular phone includes a main body 9401, a housing 9402, a display portion 9403, an audio input portion 9404, an audio output portion 9405, operation keys 9406, an external connection port 9407, an antenna 9408, and the like. In the display portion 9403 of the cellular phone, light-emitting elements similar to those described in Embodiment 2 or 3 are arranged in a matrix. The light-emitting elements have a feature of low power consumption. Accordingly, the display portion 9403 which includes the light-emitting elements has similar features. Therefore, the cellular phone can achieve low power consumption. Thus, a product which is suitable for being carried around can be provided.

Figure 6D:
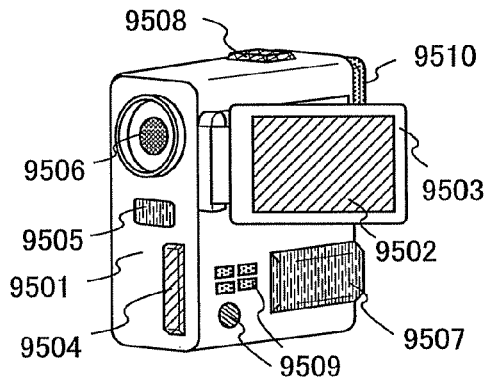
Figure 6E:
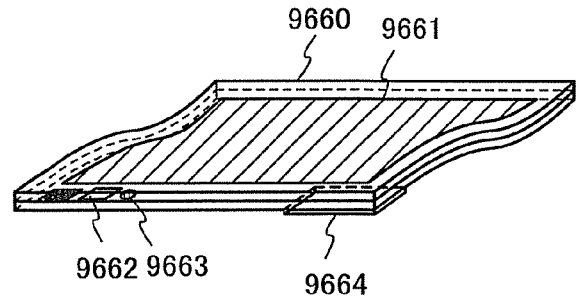

FIG. 6D illustrates a camera according to the present invention. The camera includes a main body 9501, a display portion 9502, a housing 9503, an external connection port 9504, a remote control receiving portion 9505, an image receiving portion 9506, a battery 9507, an audio input portion 9508, operation keys 9509, an eye piece portion 9510, and the like. In the display portion 9502 of the camera, light-emitting elements similar to those described in Embodiment 2 or 3 are arranged in a matrix. The light-emitting elements have a feature of low power consumption. Accordingly, the display portion 9502 which includes the light-emitting elements has similar features. Therefore, this camera can achieve low power consumption. Thus, a product which is suitable for being carried around can be provided.

As described above, the applicable range of the light-emitting device of the present invention is so wide that the light-emitting device can be applied to electronic devices in a variety of fields. By using any of the oxadiazole derivatives of the present invention, an electronic device having a display portion with low power consumption can be provided.

The light-emitting device of the present invention can also be used as a lighting device. An example in which the light-emitting device of the present invention is used as a lighting device will be described with reference to FIG. 7.

Figure 7:
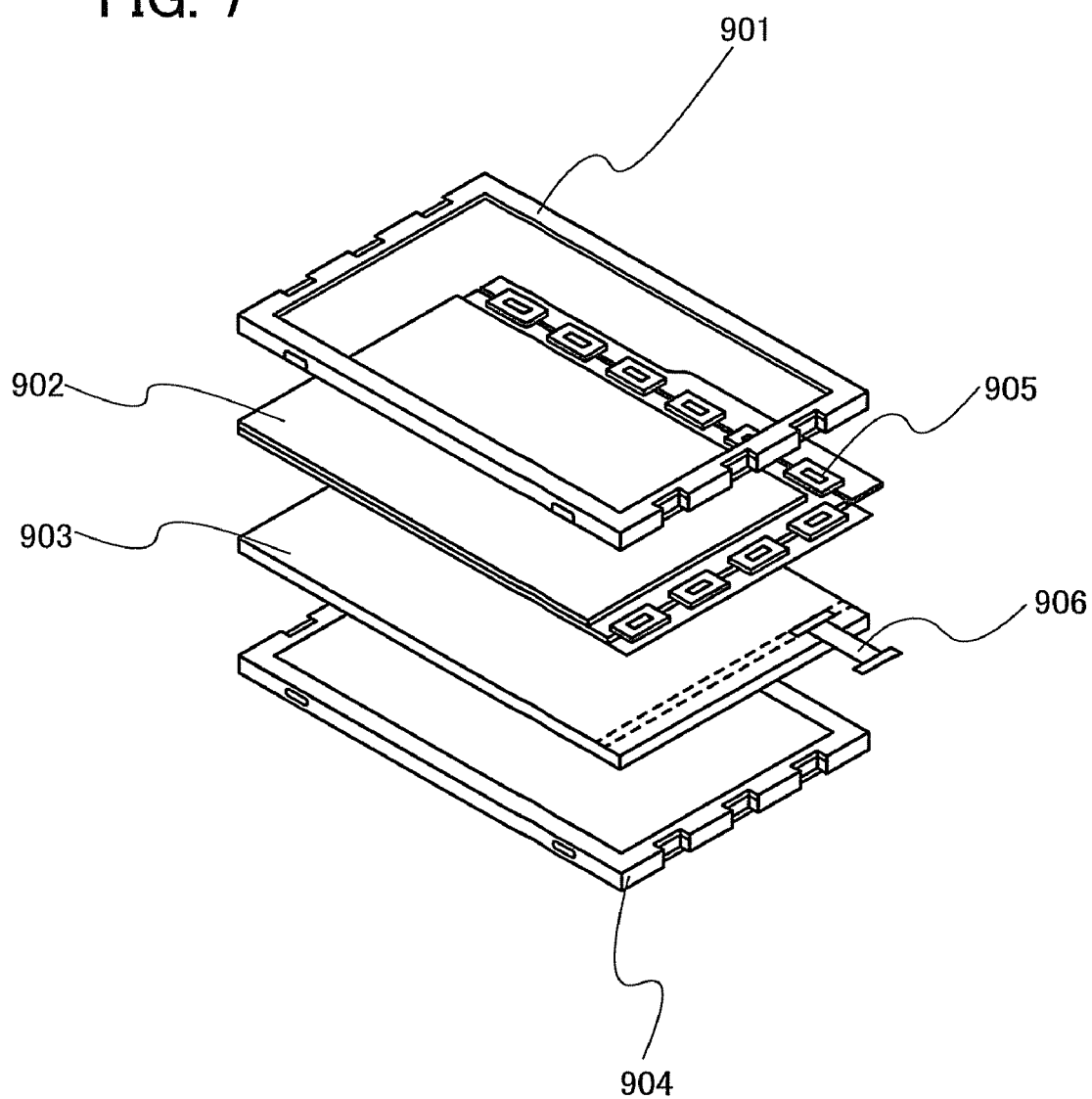
FIG. 7 is a view illustrating an electronic device.

FIG. 7 illustrates an example of a liquid crystal display device using a light-emitting device of the present invention as a backlight. The liquid crystal display device illustrated in FIG. 7 includes a housing 901, a liquid crystal layer 902, a backlight 903, and a housing 904. The liquid crystal layer 902 is connected to a driver IC 905. The light-emitting device of the present invention is used as the backlight 903 to which current is supplied through a terminal 906.

By using the light-emitting device of the present invention for a backlight of a liquid crystal display device, a highly reliable backlight can be obtained. Further, the light-emitting device of the present invention can be applied to a lighting device of plane light emission and can have a large area. Therefore, the backlight can have a large area, and a liquid crystal display device having a large area can be obtained. Furthermore, since the light-emitting device of the present invention is thin, the thickness of a display device can also be reduced.

Figure 8A:
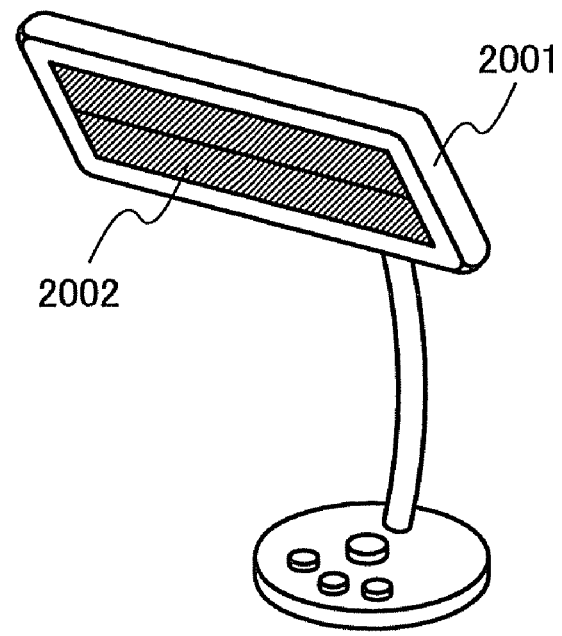
FIGS. 8A and 8B are views each illustrating a lighting device.
Figure 8B:
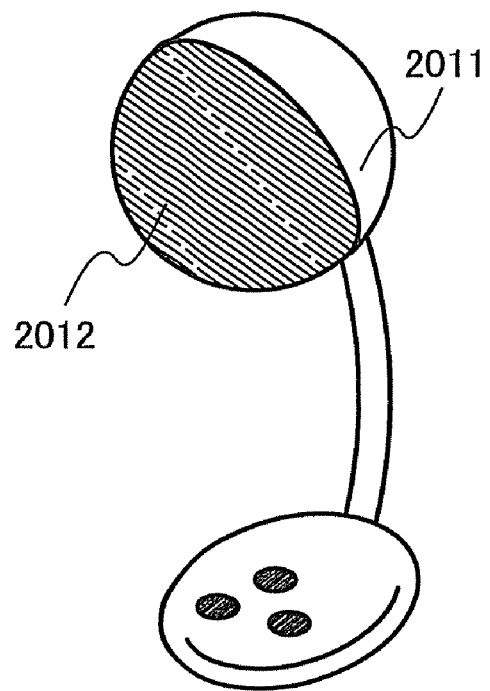

FIGS. 8A and 8B illustrate examples in which a light-emitting device to which the present invention is applied is used as a table lamp, which is a kind of lighting device. The table lamp illustrated in FIG. 8A includes a housing 2001 and a light source 2002, and the table lamp illustrated in FIG. 8B includes a housing 2011 and a light source 2012. The light-emitting device of the present invention is used as the light source 2002 and the light source 2012. Since the light-emitting device of the present invention has low power consumption, the table lamps can also achieve low power consumption.

Figure 9:
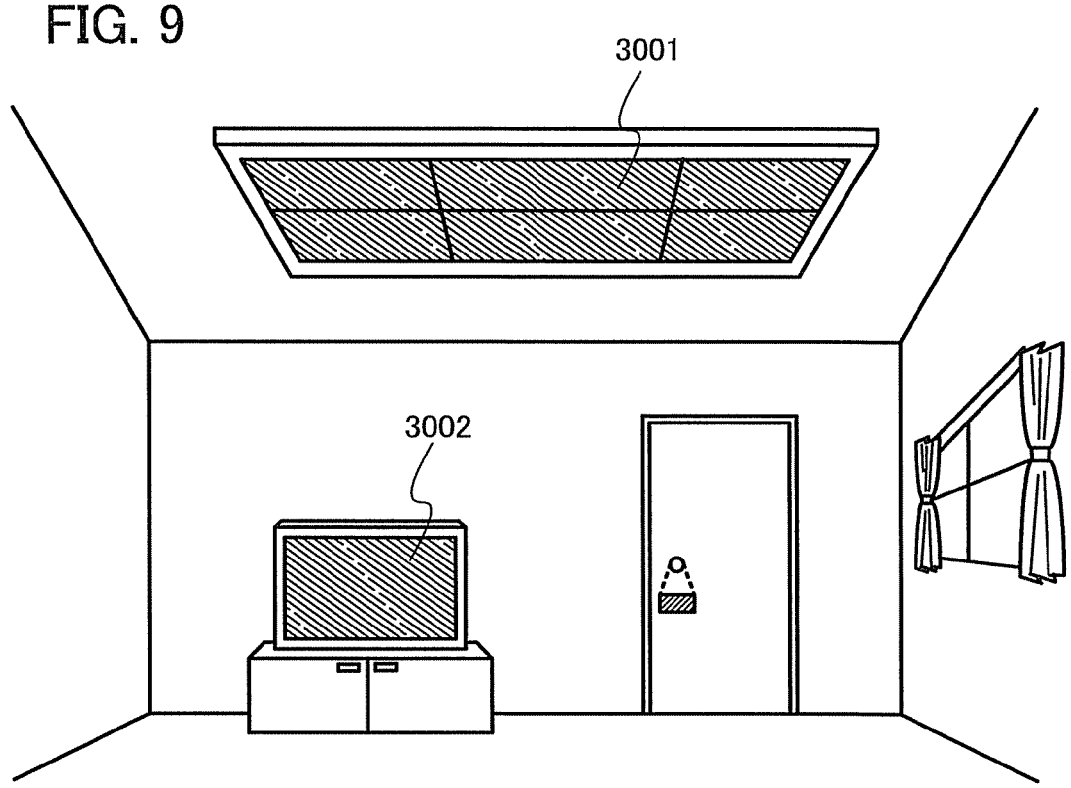
FIG. 9 is a view illustrating a lighting device.

FIG. 9 illustrates an example in which a light-emitting device to which the present invention is applied is used as an indoor lighting device 3001. Since the light-emitting device of the present invention can have a large area, the light-emitting device can be used as a large-area lighting device. Further, since the light-emitting device of the present invention is thin, the light-emitting device of the present invention can be used as a lighting device having a reduced thickness. In a room where the light-emitting device to which the present invention is applied is used as the indoor lighting device 3001 in this manner, a television device 3002 according to the present invention, which is similar to the one illustrated in FIG. 6A, can be placed so that public broadcasting and movies can be enjoyed.

Example 1

In Example 1, a synthesis method of 9-[4-(3-phenyl-1,2,4-oxadiazol-5-yl)phenyl]-9H-carbazole (abbreviated to CzOd) represented by Structural Formula (100), which is an oxadiazole derivative of the present invention, will be described specifically.

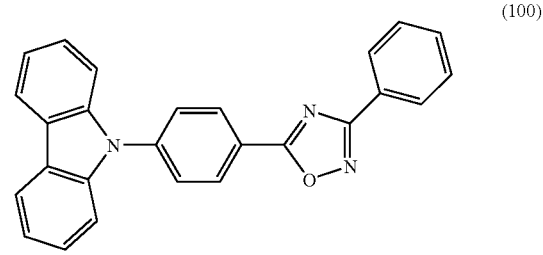

(100)

A synthesis scheme of CzOd (abbreviation) is shown in (A-1).

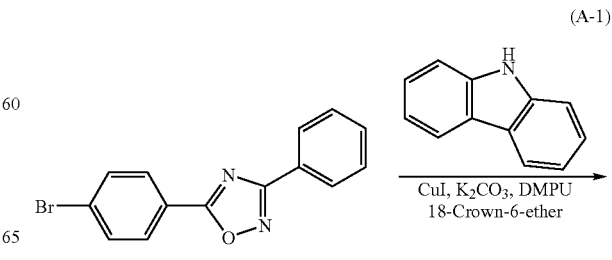

(A-1)

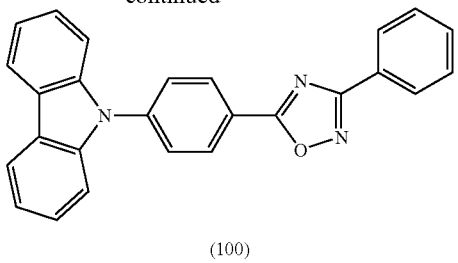

(100)

In a 100 mL three-neck flask, 2.0 g (6.6 mmol) of 5-(4-bromophenyl)-3-phenyl-1,2,4-oxadiazole, 1.3 g (13 mmol) of sodium tert-butoxide, 1.1 g (6.6 mmol) of 9H-carbazole, and 0.10 g (0.20 mmol) of bis(dibenzylideneacetone)palladium(0) were placed, and the air in the flask was replaced with nitrogen. Then, 40 mL of toluene and 0.01 mL of tri-tert-butylphosphine 10 wt % hexane solution were added into this mixture. After this mixture was degassed under low pressure, the air in the flask was replaced with nitrogen. The mixture was stirred at 80° C. for 20 hours under a nitrogen gas stream. After the stirring, toluene was added into the mixture, and the resulting suspension was suction filtered through Celite (manufactured by Wako Pure Chemical Industries, Ltd., Catalog No. 531-16855) to give a filtrate. The filtrate was washed with water and brine. Then, the organic layer was dried with magnesium sulfate. After the drying, this mixture was suction filtered. The resulting filtrate was concentrated to give a compound, and the compound was purified by silica gel column chromatography. The column chromatography was performed first using a mixed solvent of a 1:2 ratio of toluene to hexane as a developing solvent and then using toluene as a developing solvent. The solid which was obtained by concentrating the obtained fraction was recrystallized with a mixed solvent of chloroform and methanol to give 1.9 g of an objective white solid in a yield of 49%.

Further, 1.3 g of the solid obtained was purified by sublimation by a train sublimation method. The sublimation purification was carried out at 190° C. for 16 hours under a reduced pressure of 7.0 Pa with a flow rate of argon at 3.0 mL/min. After the sublimation purification, 1.1 g of a solid which is CzOd (abbreviation) was obtained in 87% yield.

Next, by a nuclear magnetic resonance (NMR) method, the compound obtained by the above-described synthesis method was confirmed to be 9-[4-(3-phenyl-1,2,4-oxadiazol-5-yl)phenyl]-9H-carbazole (abbreviated to CzOd), which was the desired compound.

The following are data of the $^1$H NMR of the obtained compound: $^1$H NMR (CDCl$_3$, 300 MHz): δ=7.30-7.37 (m, 2H), 7.41-7.58 (m, 7H), 7.81 (d, J=7.8 Hz, 2H), 8.16 (d, J=7.3 Hz, 2H), 8.19-8.24 (m, 2H), 8.47 (d, J=8.3 Hz, 2H).

Figure 12A:
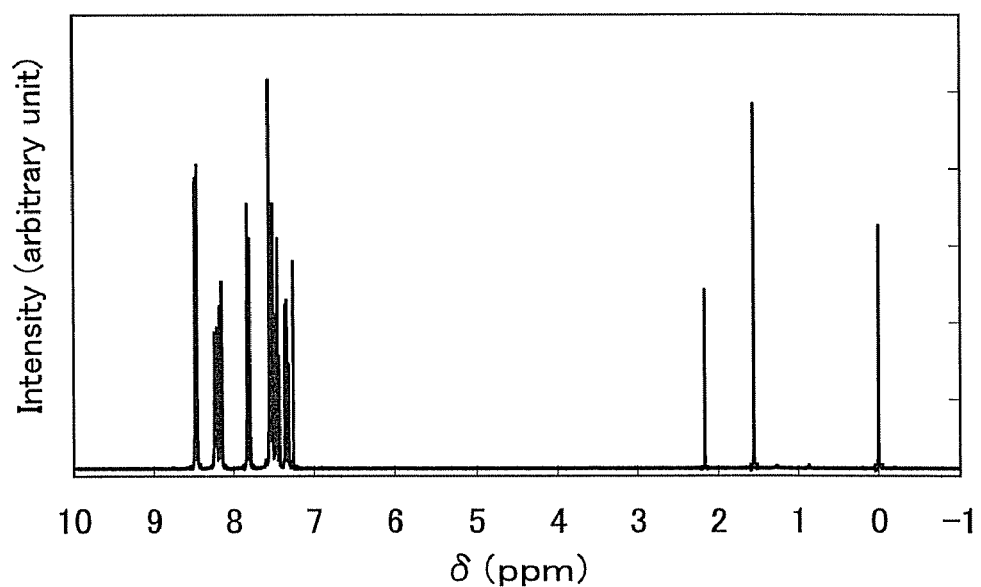
FIGS. 12A and 12B are graphs showing $^1$H NMR charts of CzOd (abbreviation)
Figure 12B:
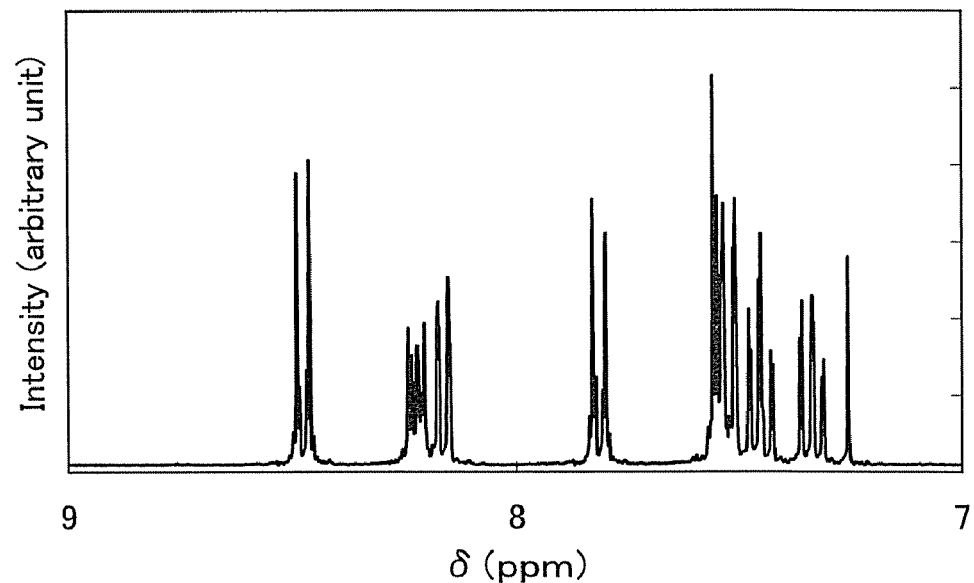

In addition, FIGS. 12A and 12B show $^1$H NMR charts. Note that FIG. 12B is an enlarged chart showing the range from 7.0 ppm to 9.0 ppm in FIG. 12A.

Figure 13:
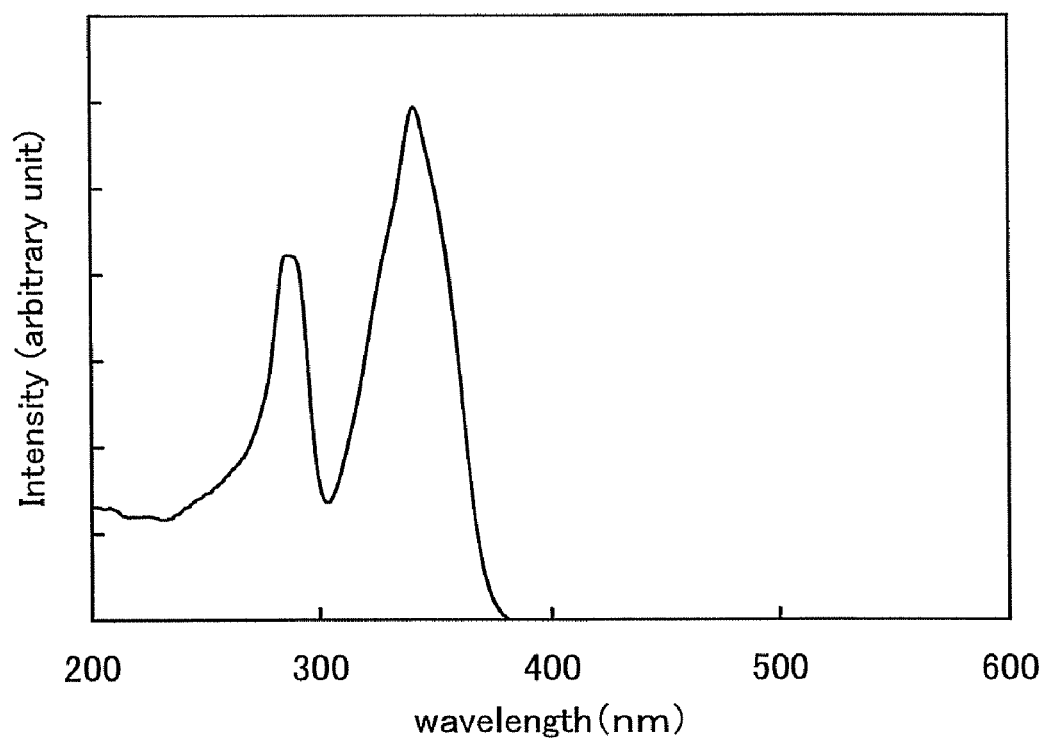
FIG. 13 shows an absorption spectrum of a toluene solution of CzOd (abbreviation)
Figure 14:
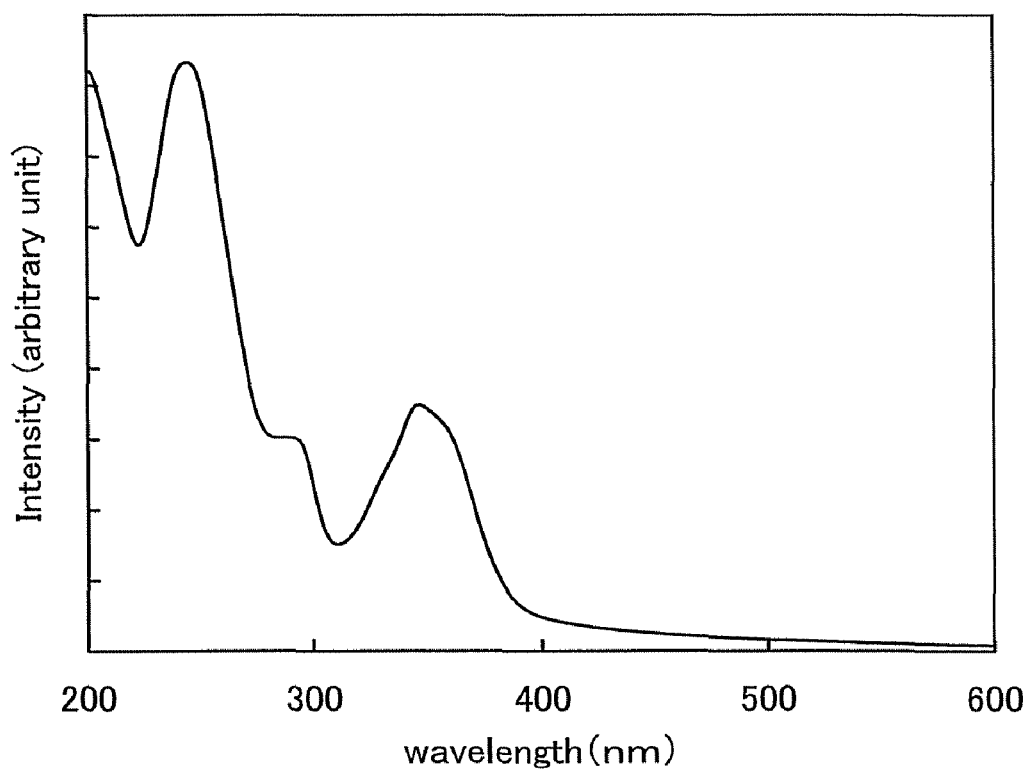
FIG. 14 shows an absorption spectrum of a thin film of CzOd (abbreviation)
Figure 15:
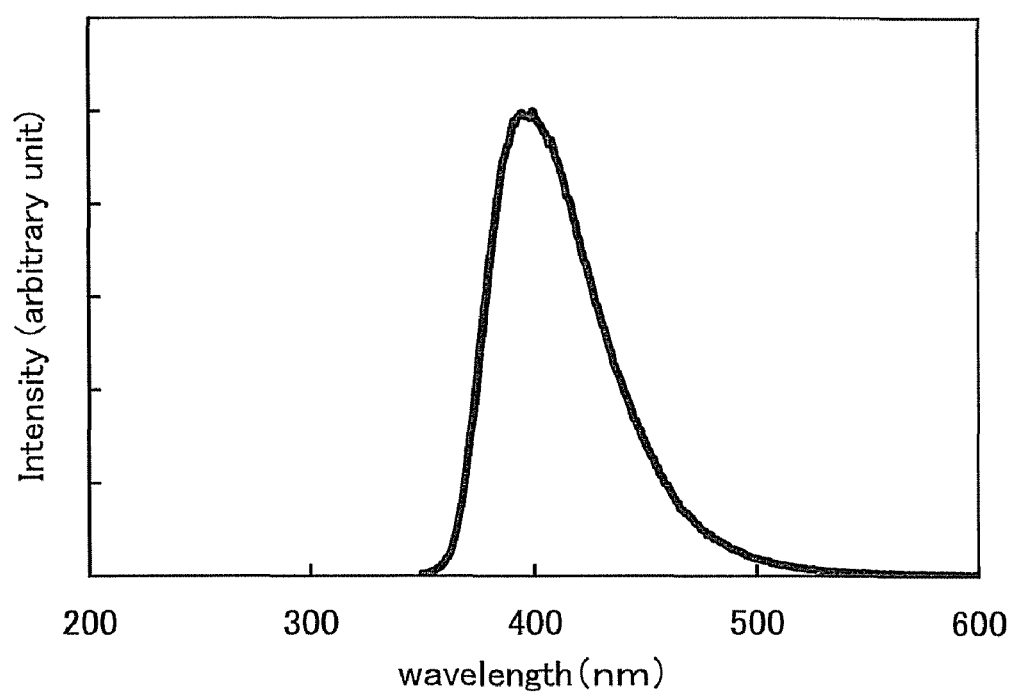
FIG. 15 shows an emission spectrum of a toluene solution of CzOd (abbreviation)
Figure 16:
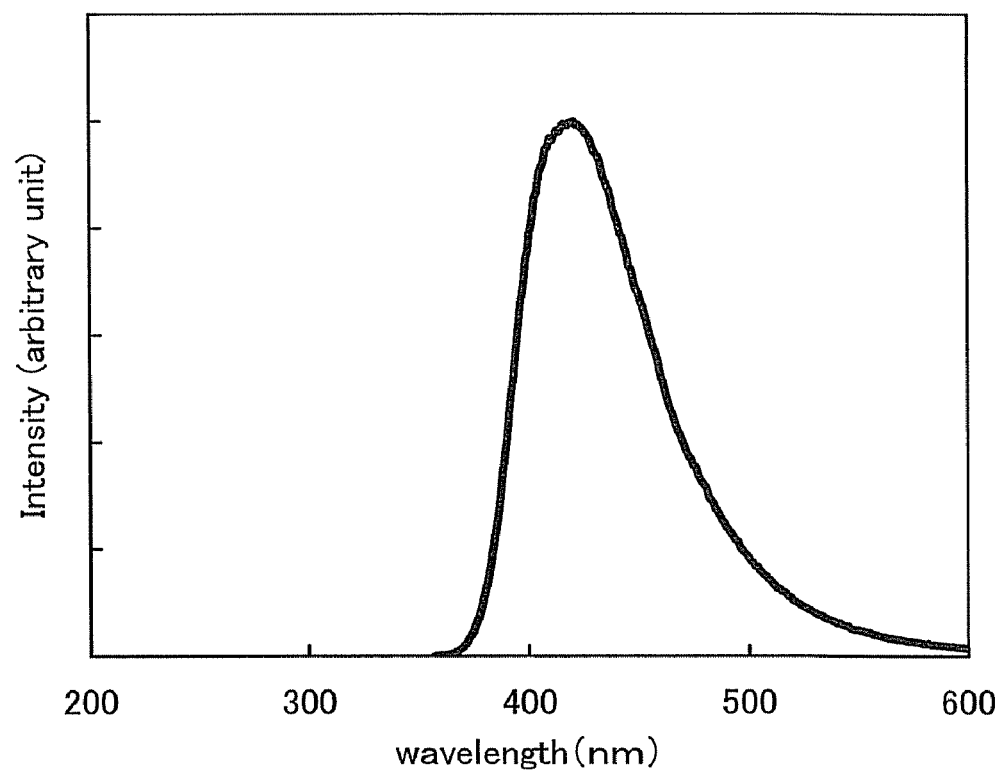
FIG. 16 shows an emission spectrum of a thin film of CzOd (abbreviation)

FIG. 13 and FIG. 15 show an absorption spectrum and an emission spectrum, respectively, of a toluene solution of CzOd (abbreviation). FIG. 14 and FIG. 16 show an absorption spectrum and an emission spectrum, respectively, of a thin film of CzOd (abbreviation). An ultraviolet-visible spectrophotometer (V-550, manufactured by JASCO Corporation) was used for the measurement of the absorption spectrum. To prepare samples, the solution was put in a quartz cell while the thin film was obtained by evaporation onto a quartz substrate. As for the absorption spectrum of the solution, the absorption spectrum obtained by subtraction of the absorption spectra of the quartz cell and toluene is shown in FIG. 13. As for the spectrum of the thin film, the absorption spectrum obtained by subtraction of the absorption spectrum of the quartz substrate is shown in FIG. 14. In FIG. 13, FIG. 14, FIG. 15, and FIG. 16, the horizontal axis indicates wavelength (nm) and the vertical axis indicates intensity (arbitrary unit). In the case of the toluene solution, absorption was observed at around 340 nm, and the maximum emission wavelength was 400 nm (excitation wavelength: 345 nm). In the case of the thin film, absorption was observed at around 347 nm, and the maximum emission wavelength was 423 nm (excitation wavelength: 347 nm).

Further, the HOMO level and LUMO level of CzOd (abbreviation) in the thin film state were measured. The value of the HOMO level was obtained by conversion of a value of ionization potential measured with a photoelectron spectrometer (AC-2, manufactured by Riken Keiki Co., Ltd.) in the atmosphere into a negative value. The value of the LUMO level was obtained in such a manner that the absorption edge was obtained from Tauc plot, with an assumption of direct transition, using data on the absorption spectrum of the thin film of CzOd (abbreviation) in FIG. 14, and the obtained absorption edge was added to the HOMO level as an optical energy gap. As a result, the HOMO level and LUMO level of CzOd (abbreviation) were found to be −5.93 eV and −2.76 eV, respectively, and the energy gap was found to be 3.17 eV.

Thus, CzOd (abbreviation) is found to have a large energy gap.

In addition, the optimal molecular structure of CzOd (abbreviation) in the ground state was calculated using the density functional theory (DFT). In the DFT, the total energy is represented as the sum of potential energy, electrostatic energy between electrons, electronic kinetic energy, and exchange-correlation energy including all the complicated interactions between electrons. Also in the DFT, an exchange-correlation interaction is approximated by a functional (that is, a function of another function) of one electron potential represented in terms of electron density to enable high-speed and highly-accurate calculations. Here, B3LYP which was a hybrid functional was used to specify the weight of each parameter related to exchange-correlation energy. In addition, as a basis function, 6-311 (a basis function of a triple-split valence basis set using three contraction functions for each valence orbital) was applied to all the atoms. By the above basis function, for example, orbits of 1s to 3s are considered in the case of hydrogen atoms while orbits of 1s to 4s and 2p to 4p are considered in the case of carbon atoms. Furthermore, to improve calculation accuracy, the p function and the d function as polarization basis sets were added to hydrogen atoms and atoms other than hydrogen atoms, respectively.

Note that Gaussian 03 was used as a quantum chemistry computational program. A high performance computer (Altix 4700, manufactured by SGI Japan, Ltd.) was used for the calculations.

Figure 31A:
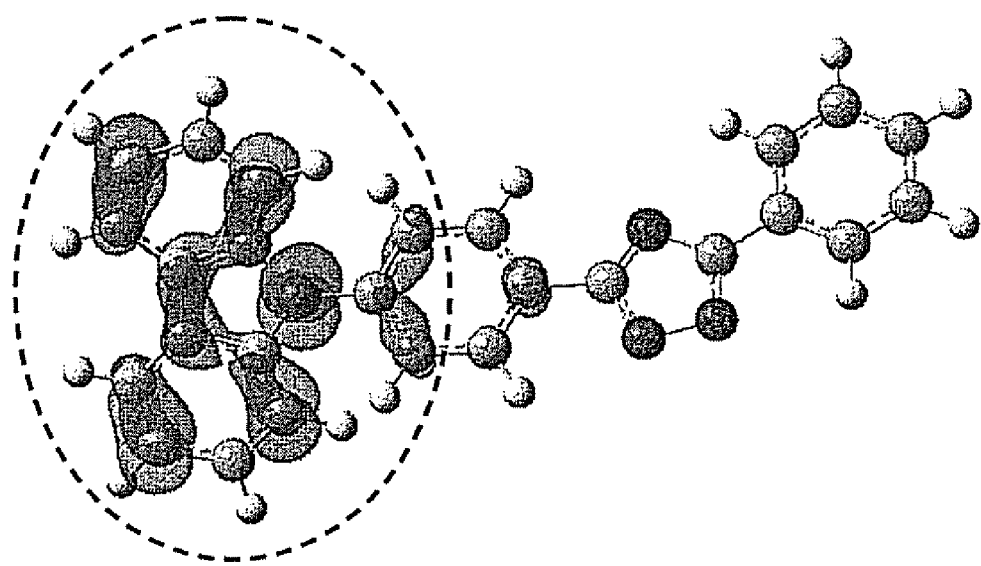
FIGS. 31A and 31B show the highest occupied molecular orbital (HOMO) and lowest unoccupied molecular orbital (LUMO) of CzOd (abbreviation), respectively.
Figure 31B:
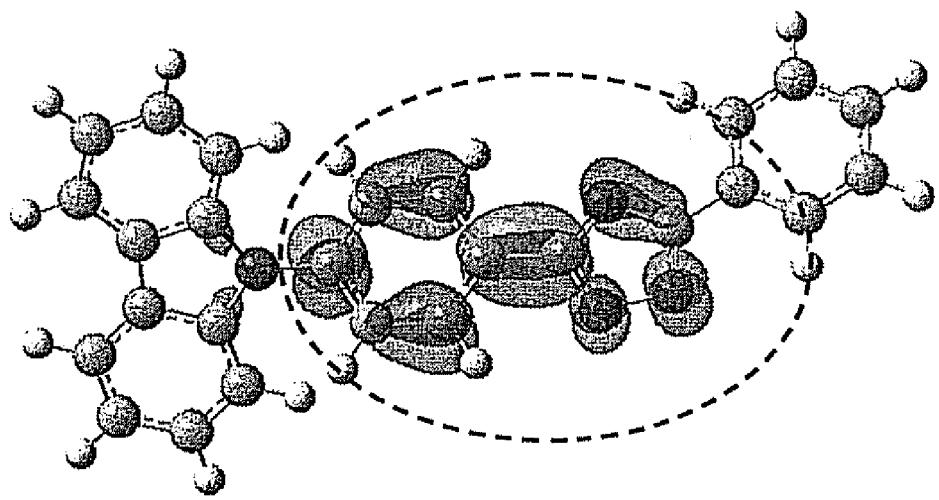

FIGS. 31A and 31B show respectively the highest occupied molecular orbital (HOMO) and lowest unoccupied molecular orbital (LUMO) of CzOd (abbreviation), which were found by the calculations. FIG. 31A shows the highest occupied molecular orbital (HOMO), and FIG. 31B shows the lowest unoccupied molecular orbital (LUMO). In the drawings, the spheres represent atoms forming CzOd (abbreviation) and cloud-like objects around atoms represent orbits. Note that FIGS. 31A and 31B are visualization views of calculation results of the optimal molecular structures obtained by GaussView 4.1, which is software visualizing computational results.

FIGS. 31A and 31B reveal that the highest occupied molecular orbital and lowest unoccupied molecular orbital of CzOd (abbreviation) exist in a carbazole group and an oxadiazole group, respectively. In other words, the carbazole group contributes to the hole-transporting property of CzOd (abbreviation) while the oxadiazole group contributes to the electron-transporting property thereof. The carbazole group is a unit exhibiting a high hole-transporting property, and the oxadiazole group is a unit exhibiting a high electron-transporting property, which proves the high bipolar property of CzOd (abbreviation).

Example 2

In Example 2, a synthesis method of 9-[3-(3-phenyl-1,2,4-oxadiazol-5-yl)phenyl]-9H-carbazole (abbreviated to mCzOd) represented by Structural Formula (135), which is an oxadiazole derivative of the present invention, will be described specifically.

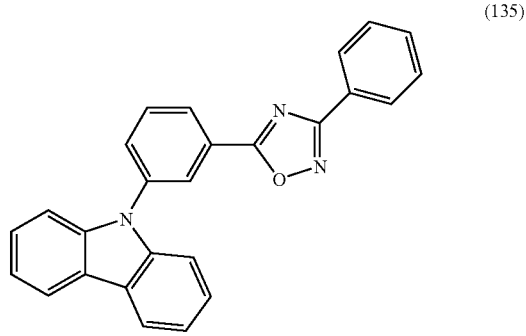

(135)

A synthesis scheme of mCzOd (abbreviation) is shown in (B-1).

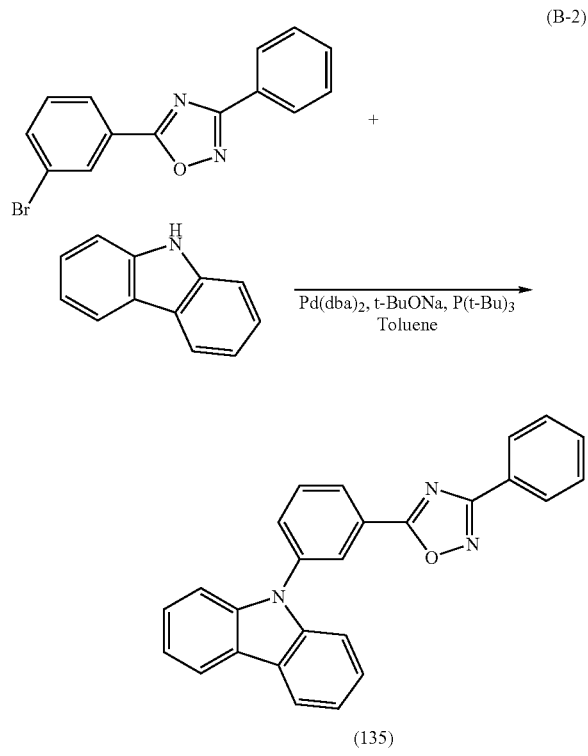

(B-2)

(135)

In a 100 mL three-neck flask, 2.0 g (6.6 mmol) of 5-(3-bromophenyl)-3-phenyl-1,2,4-oxadiazole, 1.3 g (13 mmol) of sodium tert-butoxide, 1.1 g (6.6 mmol) of 9H-carbazole, and 0.10 g (0.20 mmol) of bis(dibenzylideneacetone)palladium(0) were placed, and the air in the flask was replaced with nitrogen. Then, 40 mL of toluene and 0.010 mL of tri-tert-butylphosphine 10 wt % hexane solution were added into this mixture. This mixture was stirred at 80° C. for 8 hours under a nitrogen gas stream. After the stirring, toluene was added into the mixture, and the resulting suspension was suction filtered through Florisil (produced by Wako Pure Chemical Industries, Ltd., Catalog No. 540-00135), Celite (manufactured by Wako Pure Chemical Industries, Ltd., Catalog No. 531-16855), and alumina to give a filtrate. The filtrate was washed with water and brine. Then, the organic layer was dried with magnesium sulfate. After the drying, this mixture was suction filtered. The resulting filtrate was concentrated to give a compound, and the compound was purified by silica gel column chromatography. The column chromatography was performed first using a mixed solvent of a 1:2 ratio of toluene to hexane as a developing solvent and then using toluene as a developing solvent. The solid which was obtained by concentrating the obtained fraction was recrystallized with a mixed solvent of chloroform and methanol to give 1.9 g of a white powdery solid in a yield of 49%.

Further, 1.2 g of the solid obtained was purified by sublimation by a train sublimation method. The sublimation purification was carried out at 190° C. for 25 hours under a reduced pressure of 7.0 Pa with a flow rate of argon at 3.0 mL/min. After the sublimation purification, 0.50 g of a solid which is mCzOd (abbreviation) was obtained in 41% yield.

Next, by a nuclear magnetic resonance (NMR) method, the compound obtained by the above-described synthesis method was confirmed to be 9-[3-(3-phenyl-1,2,4-oxadiazol-5-yl)phenyl]-9H-carbazole (abbreviated to mCzOd), which was the desired compound.

The following are data of the $^1$H NMR of the obtained compound: $^1$H NMR (CDCl$_3$, 300 MHz): δ=7.27-7.52 (m, 9H), 7.72-7.83 (m, 2H), 8.12-8.18 (m, 4H), 8.25-8.30 (m, 1H), 8.45 (s, 1H).

Figure 17A:
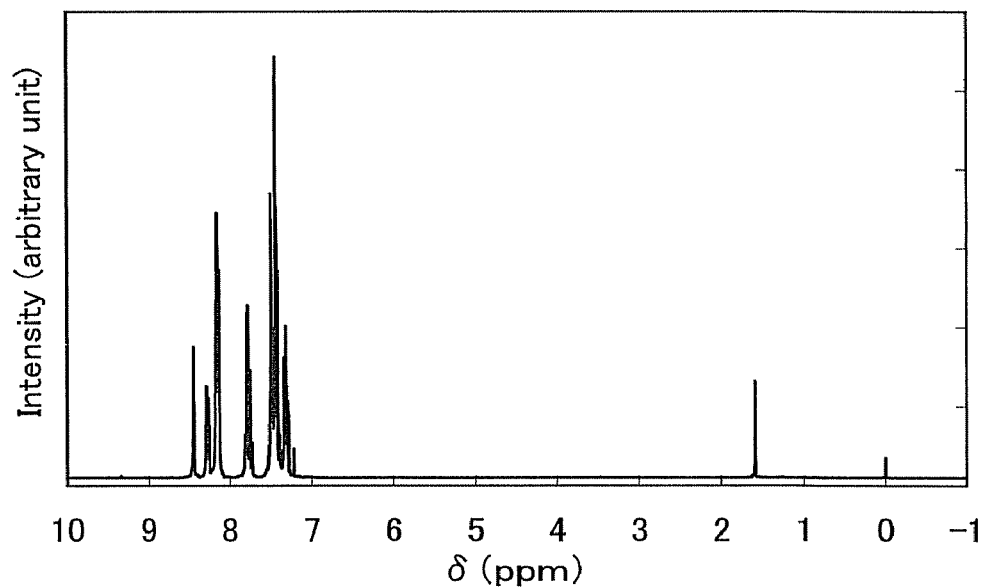
FIGS. 17A and 17B are graphs showing $^1$H NMR charts of mCzOd (abbreviation)
Figure 17B:
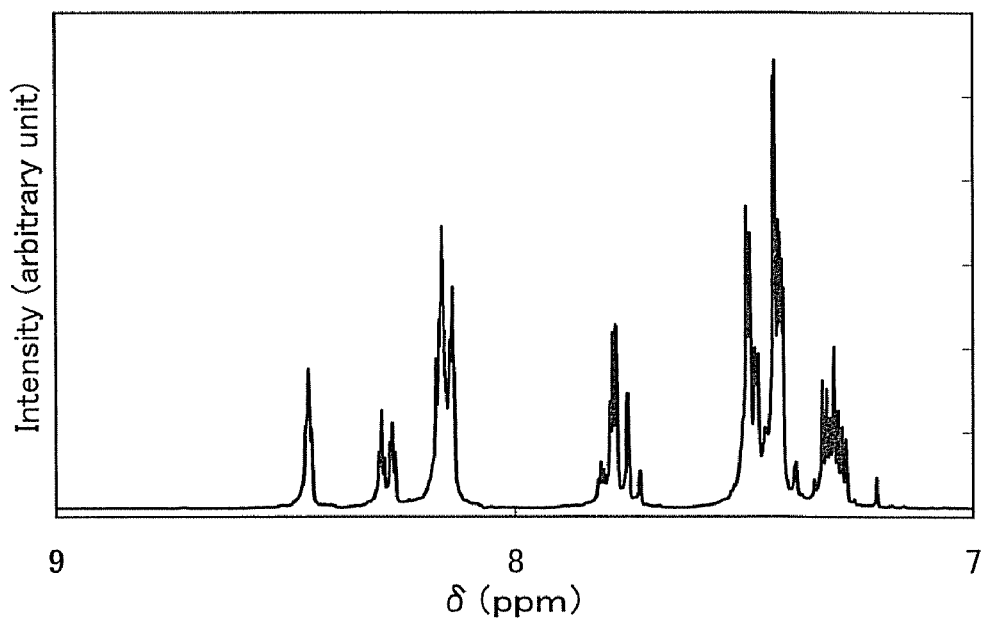

In addition, FIGS. 17A and 17B show $^1$H NMR charts. Note that FIG. 17B is an enlarged chart showing the range from 7.0 ppm to 9.0 ppm in FIG. 17A.

Figure 18:
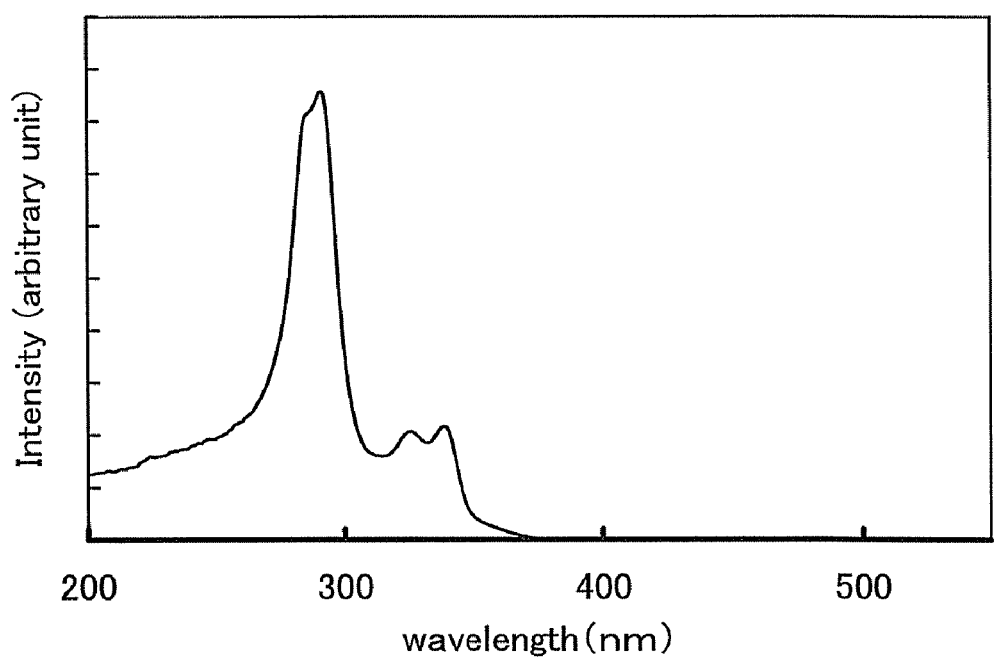
FIG. 18 shows an absorption spectrum of a toluene solution of mCzOd (abbreviation)
Figure 19:
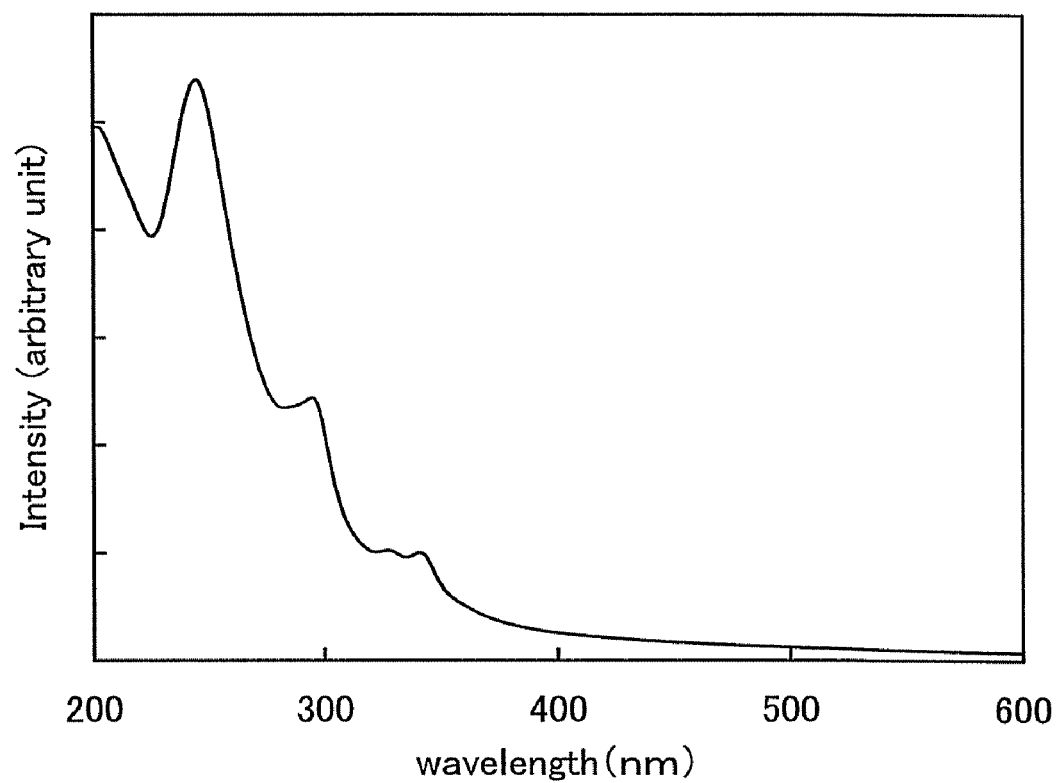
FIG. 19 shows an absorption spectrum of a thin film of mCzOd (abbreviation)
Figure 20:
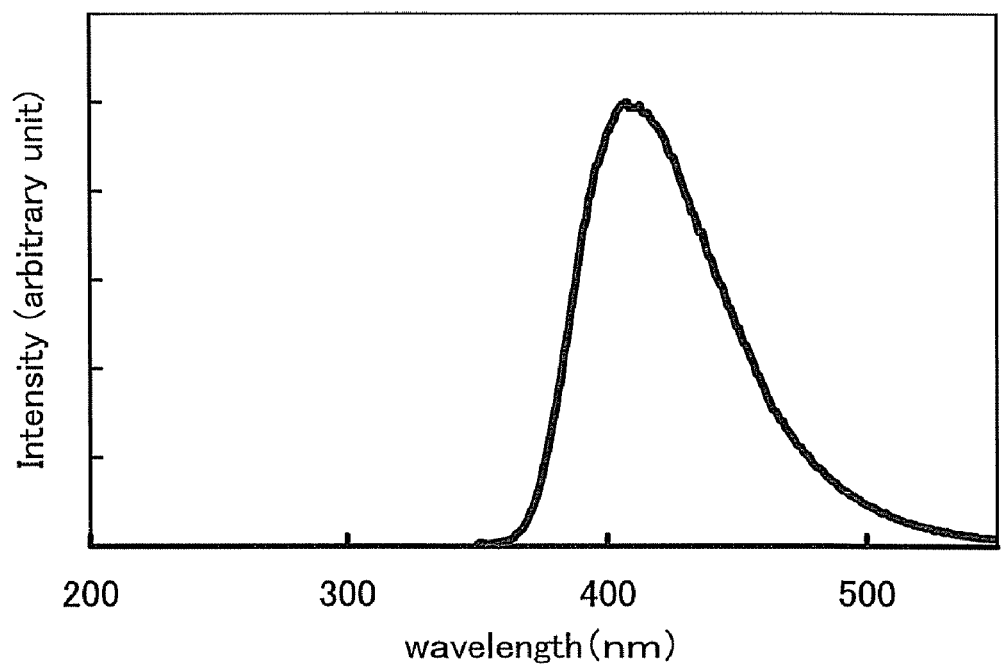
FIG. 20 shows an emission spectrum of a toluene solution of mCzOd (abbreviation)
Figure 21:
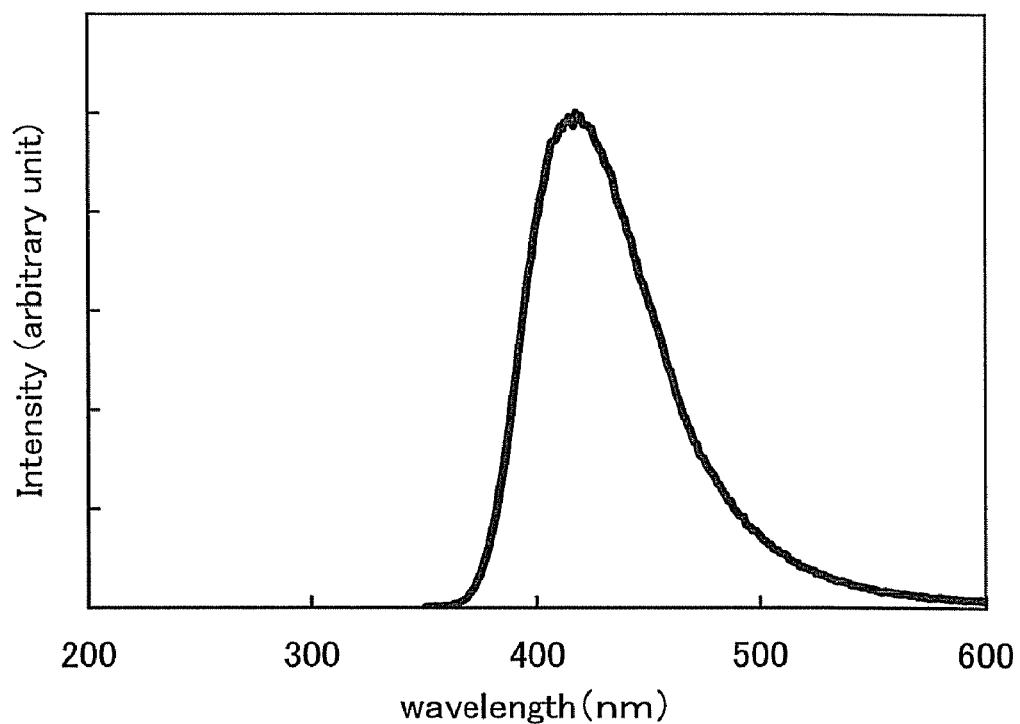
FIG. 21 shows an emission spectrum of a thin film of mCzOd (abbreviation)

FIG. 18 and FIG. 20 show an absorption spectrum and an emission spectrum, respectively, of a toluene solution of mCzOd (abbreviation). FIG. 19 and FIG. 21 show an absorption spectrum and an emission spectrum, respectively, of a thin film of mCzOd (abbreviation). An ultraviolet-visible spectrophotometer (V-550, manufactured by JASCO Corporation) was used for the measurement of the absorption spectrum. To prepare samples, the solution was put in a quartz cell while the thin film was obtained by evaporation onto a quartz substrate. As for the absorption spectrum of the solution, the absorption spectrum obtained by subtraction of the absorption spectra of the quartz cell and toluene is shown in FIG. 18. As for the spectrum of the thin film, the absorption spectrum obtained by subtraction of the absorption spectrum of the quartz substrate is shown in FIG. 20. In FIG. 18, FIG. 19, FIG. 20, and FIG. 21, the horizontal axis indicates wavelength (nm) and the vertical axis indicates intensity (arbitrary unit). In the case of the toluene solution, absorption was observed at around 336 nm, and the maximum emission wavelength was 412 nm (excitation wavelength: 339 nm). In the case of the thin film, absorption was observed at around 341 nm, and the maximum emission wavelength was 420 nm (excitation wavelength: 327 nm).

Further, the HOMO level and LUMO level of mCzOd (abbreviation) in the thin film state were measured. The value of the HOMO level was obtained by conversion of a value of ionization potential measured with a photoelectron spectrometer (AC-2, manufactured by Riken Keiki Co., Ltd.) in the atmosphere into a negative value. The value of the LUMO level was obtained in such a manner that the absorption edge was obtained from Tauc plot, with an assumption of direct transition, using data on the absorption spectrum of the thin film of mCzOd (abbreviation) in FIG. 19, and the obtained absorption edge was added to the HOMO level as an optical energy gap. As a result, the HOMO level and LUMO level of mCzOd (abbreviation) were found to be −5.90 eV and −2.68 eV, respectively, and the energy gap was found to be 3.22 eV.

Thus, mCzOd (abbreviation) is found to have a large energy gap.

Figure 32A:
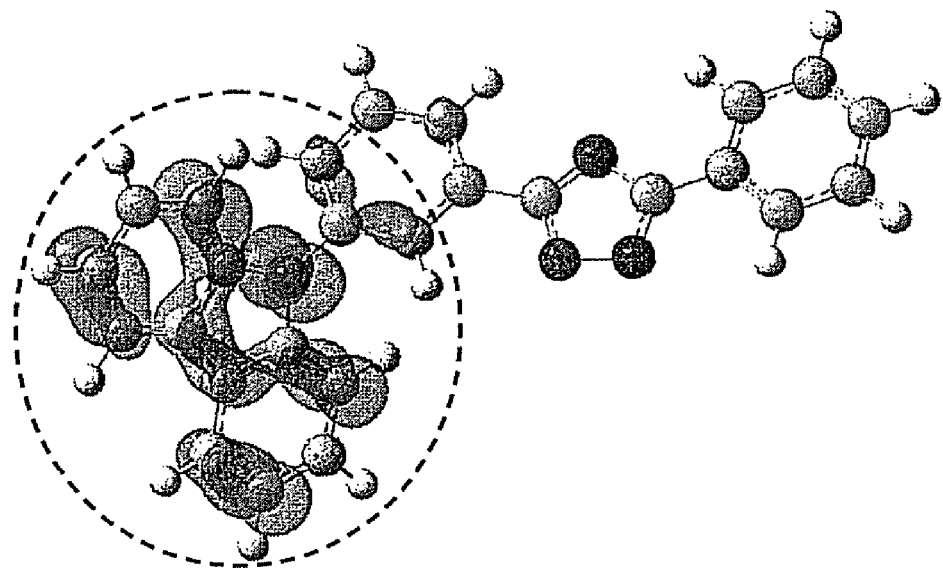
FIGS. 32A and 32B show the highest occupied molecular orbital (HOMO) and lowest unoccupied molecular orbital (LUMO) of mCzOd (abbreviation), respectively.
Figure 32B:
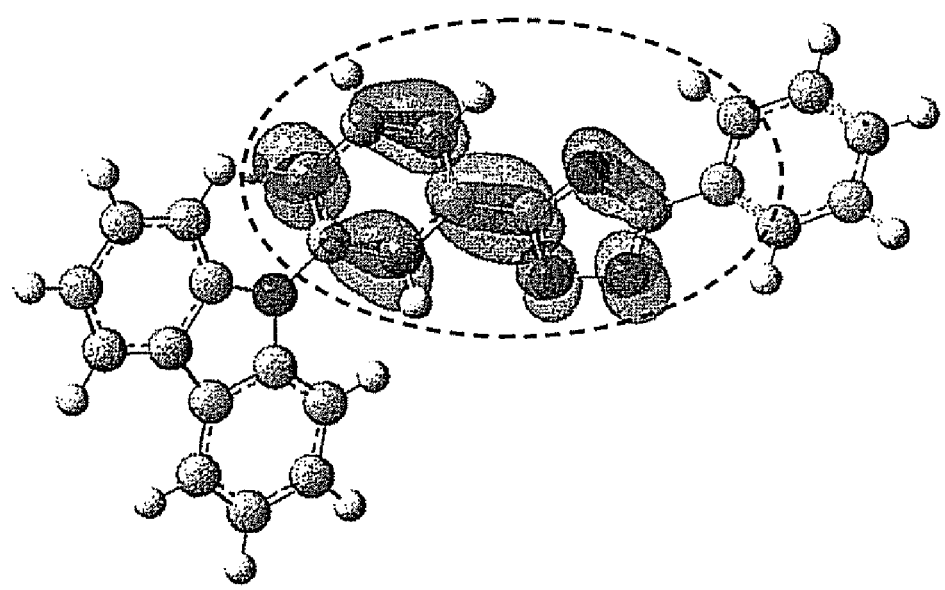

In addition, the optimal molecular structure of mCzOd (abbreviation) in the ground state was calculated by a method similar to that for CzOd (abbreviation) in the above-described example. FIGS. 32A and 32B show respectively the highest occupied molecular orbital (HOMO) and lowest unoccupied molecular orbital (LUMO) of mCzOd (abbreviation), which were found by the calculations. FIG. 32A shows the highest occupied molecular orbital (HOMO), and FIG. 32B shows the lowest unoccupied molecular orbital (LUMO). In the drawings, the spheres represent atoms forming mCzOd (abbreviation) and cloud-like objects around atoms represent orbits.

FIGS. 32A and 32B reveal that the highest occupied molecular orbital and lowest unoccupied molecular orbital of mCzOd (abbreviation) exist in a carbazole group and an oxadiazole group, respectively. In other words, the carbazole group contributes to the hole-transporting property of mCzOd (abbreviation) while the oxadiazole group contributes to the electron-transporting property thereof. The carbazole group is a unit exhibiting a high hole-transporting property, and the oxadiazole group is a unit exhibiting a high electron-transporting property, which proves the high bipolar property of mCzOd (abbreviation).

Example 3

In Example 3, a synthesis method of 4-(9H-carbazol-9-yl)-4'-(3-phenyl-1,2,4-oxadiazol-5-yl)triphenylamine (abbreviated to YGAOd) represented by Structural Formula (152), which is an oxadiazole derivative of the present invention, will be described specifically.

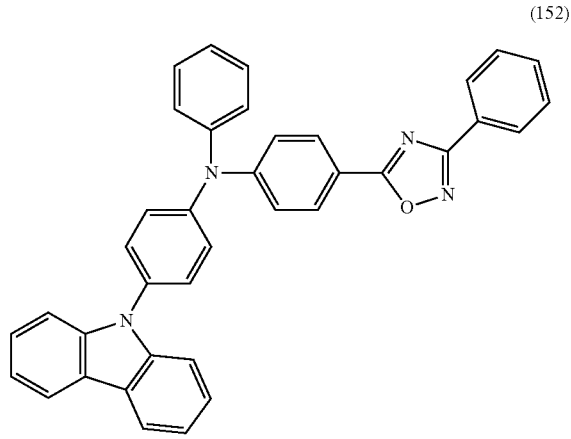

(152)

A synthesis scheme of YGAOd (abbreviation) is shown in (C-1).

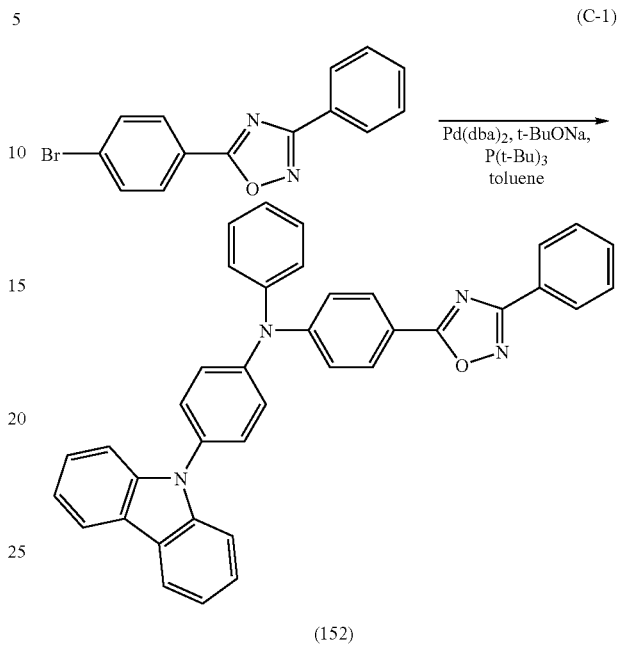

(C-1)

(152)

In a 100 mL three-neck flask, 1.0 g (3.3 mmol) of 5-(4-bromophenyl)-3-phenyl-1,2,4-oxadiazole, 0.90 g (9.3 mmol) of sodium tert-butoxide, 1.1 g (3.3 mmol) of 9-[4-(N-phenylamino)phenyl]carbazole (abbreviated to YGA), and 0.10 g (0.20 mmol) of bis(dibenzylideneacetone)palladium(0) were placed, and the air in the flask was replaced with nitrogen. Then, 20 mL of toluene and 0.10 mL of tri-tent-butylphosphine 10 wt % hexane solution were added into this mixture. This mixture was stirred at 80° C. for 5 hours under a nitrogen gas stream. After the stirring, toluene was added into the mixture, and the resulting suspension was suction filtered through Florisil (produced by Wako Pure Chemical Industries, Ltd., Catalog No. 540-00135), Celite (manufactured by Wako Pure Chemical Industries, Ltd., Catalog No. 531-16855), and alumina to give a filtrate. The filtrate was washed with water and brine in this order. Then, the organic layer was dried with magnesium sulfate. After the drying, this mixture was suction filtered. The resulting filtrate was concentrated to give a compound, and the compound was purified by silica gel column chromatography. The column chromatography was performed first using a mixed solvent of a 1:2 ratio of toluene to hexane as a developing solvent and then using a mixed solvent of a 3:2 ratio of toluene to hexane as a developing solvent. The compound which was obtained by concentrating the obtained fraction was recrystallized with a mixed solvent of chloroform and hexane to give 1.6 g of a white powdery solid in a yield of 87%.

Further, 1.6 g of the solid obtained was purified by sublimation by a train sublimation method. The sublimation purification was carried out at 265° C. for 7 hours under a reduced pressure of 7.0 Pa with a flow rate of argon at 3.0 mL/min. After the sublimation purification, 1.1 g of a solid which is YGAOd (abbreviation) was obtained in 61% yield.

Next, by a nuclear magnetic resonance (NMR) method, the compound obtained by the above-described synthesis method was confirmed to be 4-(9H-carbazol-9-yl)-4'-(3-phenyl-1,2, 4-oxadiazol-5-yl)triphenylamine (abbreviated to YGAOd), which was the desired compound.

The following are data of the $^1$H NMR of the obtained compound: $^1$H NMR (CDCl$_3$, 300 MHz): δ=7.19-7.53 (m, 20H), 8.06-8.19 (m, 6H).

Figure 22A:
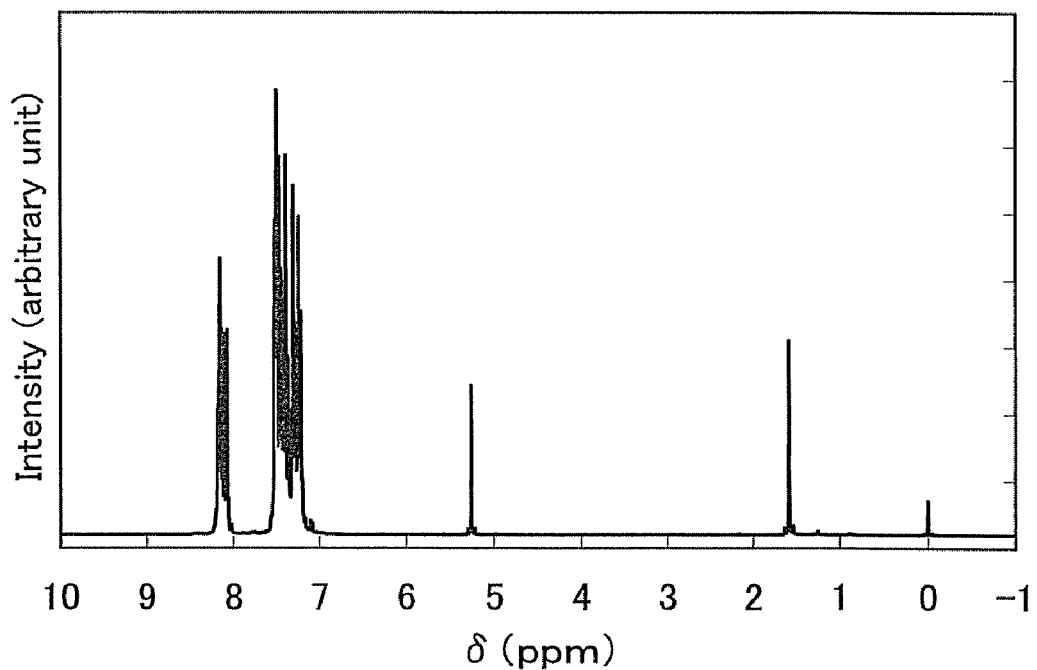
FIGS. 22A and 22B are graphs showing $^1$H NMR charts of YGAOd (abbreviation)
Figure 22B:
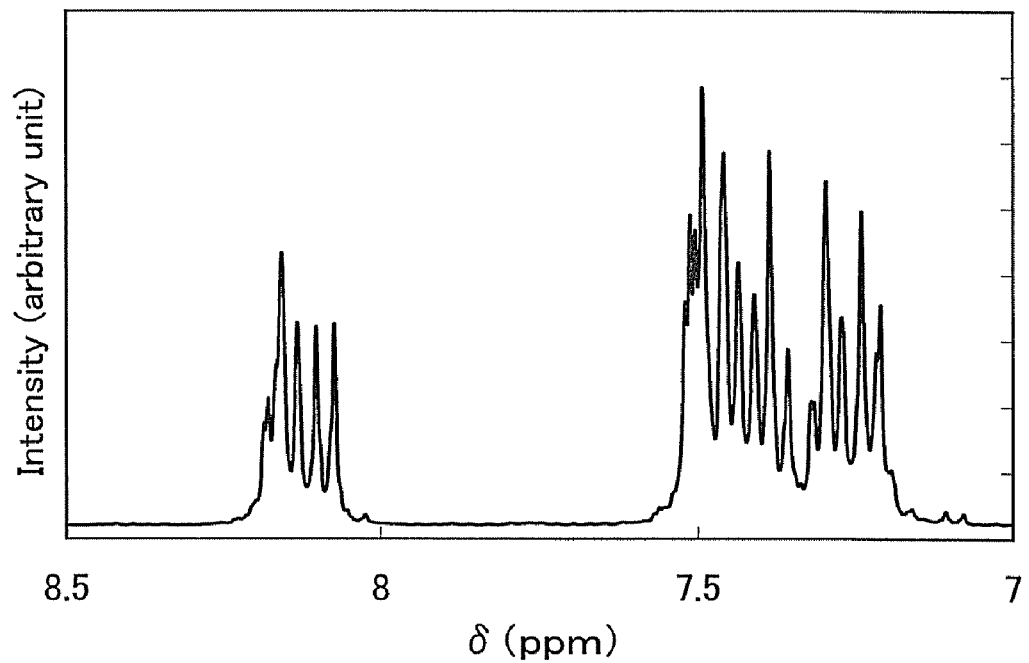

In addition, FIGS. 22A and 22B show $^1$H NMR charts. Note that FIG. 22B is an enlarged chart showing the range from 7.0 ppm to 8.5 ppm in FIG. 22A.

Figure 23:
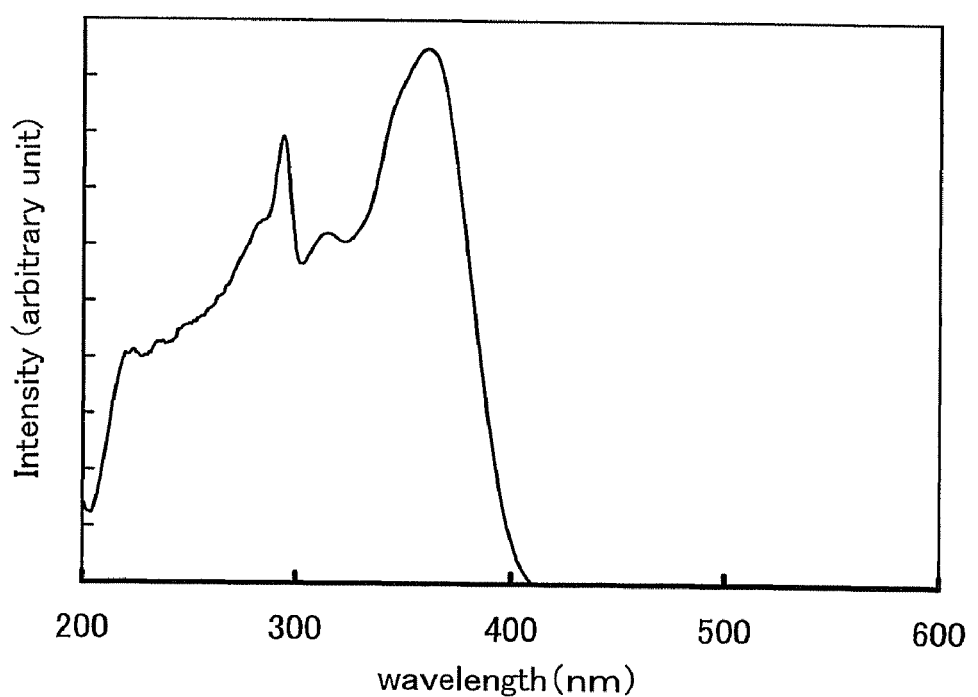
FIG. 23 shows an absorption spectrum of a toluene solution of YGAOd (abbreviation)
Figure 24:
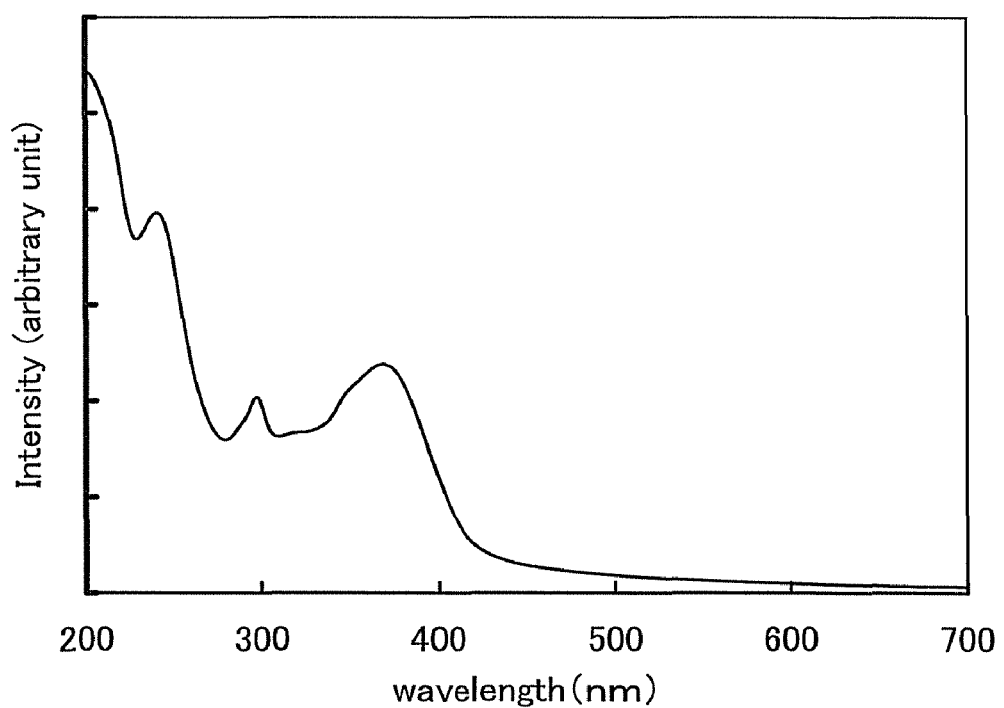
FIG. 24 shows an absorption spectrum of a thin film of YGAOd (abbreviation)
Figure 25:
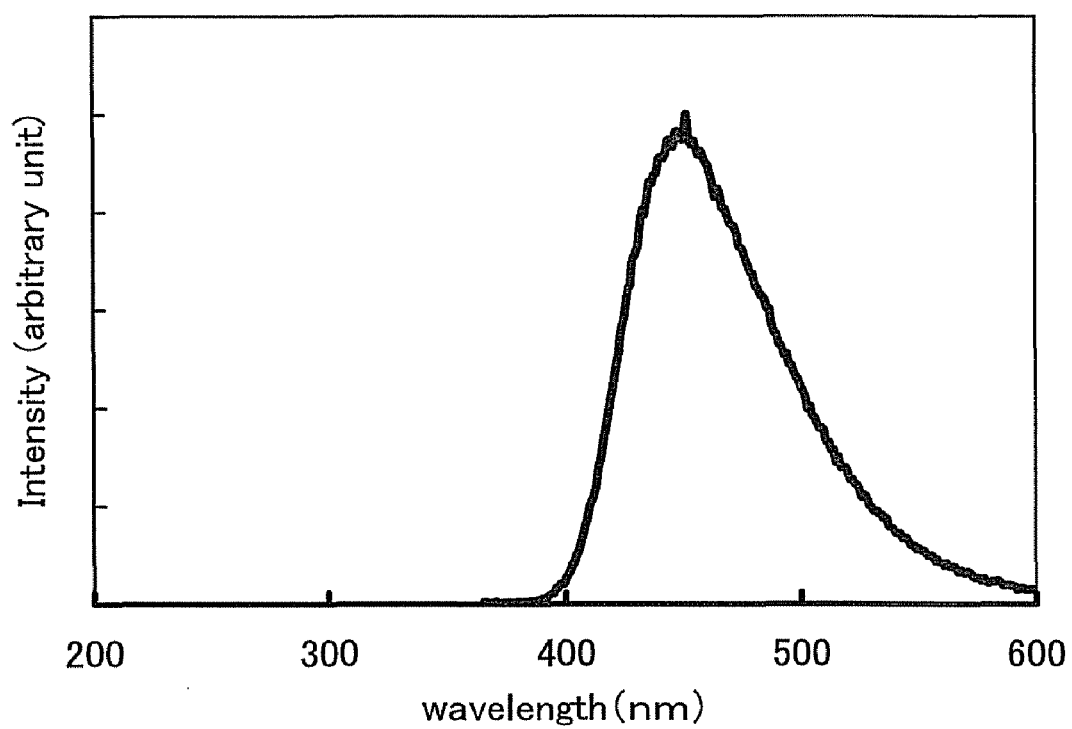
FIG. 25 shows an emission spectrum of a toluene solution of YGAOd (abbreviation)
Figure 26:
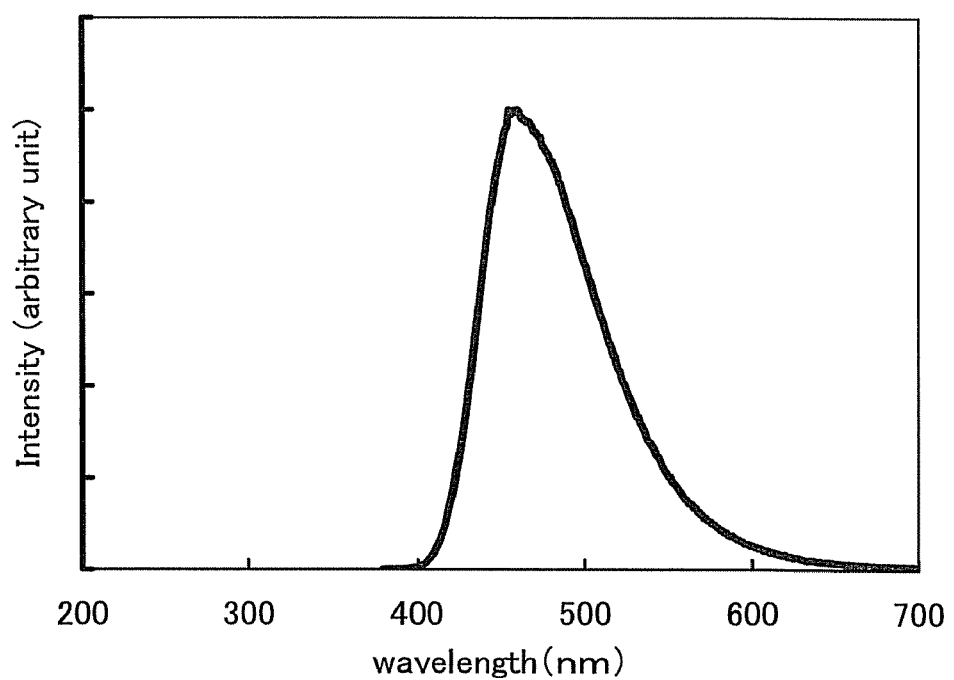
FIG. 26 shows an emission spectrum of a thin film of YGAOd (abbreviation)

FIG. 23 and FIG. 25 show an absorption spectrum and an emission spectrum, respectively, of a toluene solution of YGAOd (abbreviation). FIG. 24 and FIG. 26 show an absorption spectrum and an emission spectrum, respectively, of a thin film of YGAOd (abbreviation). An ultraviolet-visible spectrophotometer (V-550, manufactured by JASCO Corporation) was used for the measurement of the absorption spectrum. To prepare samples, the solution was put in a quartz cell while the thin film was obtained by evaporation onto a quartz substrate. As for the absorption spectrum of the solution, the absorption spectrum obtained by subtraction of the absorption spectra of the quartz cell and toluene is shown in FIG. 23. As for the spectrum of the thin film, the absorption spectrum obtained by subtraction of the absorption spectrum of the quartz substrate is shown in FIG. 24. In FIG. 23, FIG. 24, FIG. 25, and FIG. 26, the horizontal axis indicates wavelength (nm) and the vertical axis indicates intensity (arbitrary unit). In the case of the toluene solution, absorption was observed at around 357 nm, and the maximum emission wavelength was 450 nm (excitation wavelength: 357 nm). In the case of the thin film, absorption was observed at around 369 nm, and the maximum emission wavelength was 462 nm (excitation wavelength: 369 nm).

Further, the HOMO level and LUMO level of YGAOd (abbreviation) in the thin film state were measured. The value of the HOMO level was obtained by conversion of a value of ionization potential measured with a photoelectron spectrometer (AC-2, manufactured by Riken Keiki Co., Ltd.) in the atmosphere into a negative value. The value of the LUMO level was obtained in such a manner that the absorption edge was obtained from Tauc plot, with an assumption of direct transition, using data on the absorption spectrum of the thin film of YGAOd (abbreviation) in FIG. 24, and the obtained absorption edge was added to the HOMO level as an optical energy gap. As a result, the HOMO level and LUMO level of YGAOd (abbreviation) were found to be −5.65 eV and −2.60 eV, respectively, and the energy gap was found to be 3.05 eV.

Thus, YGAOd (abbreviation) is found to have a large energy gap.

Figure 33A:
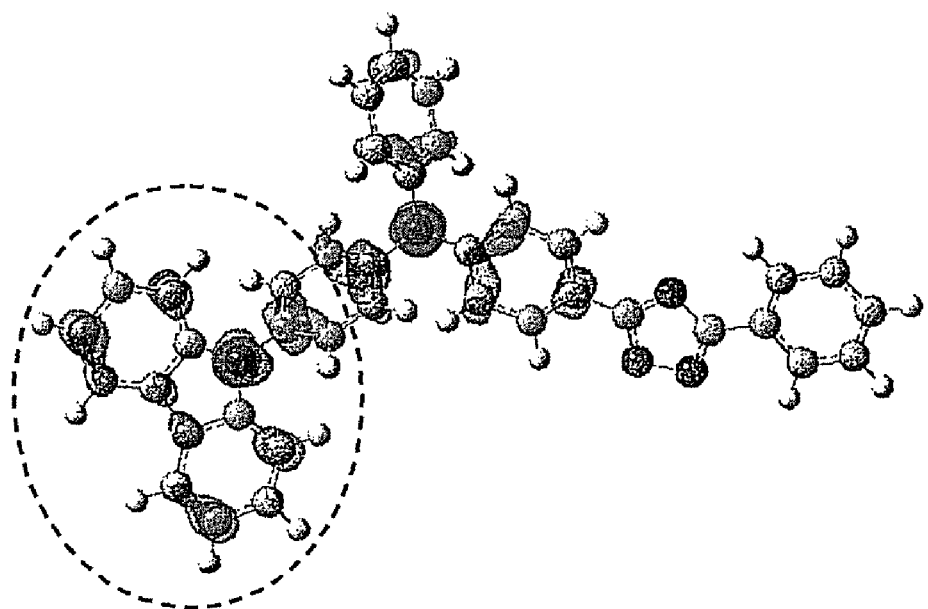
FIGS. 33A and 33B show the highest occupied molecular orbital (HOMO) and lowest unoccupied molecular orbital (LUMO) of YGAOd (abbreviation), respectively.
Figure 33B:
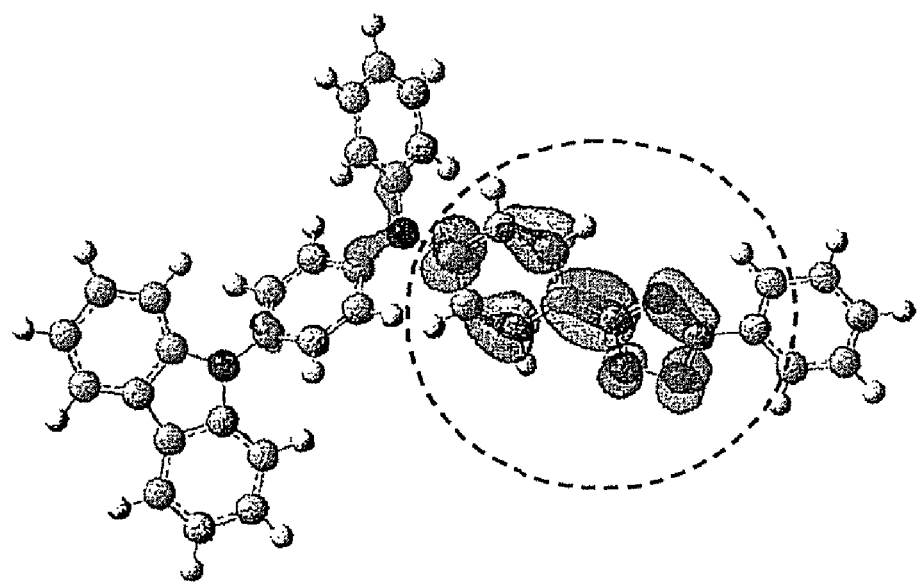

In addition, the optimal molecular structure of YGAOd (abbreviation) in the ground state was calculated by a method similar to that for CzOd (abbreviation) in the above-described example. FIGS. 33A and 33B show respectively the highest occupied molecular orbital (HOMO) and lowest unoccupied molecular orbital (LUMO) of YGAOd (abbreviation), which were found by the calculations. FIG. 33A shows the highest occupied molecular orbital (HOMO), and FIG. 33B shows the lowest unoccupied molecular orbital (LUMO). In the drawings, the spheres represent atoms forming YGAOd (abbreviation) and cloud-like objects around atoms represent orbits.

FIGS. 33A and 33B reveal that the highest occupied molecular orbital and lowest unoccupied molecular orbital of YGAOd (abbreviation) exist in a carbazole group and an oxadiazole group, respectively. In other words, the carbazole group contributes to the hole-transporting property of YGAOd (abbreviation) while the oxadiazole group contributes to the electron-transporting property thereof. The carbazole group is a unit exhibiting a high hole-transporting property, and the oxadiazole group is a unit exhibiting a high electron-transporting property, which proves the high bipolar property of YGAOd (abbreviation).

Example 4

Figure 10:
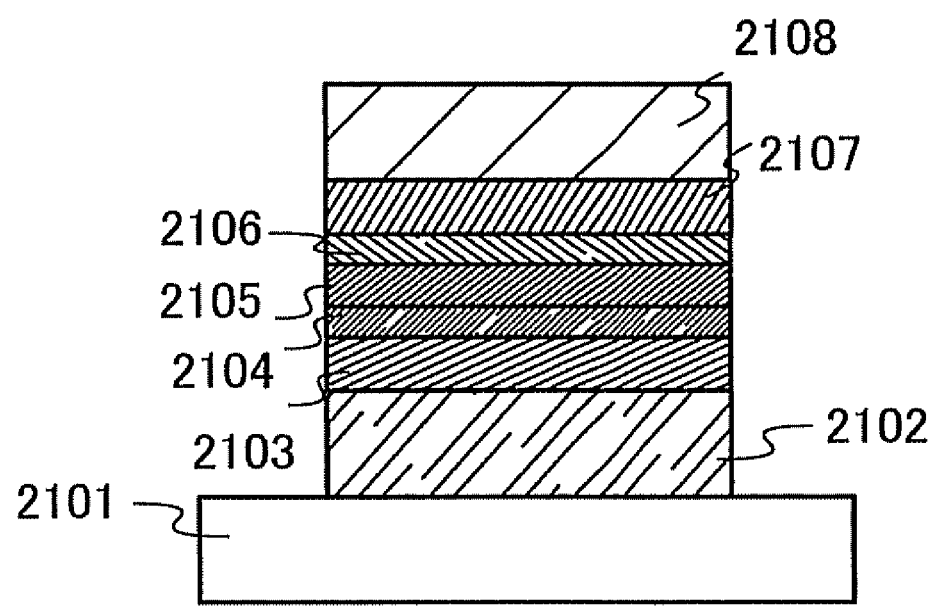
FIG. 10 is a view illustrating a light-emitting element of Example 4.

In Example 4, an example of a light-emitting element of the present invention will be described with reference to FIG. 10.

The element structure of the light-emitting element manufactured in this example is shown in Table 1. In Table 1, the mixture ratios are all represented by the weight ratio.

TABLE 1

| | first electrode 2102 | first layer 2103 | second layer 2104 | third layer 2105 | fourth layer 2106 | fifth layer 2107 | second electrode 2108 |
|---|---|---|---|---|---|---|---|
| light emitting element | ITSO 110 nm | NPB:MoOx(=4:1) 50 nm | NPB 10 nm | YGAOd:Ir(tppr)$_2$acac(1:0.06) 30 nm | BAlq 10 nm | Alq:Li(=1:0.01) 50 nm | Al 200 nm |

*all mix ratio is weight ratio

Hereinafter, a manufacturing method of the light-emitting element of this example will be described.

Indium tin oxide containing silicon oxide (ITSO) was deposited over a glass substrate 2101 by a sputtering method, so that a first electrode 2102 was formed. The thickness thereof was 110 nm and the electrode area was 2 mm×2 mm.

Next, the substrate over which the first electrode was formed was fixed to a substrate holder that was provided in a vacuum evaporation apparatus in such a way that a surface of the substrate having the first electrode faced downward. The pressure was reduced to be about 10$^{-4}$ Pa and then, 4,4'-bis [N-(1-napthyl)-N-phenylamino]biphenyl (abbreviated to NPB) and molybdenum(VI) oxide were co-evaporated on the first electrode 2102, thereby forming a first layer 2103 containing a composite material of an organic compound and an inorganic compound. The film thickness of the first layer 2103 was 50 nm, and the weight ratio of NPB to molybdenum (VI) oxide was set at 4:1 (=NPB: molybdenum oxide). It is to be noted that the co-evaporation method is an evaporation method in which evaporation is performed at one time from a plurality of evaporation sources in one process chamber.

Next, NPB was deposited by evaporation to be 10 nm thick, whereby a second layer 2104 was formed as a hole-transporting layer.

Then, YGAOd (abbreviation) synthesized in Example 3 and (acetylacetonato)bis(2,3,5-triphenylpyrazinato)iridium (III) (abbreviated to Ir(tppr)$_2$(acac)) were co-evaporated on the second layer 2104 so that the weight ratio of YGAOd (abbreviation) to Ir(tppr)$_2$(acac) was 1:0.06, thereby forming a third layer 2105 as a light-emitting layer. The thickness of the third layer was 30 nm.

Next, as a fourth layer 2106 serving as an electron-transporting layer, a BAlq film with a thickness of 10 nm was formed by evaporation on the third layer 2105. Further, Alq and Li were co-evaporated on the fourth layer 2106 so that the weight ratio of Alq to Li was 1:0.01, thereby forming a fifth layer 2107 with a thickness of 50 nm as an electron-injecting layer. Lastly, as a second electrode 2108 serving as a cathode, aluminum was deposited to a thickness of 200 nm, and thus the light-emitting element of this example was obtained. Note that, in the above evaporation process, evaporation was all performed by a resistance heating method. Structural Formulae of NPB, Ir(tppr)$_2$(acac), BAlq, and Alq are shown below.

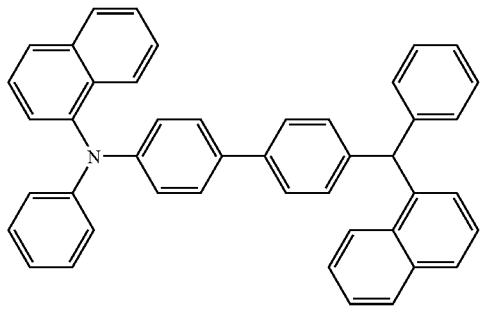

NPB

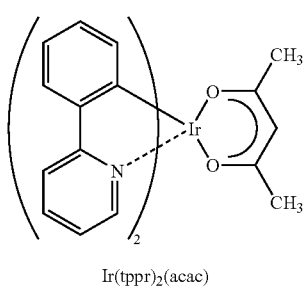

Ir(tppr)$_2$(acac)

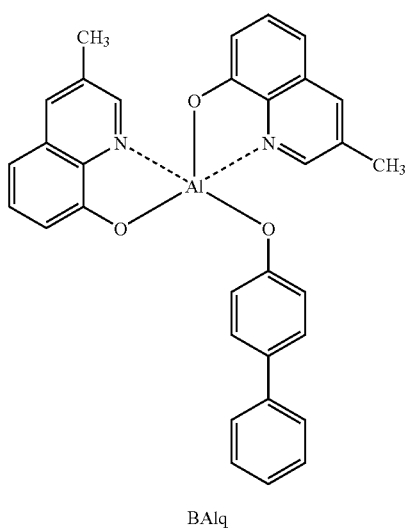

BAlq

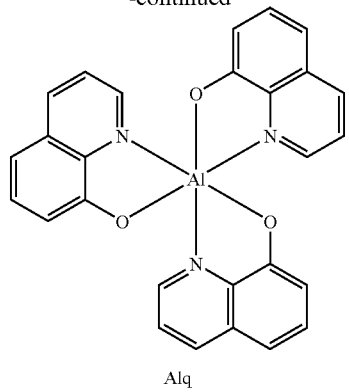

Alq

After the light-emitting element thus obtained was sealed in a glove box under a nitrogen atmosphere without being exposed to the air, operation characteristics of the light-emitting element were measured. Note that the measurement was carried out at room temperature (in an atmosphere kept at 25° C.).

Figure 27:
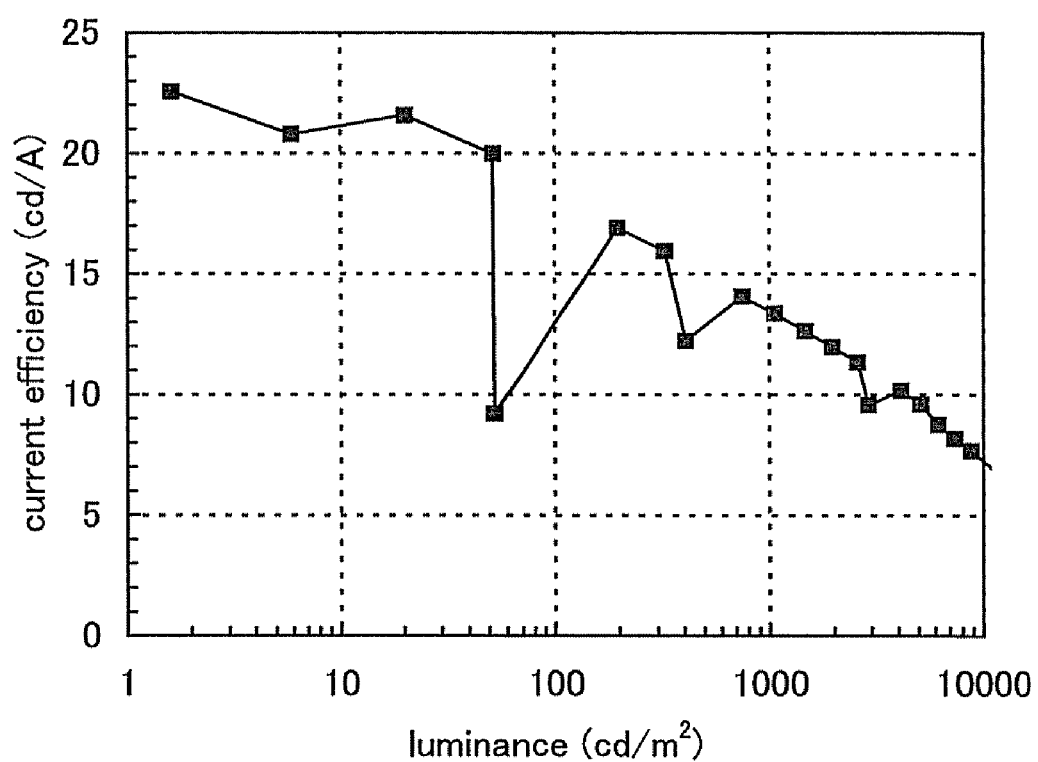
FIG. 27 shows luminance-current efficiency characteristics of a light-emitting element.
Figure 28:
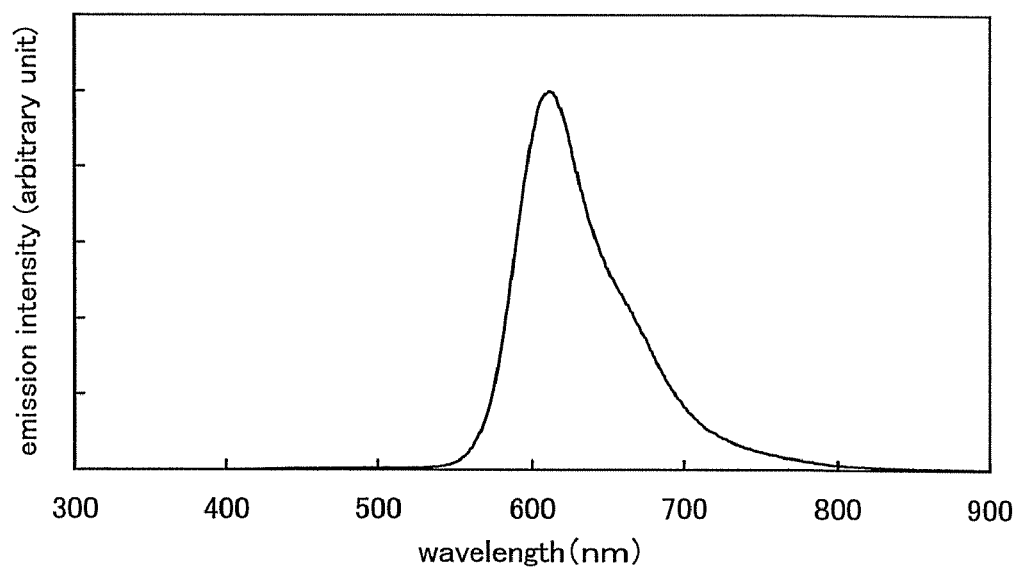
FIG. 28 shows an emission spectrum of a light-emitting element.
Figure 29:
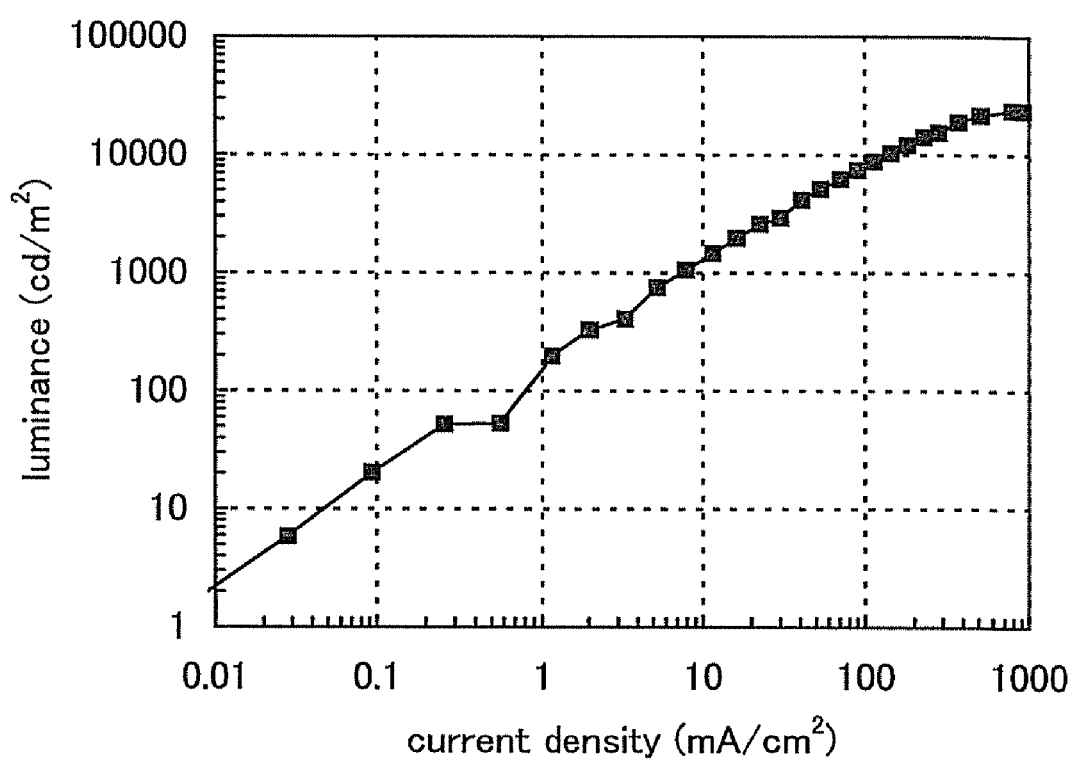
FIG. 29 shows current density-luminance characteristics of a light-emitting element.
Figure 30:
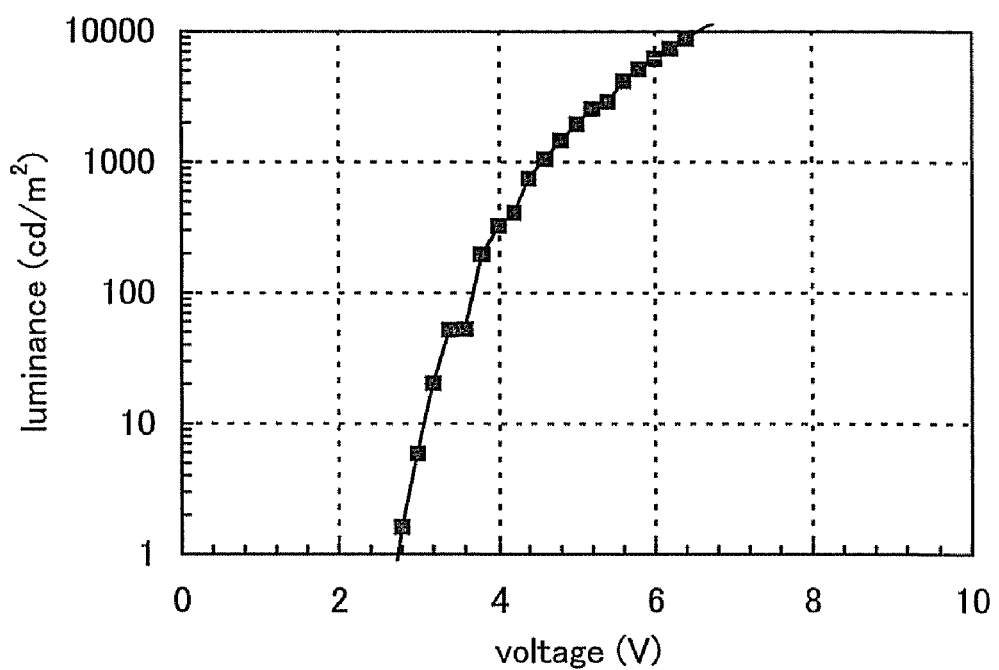
FIG. 30 shows voltage-luminance characteristics of a light-emitting element.

FIG. 27 shows the luminance-current efficiency characteristics thereof, FIG. 29 shows the current density-luminance characteristics thereof, and FIG. 30 shows the voltage-luminance characteristics of the light-emitting element. In addition, FIG. 28 shows the emission spectrum which was obtained at a current supply of 1 mA. From FIG. 28, it was found that excellent red light emission of Ir(tppr)$_2$(acac) having a peak at 612 nm was obtained from the light-emitting element. The light-emitting element had CIE chromaticity coordinates (x=0.64, y=0.36) at a luminance of 1058 cd/m$^2$ and exhibited favorable red light emission. Further, the current efficiency, external quantum efficiency, voltage, current density, and power efficiency at the luminance of 1058 cd/m$^2$ were 13.4 cd/A, 8.6%, 4.6 V, 7.92 mA/cm$^2$, and 9.12 lm/W, respectively.

As described above, it was confirmed that an embodiment of the light-emitting element of the present invention has characteristics as a light-emitting element and fully functions as a light-emitting element.

This application is based on Japanese Patent Application serial no. 2009-069176 filed with Japan Patent Office on Mar. 20, 2009, the entire contents of which are hereby incorporated by reference.

What is claimed is:
1. A light emitting device comprising:
an oxadiazole derivative represented by Formula (1),

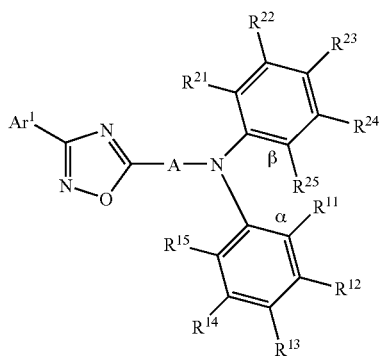

(1)

wherein Ar¹ represents a substituted or unsubstituted aryl group having 6 to 10 carbon atoms in a ring, wherein A represents a substituted or unsubstituted phenylene group, and wherein $R^{11}$ to $R^{15}$ and $R^{21}$ to $R^{25}$ are independently any of hydrogen, an alkyl group having 1 to 4 carbon atoms, an aryl group having 6 to 10 carbon atoms in a ring, and a substituted or unsubstituted 9H-carbazol-9-yl group.

2. The light emitting device according to claim 1, wherein the oxadiazole derivative is represented by Formula (2),

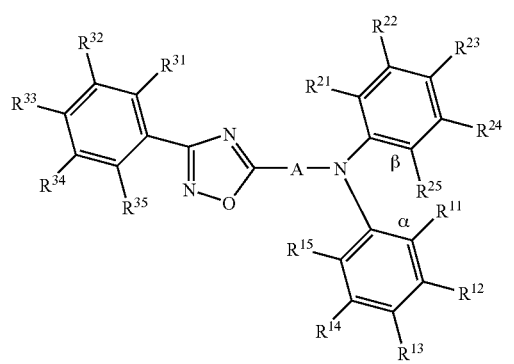

(2)

wherein $R^{31}$ to $R^{35}$ are independently any of hydrogen, an alkyl group having 1 to 4 carbon atoms, or an aryl group having 6 to 10 carbon atoms in a ring.

3. The light emitting device according to claim 1, wherein the oxadiazole derivative is represented by Formula (3),

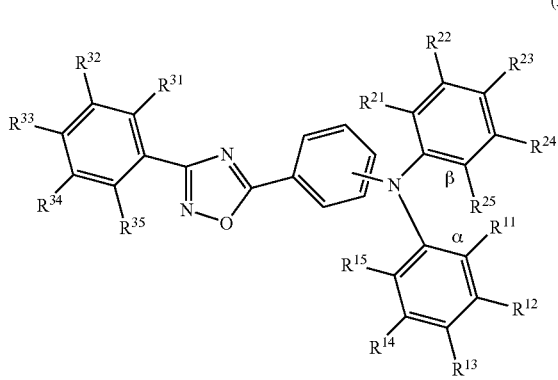

(3)

wherein $R^{31}$ to $R^{35}$ are independently any of hydrogen, an alkyl group having 1 to 4 carbon atoms, or an aryl group having 6 to 10 carbon atoms in a ring.

4. The light emitting device according to claim 1, wherein the oxadiazole derivative is represented by Formula (4),

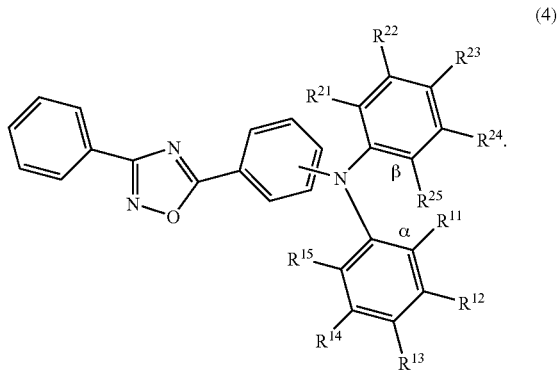

(4)

5. The light emitting device according to claim 1, wherein the oxadiazole derivative represented by Formula (5),

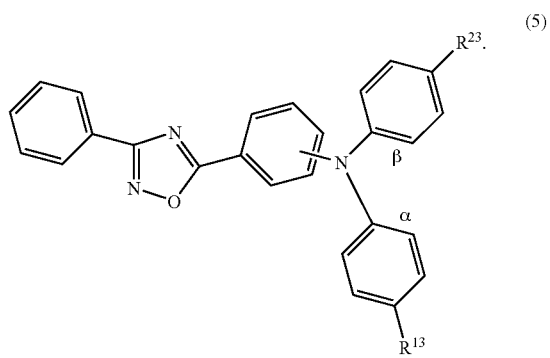

(5)

6. The light emitting device according to claim 1, wherein the oxadiazole derivative is represented by Formula (6),

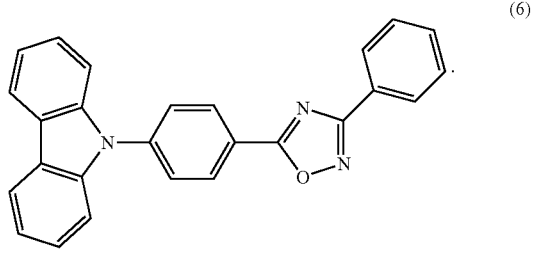

(6)

7. The light emitting device according to claim 1, wherein the oxadiazole derivative is represented by Formula (7),

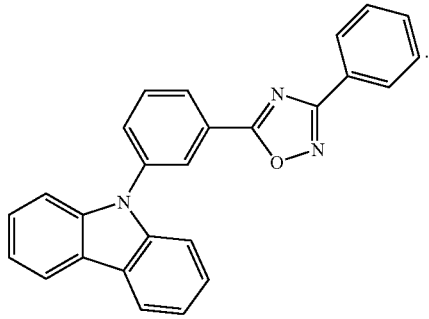

(7)

8. The light emitting device according to claim 1, wherein the oxadiazole derivative is represented by Formula (8),

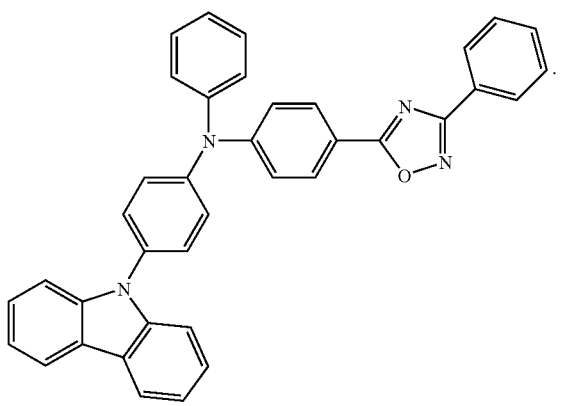

(8)

9. The light emitting device according to claim 1, wherein a substituent of A is an alkyl group having 1 to 4 carbon atoms.

10. The light emitting device according to claim 1, wherein at least one of $R^{11}$ to $R^{15}$ and $R^{21}$ to $R^{25}$ is 9H-carbazol-9-yl group, and
wherein a substituent of the 9H-carbazol-9-yl group is an alkyl group having 1 to 4 carbon atoms or an aryl group having 6 to 10 carbon atoms in a ring.

11. The light emitting device according to claim 1, wherein carbon at α position and carbon at β position are bonded to each other to form a carbazole ring.

12. The light emitting device according to claim 1, wherein the oxadiazole derivative is included in a light emitting layer as a host material.

13. The light emitting device according to claim 1, wherein the light emitting device is used as a backlight of a liquid crystal display device.

14. A lighting device comprising:
an oxadiazole derivative represented by Formula (1),

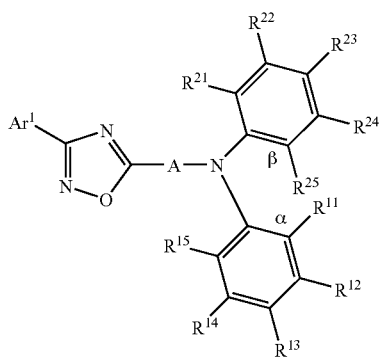

(1)

wherein $Ar^1$ represents a substituted or unsubstituted aryl group having 6 to 10 carbon atoms in a ring,
wherein A represents a substituted or unsubstituted phenylene group, and
wherein $R^{11}$ to $R^{15}$ and $R^{21}$ to $R^{25}$ are independently any of hydrogen, an alkyl group having 1 to 4 carbon atoms, an aryl group having 6 to 10 carbon atoms in a ring, and a substituted or unsubstituted 9H-carbazol-9-yl group.

15. The lighting device according to claim 14, wherein the lighting device is a table lamp.

16. The lighting device according to claim 14, wherein the lighting device is an indoor lighting device.

17. An oxadiazole derivative represented by Formula (1),

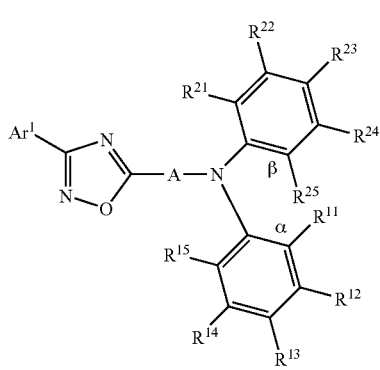

(1)

wherein $Ar^1$ represents a substituted or unsubstituted aryl group having 6 to 10 carbon atoms in a ring,
wherein A represents a substituted or unsubstituted phenylene group, and
wherein $R^{11}$ to $R^{15}$ and $R^{21}$ to $R^{25}$ are independently any of hydrogen, an alkyl group having 1 to 4 carbon atoms, an aryl group having 6 to 10 carbon atoms in a ring, and a substituted or unsubstituted 9H-carbazol-9-yl group.

18. The oxadiazole derivative according to claim 17, wherein the oxadiazole derivative is represented by Formula (6),
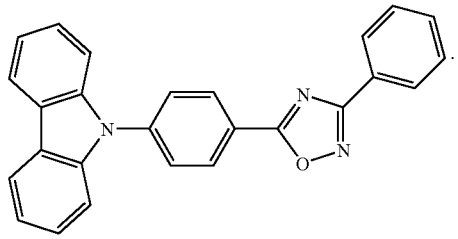
(6)
19. The oxadiazole derivative according to claim 17, wherein the oxadiazole derivative is represented by Formula (7),
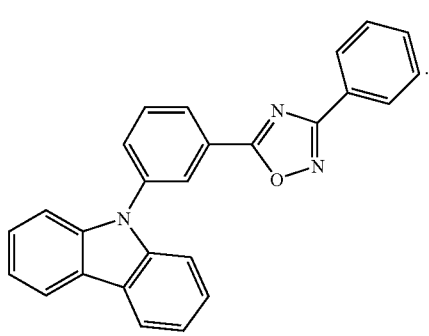
(7)
20. The oxadiazole derivative according to claim 17, wherein the oxadiazole derivative is represented by Formula (8),
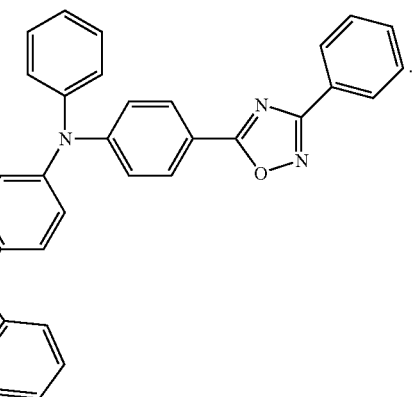
(8)
* * * * *